(12) United States Patent
Stupp et al.

(10) Patent No.: US 7,223,234 B2
(45) Date of Patent: May 29, 2007

(54) APPARATUS FOR DETERMINING ASSOCIATION VARIABLES

(75) Inventors: Steven Elliot Stupp, San Carlos, CA (US); Chris Carpenter, Sunnyvale, CA (US); Lawrence Newman, Katonah, NY (US); Gert Lanckriet, Berkeley, CA (US)

(73) Assignee: Monitrix, Inc., San Carlos, CA (US)

( * ) Notice: Subject to any disclaimer, the term of this patent is extended or adjusted under 35 U.S.C. 154(b) by 68 days.

(21) Appl. No.: 11/177,063

(22) Filed: Jul. 8, 2005

(65) Prior Publication Data

US 2006/0015263 A1    Jan. 19, 2006

Related U.S. Application Data

(60) Provisional application No. 60/601,480, filed on Aug. 14, 2004, provisional application No. 60/591,300, filed on Jul. 27, 2004, provisional application No. 60/587,003, filed on Jul. 10, 2004.

(51) Int. Cl.
*A61B 5/00* (2006.01)

(52) U.S. Cl. .................... 600/300; 600/301; 128/920; 128/898

(58) Field of Classification Search ........ 600/300–301; 128/903–905, 898, 920; 705/2–4
See application file for complete search history.

(56) References Cited

U.S. PATENT DOCUMENTS

| | | | |
|---|---|---|---|
| 5,307,263 A | 4/1994 | Brown | 600/301 |
| 5,331,549 A | 7/1994 | Crawford | 600/513 |
| 5,357,427 A | 10/1994 | Langen et al. | 600/300 |
| 5,434,611 A | 7/1995 | Tamura | 725/116 |
| 5,437,278 A | 8/1995 | Wilk | 600/425 |
| 5,441,047 A | 8/1995 | David et al. | 600/483 |
| 5,772,586 A | 6/1998 | Heinonen | 600/300 |
| 5,897,493 A | 4/1999 | Brown | 600/300 |

(Continued)

FOREIGN PATENT DOCUMENTS

WO    WO 2004/027676    4/2004

OTHER PUBLICATIONS

Katharina Dalton, "Food Intake Prior to Migraine Attacks-Study of 2,313 Spontaneous Attacks," Headache 15, pp. 188-193 (1975).

(Continued)

*Primary Examiner*—Max Hindenburg
*Assistant Examiner*—Filip Kowalewski
(74) *Attorney, Agent, or Firm*—Steven Elliot Stupp

(57) ABSTRACT

An apparatus, and related method, for determining one or more association variables is described. The apparatus includes at least one processor, at least one memory, and at least one program module. The program module is stored in the memory and is configurable to be executed by the processor. The program module includes instructions for determining a statistical relationship between one or more temporal onsets corresponding to one or more events and a pattern of occurrence of a compound variable. The compound variable corresponds at least to a pattern of occurrence of a first variable and a pattern of occurrence of a second variable. The determining includes contributions from presence and absence information in the pattern of occurrence of the compound variable.

24 Claims, 19 Drawing Sheets

U.S. PATENT DOCUMENTS

| | | | | |
|---|---|---|---|---|
| 5,911,132 | A | 6/1999 | Sloane | 705/3 |
| 5,950,632 | A | 9/1999 | Reber et al. | 128/898 |
| 5,960,403 | A | 9/1999 | Brown | 705/2 |
| 5,995,077 | A | 11/1999 | Wilcox et al. | 715/841 |
| 5,997,476 | A | 12/1999 | Brown | 600/300 |
| 6,101,478 | A | 8/2000 | Brown | 705/2 |
| 6,122,351 | A | 9/2000 | Schleuter, Jr. et al. | 379/106.02 |
| 6,139,494 | A | 10/2000 | Cairnes | 600/300 |
| 6,151,586 | A | 11/2000 | Brown | 705/14 |
| 6,168,563 | B1 | 1/2001 | Brown | 600/301 |
| 6,234,964 | B1 | 5/2001 | Iliff | 600/300 |
| 6,270,455 | B1 | 8/2001 | Brown | 600/300 |
| 6,278,999 | B1 | 8/2001 | Knapp | 707/9 |
| 6,290,646 | B1 | 9/2001 | Cosentino et al. | 600/300 |
| 6,317,700 | B1 | 11/2001 | Bagne | 702/181 |
| 6,334,778 | B1 | 1/2002 | Brown | 434/258 |
| 6,364,834 | B1 | 4/2002 | Reuss et al. | 600/300 |
| 6,368,273 | B1 | 4/2002 | Brown | 600/300 |
| 6,381,577 | B1 | 4/2002 | Brown | 705/2 |
| 6,409,662 | B1 | 6/2002 | Lloyd et al. | 600/300 |
| 6,440,068 | B1 | 8/2002 | Brown et al. | 600/300 |
| 6,450,955 | B1 | 9/2002 | Brown et al. | 600/300 |
| 6,454,705 | B1 | 9/2002 | Consentino et al. | 600/300 |
| 6,458,080 | B1 | 10/2002 | Brown et al. | 600/300 |
| 6,527,712 | B1 | 3/2003 | Brown et al. | 600/300 |
| 6,569,094 | B2 | 5/2003 | Suzuki et al. | 600/300 |
| 6,602,191 | B2 | 8/2003 | Quy | 600/300 |
| 6,616,613 | B1 | 9/2003 | Goodman | 600/504 |
| 6,641,532 | B2 | 11/2003 | Iliff | 600/300 |
| 6,669,631 | B2 | 12/2003 | Norris | 600/300 |
| 6,712,763 | B2 * | 3/2004 | Abraham-Fuchs et al. | 600/300 |
| 6,755,783 | B2 | 6/2004 | Consentino et al. | 600/300 |
| 6,825,332 | B1 | 11/2004 | Frants et al. | 536/23.5 |
| 2001/0056229 | A1 | 12/2001 | Consentino et al. | 600/300 |
| 2002/0035486 | A1 * | 3/2002 | Huyn et al. | 705/3 |
| 2002/0173991 | A1 | 11/2002 | Boaz | 705/2 |
| 2003/0009088 | A1 | 1/2003 | Korth et al. | 600/300 |
| 2004/0102685 | A1 | 5/2004 | Consentino et al. | 600/300 |
| 2004/0122706 | A1 | 6/2004 | Walker et al. | 705/2 |
| 2004/0130450 | A1 | 7/2004 | Kleinschmidt | 340/573.1 |
| 2004/0186746 | A1 | 9/2004 | Angst | 705/3 |
| 2004/0210458 | A1 | 10/2004 | Evans | 705/2 |

OTHER PUBLICATIONS

J.B. Brainard, "Salt Load as a Trigger for Migraine," Minn. Med. 59(4), pp. 232-233 (1976).
G. Nappi et al., "Headache Temporal Patterns: Towards a Chronobiological Model," Cephalalgia 3 suppl. 1, pp. 21-30 (1983).
R. C. Peatfield et al., "The Prevalence of Diet-Induced Migraine," Cephalalgia 4, pp. 179-183 (1984).
J. Blau, "Pathogenesis of Migraine Attack: Initiation," J R Coll Physicians Lond 19, pp. 166-168 (1985).
S. Diamond et al., "Diet and Headache: Is There a Link?" Postgrad. Med. 79(14), pp. 279-286 (1986).
Vic van den Bergh et al., "Trigger Factors in Migraine: A Study Conducted by the Belgian Migraine Society," Headache 27(4), pp. 191-196 (1987).
J. N. Blau et al., "Preventing Migraine: A Study of Precipitating Factors," Headache 28, pp. 481-483 (1988).
R. B. Lipton et al., "Aspartame as a Dietary Trigger of Headache," Headache 29(2), pp. 90-92 (1989).
V. Glover et al., "The biochemical basis of migraine predisposition," in "Migraine: A Spectrum of Ideas," Sandler, M. and Collins, G.M., eds. (Oxford University Press. Oxford, 1990), pp. 228-241.
T. Köhler et al., "Daily Stress as a Trigger of Migraine Attacks: Results of Thirteen Single-Subject Studies," J. Consult. Clin. Psychol. 58(6), pp. 870-872 (1990).
G. de Matteis et al., "Geomagnetic Activity, Humidity, Temperature and Headache: Is There Any Correlation?" Headache 34(1), pp. 41-43 (1994).
B. G. Buchanan et al., "An Intelligent Interactive System for Delivering Individualized Information to Patients," Artificial Intelligence in Medicine 7, pp. 117-154 (1995).
M. Sandler et al., "Diet Migraine: Recent Progress in the Red (and White) Wine Story," Cephalalgia 15(2), pp. 101-103 (1995).
L. C. Turner et al., "Migraine Trigger Factors in Non-Clinical Mexican-American Population in San Diego County: Implications for Etiology," Cephalalgia 15(6), pp. 523-530 (1995).
R. Leira et al., "Diet and Migraine," Rev. Neurol. 24(129), pp. 534-538 (1996).
D. A. Marcus et al., "A Double-Blind Provocative Study of Chocolate as a Trigger of Headache," Cephalalgia 17(8), pp. 855-862 (1997).
E. M. William et al., "Guidelines for the Nonpharmacologic Management of Migraine in Clinical Practice," Canadian Medical Association Journal 159(1), pp. 47-54 (1998).
"Two by Two Tables," Simple Interactive Statistical Analysis, http://home.clara.net/sisa/two2hlp.htm, Feb. 18, 1999.
"Correlation," Creative Research Systems, http://www.survey system.com/correlation.htm, Feb. 21, 1999.
H. Chabriat et al., "Precipitating Factors of Headache: A Prospective Study in a National Control-Matched Survey in Migraineurs and Nonmigraineurs," Headache 39(5), pp. 335-338 (1999).
"Diet," http://www.painforum.com/en/1/hcpmigprediet.html, Nov. 11, 1999.
L. J. Cooke et al., "Chinook Winds and Migraine Headaches," Neurology 54(2), pp. 302-307 (2000).
"Fisher Exact," Simple Interactive Statistical Analysis, http://home.clara.net/sisa/fishrhlp.htm, Mar. 9, 2000.
Headache Diary, http://www.pancare.net/html/head-ache_diary.asp, PainCare, Inc., Aug. 24, 2000.
"7.3.3. How Can We Determine Whether Two Processes Produce the Same Proportion of Defectives?" NIST Engineering Statistics Handbook, http://www.itl.nist.gov/div898/handbook/prc/section3/prc33.htm, Oct. 4, 2000.
S. D. Silberstein et al., "Migraine: Diagnosis and Treatment," in "Wolff's Headache and Other Head Pain," Seventh Edition, Silberstein, S.D., Lipton, R.B., and Dalessio, D.J., eds. (Oxford University Press, New York, 2001), pp. 135-140 and 210-237.
V. T. Martin et al., "Toward a Rational Understanding of Migraine Trigger Factors," Med Clin North Am. 85(4), pp. 911-941 (2001).
"Migraine," Merck Medicus Modules, http://www.merckmedicus.com/pp/us/hcp/diseasemodules/migraine/default.jsp, Jul. 16, 2001.
R. A. Davidoff, "Initiators, Precipitators, and Triggers," in "Migraine: Manifestations, Pathogenesis and Management," Chapter 5 (Oxford, University Press, 2002).
P. J. Goadsby et al., "Migraine—Current Understanding and Treatment," N. Engl. J. Med. 346(4), pp. 257-268 (2002).
Dang Quang A et al., "Correlation Analysis," http://www.netnam.vn/unescocourse/statistics/11_6.htm, Mar. 26, 2002.
John Wasson, "Ed 602—Lesson 14—Chi-Square," http://www.mnstate.edu/wasson/ed620lesson14.htm, Jun. 26, 2002.
John Wasson, "Ed 602—Lesson 15—Testing the Significance of Correlation Coefficients, Choosing the Proper Statistical Test," http://www.mnstate.edu/wasson/ed620lesson15.htm, Jun. 26, 2002.
R. Lerusalimschy et al., "Precipitating Factors of Migraine Attacks in Patients With Migraine Without Aura," Arq Neutropsiquiatr. 60(3-A), pp. 609-613 (2002).
J. G. Millichap et al., "The Role of Diet in Migraine Headaches," http://www.nutrition4health.org/NOHAnews/NNS02DietMigraineHeadaches.htm, Oct. 29, 2002.
J. Connor-Linton, "Chi Square Tutorial," http://www.georgetown.edu/faculty/ballc/webtools/web_chi_tut.html, Dec. 22, 2002.
J. G. Millichap et al.; "The Diet Factor in Pediatric and Adolescent Migraine," Pediatric Neurology 28(1), pp. 9-15 (2003).
S. Borgatti, "Distance and Correlation," Analytic Technologies, http://www.analytictech.com/mb813/handouts/distance_and _ correlation.htm, Jan. 24, 2003.
"MedSearch Technologies, Inc. Develops a Revolutionary Home-Care Wireless Technology Utilizing PDAs—Personal Organizers—as Patient Monitors," MedSearch Technologies, http:www.mobic.com/oldnews/2000/09/medsearch_technologies.htm, May 18, 2003.

R. Zivadinov et al., "Migraine and Tension-Type Headaches in Croatia: A Population-Based Survey of Precipitating Factors," Cephalalgia 23(5), pp. 336-343 (2003).

"Managing Migraine: Translating Research into Clinical Practice," Medscape, http://www.medscape.com/viewprogram/2644_pnt, Sep. 26, 2003.

PDA Migraine Manager, TIS Software, http://www.tissoftware.net/products.htm, Dec. 14, 2003.

iMetrikus, Products and Markets, http://www.imetrikus.com/products.asp, iMetrikus, Feb. 28, 2004.

"The International Classification of Headache Disorders," 2$^{nd}$ Edition, Cephalalgia 24 suppl. 1, pp. 9-160 (2004).

K. E. Gordon et al., "Self-Reported Headache Frequency and Features Associated with Frequent Headaches in Canadian Young Adolescents," Headache 44, pp. 555-561 (2004).

P. B. Prince et al., "The Effect of Weather on Headache," Headache 44, pp. 596-602 (2004).

J. Ressner, "Push-Button Medicine," Time Magazine, Aug. 9, 2004, p. 101.

R. Baraniuk, "Angle Between Vectors: Inner Products," http://cnx.rice.edu/content/m12101/latest/, Oct. 24, 2004.

C. Hermann et al., "Use of Hand-Held Computers for Symptom-Monitoring: The Case of Chronic Headache," Min/Body Medicine 1(2), pp. 59-69 (1995).

P.C. Honkoop et al., "High-Density Assessment of the IHS Classification Criteria for Migraine Without Aura: A Prospective Study," Cephalalgia 19, pp. 201-206 (1999).

K.A. Holroyd et al., "A Hand-Held Computer Diary," presented at the American Headache Society Convention, Montreal, Canada (2000). The "Palm Diary Manual" that this presentation was based on is enclosed.

V. Yaremchuk, "Artificial Neural Networks and the Treatment of Migraine," M.S. thesis, Apr. 30, 2002, http://www.cs.ualberta.ca/~jonathan/Grad/vanessa.msc.ps.

L.A. Lenert et al., "Potential Validity of Conducting Research on Headache in Internet Populations," Headache 42, pp. 200-203 (2002).

K.A. Holroyd, "Assessment and Psychological Management of Recurrent Headache Disorders," J. Consulting and Clinical Psychology 70(3), pp. 656-677 (2002).

R.A. Nicholson et al., "Moderators and Mediators of Behavior in Treatment for Headache," Headache 45, pp. 513-519 (2005).

* cited by examiner

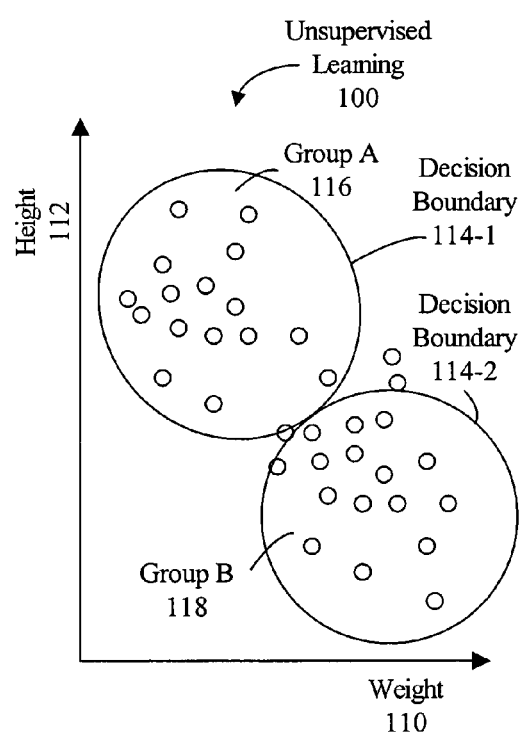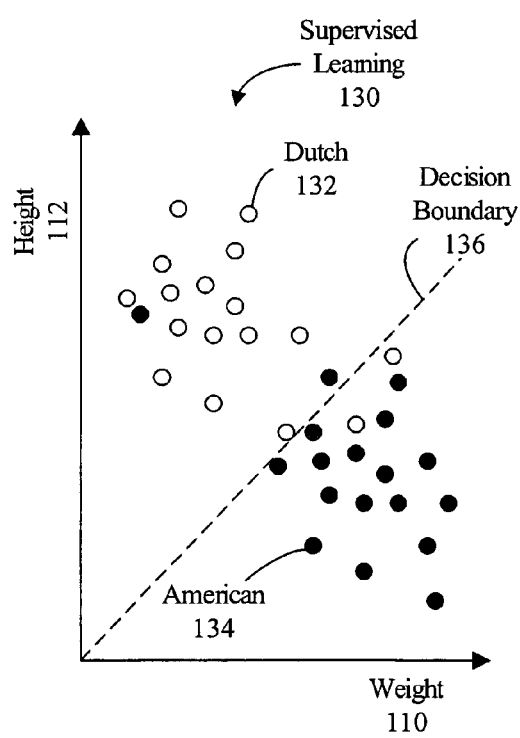
Figure 1A
(Prior Art)
Figure 1B
(Prior Art)

APPARATUS FOR DETERMINING ASSOCIATION VARIABLES

CROSS REFERENCE TO RELATED APPLICATIONS

This application claims priority under 35 U.S.C. 119(e) to U.S. Provisional Application Ser. No. 60/601,480, "Medical Informatics System," filed on Aug. 14, 2004, to U.S. Provisional Application Ser. No. 60/591,300, entitled "Healthcare Provider-Patient Interaction Management System," filed on Jul. 27, 2004, and to U.S. Provisional Application Ser. No. 60/587,003, entitled "Medical Informatics System," filed on Jul. 10, 2004, the contents of each of which are herein incorporated by reference.

FIELD OF THE INVENTION

The present invention relates generally to an apparatus, and related methods, for processing data, and more specifically, for determining statistical relationships.

BACKGROUND OF THE INVENTION

Statistical learning problems may be categorized as supervised or unsupervised. In supervised learning, the goal is to predict an output based on a number of input factors or variables (henceforth, referred to as variables), where a prediction rule is learned from a set of examples (referred to as training examples) each showing the output for a respective combination of variables. In unsupervised learning, the goal is to describe associations and patterns among a set of variables without the guidance of a specific output. An output may be predicted after the associations and patterns have been determined. These categories are illustrated in FIGS. 1A and 1B, which show data points as a function of weight 110 and height 112. In unsupervised learning 100 in FIG. 1A, the data may be described by input variables weight 110 and height 112 without any additional information (e.g., labels) that could help to find patterns in the data. Patterns in the data may be found by learning that there are two distinguished "clusters" of data points (represented by circles or decision boundaries 114 around them). Within each cluster, data in group A 116 or group B 118 are highly similar (i.e., close) and between clusters data are highly dissimilar (i.e., further away). When a new data point, i.e., combination of the input variables becomes available, it may be categorized as similar to and thus a potential member of one of the clusters that have been discovered, or as an outlier or as a member of a new cluster.

In supervised learning 130 in FIG. 1B, additional information about the data is available. The data points are labeled as Dutch 132 (white circles) or American 134 (filled-black circles). This extra information is exactly the output one wants to predict for future data. Having it available for the training data or examples allows predictive decision boundary 136 to be determined. In general, statistical learning involves finding a statistical model that explains the observed data that may be used to analyze new data, e.g., learning a weighted combination of numerical variables from labeled training data to predict a class or classification for a new combination of variables. Determining a model to predict quantitative outputs (continuous variables) is often referred to as regression. Determining a model to predict qualitative data (discrete categories, such as 'yes' or 'no') is often referred to as classification.

Developing models for statistical learning problems involving longitudinal data, in which a time series of observations are collected over a period of time, poses several challenges, including those associated with collecting the data efficiently and accurately. Analysis of the data may also be problematic, in particular, for a class of problems where variables associated with time-varying phenomena that have discrete events or epochs, each epoch having a characteristic onset time (henceforth referred to as a temporal onset), are sought. For example, in such problems there may be limited data and a plurality of potential variables to be screened. The analysis, therefore, may be underdetermined. In addition, the potential variables may not be independent from one another and/or samples of the potential variables may not have a corresponding probability distribution (for example, a normal distribution).

There is a need, therefore, for an analysis technique to address the challenges described above and to determine variables associated with time-varying phenomena having discrete epochs.

SUMMARY OF THE INVENTION

An apparatus, and related method, for determining one or more association variables is described. The apparatus may include at least one processor, at least one memory, and at least one program module. The program module may be stored in the memory and may be configurable to be executed by the processor. The program module may include instructions for determining a first statistical relationship between one or more temporal onsets corresponding to one or more events and a pattern of occurrence of a compound variable. The compound variable may correspond at least to a pattern of occurrence of a first variable and a pattern of occurrence of a second variable. The determining may include contributions from presence and absence information in the pattern of occurrence of the compound variable.

In some embodiments, the compound variable may correspond at least to a pattern of occurrence of a first variable during a first set of time intervals and a pattern of occurrence of a second variable during a second set of time intervals. Each time interval in a respective set of time intervals may precede a respective temporal onset in the one or more temporal onsets.

The program module may include instructions for identifying the first variable and the second variable as the association variables in accordance with the first statistical relationship. The program module may include instructions for receiving information including the one or more temporal onsets corresponding to one or more events and the pattern of occurrence of the compound variable. The program module may include instructions for providing recommendations to one or more individuals in accordance with the first variable and the second variable.

The program module may include instructions for generating a plurality of compound variables and for determining one or more statistical relationships for the plurality of compound variables. A respective compound variable in the plurality of compound variables may correspond to patterns of occurrence of at least two variables in a set of variables, one of at least the two variables occurring during one set of time intervals and another of at least the two variables occurring during another set of time interval. Each time interval in a respective set of time intervals may precede a respective temporal onset in the one or more temporal onsets. The program module may include instructions for ranking the plurality of compound variables in accordance with the one or more statistical relationships. The program module may include instructions for ranking variables in the set of variables in accordance with a number of occurrences of the variables in the compound variables having respective statistical relationships that approximately exceed a statistical confidence threshold. The statistical confidence threshold may be selected such that at least a subset of the ranking is approximately stable.

The determining may use a non-parametric statistical analysis technique, including a chi-square analysis technique, a log-likelihood ratio analysis technique and/or a Fisher's exact probability analysis technique. The determining may use a supervised learning technique, including a support vector machines (SVM) analysis technique and/or a classification and regression tree (CART) analysis technique.

The pattern of occurrence of the first variable and the pattern of occurrence of the second variable may comprise categorical data. A respective entry in the pattern of occurrence of the compound variable may be determined by performing a logical operation on corresponding entries in the pattern of occurrence of the first variable and the pattern of occurrence of the second variable. In some embodiments, the logical operation is a Boolean operation, including AND, OR, NOT and/or XOR.

Time intervals in the first set of time intervals and/or in the second set of time intervals may be offset in time from the one or more temporal onsets. Time intervals in the first set of time intervals may be different than time intervals in the second set of time intervals. The pattern of occurrence of the first variable and the pattern of occurrence of the second variable may include presence and absence information. A respective entry in a pattern of occurrence of a respective variable may be considered present if the respective entry approximately exceeds at least one threshold. In some embodiments, the one or more statistical relationships may at least in part be determined using a filter, such as an analog filter and/or a digital filter.

In some embodiments, the association variables are migraine triggers and the one or more events correspond to one or more migraines experienced by at least one individual. One or more of the migraine triggers may at least in part induce a migraine in at least the one individual if at least the one individual is exposed to one or more of the migraine triggers.

In some embodiments, the one or more events correspond to an episodic increase in a severity of one or more symptoms associated with a disease and the association variables may trigger the one or more events. The disease may include a form of arthritis, rheumatoid arthritis, joint disease, an auto-immune disorder, an immune-related disorder, an inflammatory disease, lupus, thyroid disease, gout, diabetes, chronic fatigue syndrome, insomnia, depression, a psychological disease, gastrointestinal disease, colitis, ulcerative colitis, inflammatory bowel disease, Crohn's disease, candida, celiac disease, irritable bowel syndrome, one or more food allergies, one or more food sensitivities, morning sickness, menstrual cramps, chronic pain, back pain, facial pain, fibromyalgia, asthma, migraines, abdominal migraines, cyclic vomiting syndrome, cluster headaches, chronic headaches, tension headaches, another type of headache, seizures, epilepsy, neurodermatitis, acne, psoriasis, adiposity, hypertonia, heart disease, hypertension, cardiovascular disease, arteriosclerosis, a form of cancer and/or acquired immune deficiency syndrome.

In another embodiment, an apparatus, and related method, for determining one or more association variables is described. The apparatus may include at least one processor, at least one memory, and at least one program module. The program module may be stored in the memory and may be configurable to be executed by the processor. The program module may include instructions for determining a second statistical relationship between a first subset of temporal onsets in a set of temporal onsets and a pattern of occurrence of at least a third variable during at least a third set of time intervals. Each time interval in the third set of time intervals may precede a respective temporal onset in the first subset of temporal onsets. The program module may also include instructions for identifying at least the third variable as the one or more association variables in accordance with the second statistical relationship. The first subset of temporal onsets may include one or more onsets corresponding to one or more migraines experienced by at least the one individual. The set of temporal onsets may include the first subset of temporal onsets and one or more temporal onsets corresponding to one or more additional headaches experienced by at least the one individual.

The one or more additional headaches may include one or more rebound migraines, one or more recurrence migraines and/or one or more tension headaches. The determining may include contributions from presence and absence information in the pattern or occurrence of the third variable.

The pattern of occurrence of the third variable may include one or more entries corresponding to at least a fourth time interval after at least a respective temporal onset in the first subset of temporal onsets. A respective migraine corresponding to at least the respective temporal onset may have a duration including at least the fourth time interval. The one or more entries may be excluded when the second statistical relationship is determined.

In another embodiment, an apparatus, and related method, for determining migraine triggers is described. The apparatus may include at least one processor, at least one memory, and at least one program module. The program module may be stored in the memory and may be configurable to be executed by the processor. The program module may include instructions for determining a second subset of the migraine triggers for at least the one individual. The program module may also include instructions for associating at least the one individual with one or more groups of migraine triggers in accordance with the determined second subset of migraine triggers.

In another embodiment, a process for determining one or more association variables is described. A first data stream, including one or more temporal onsets corresponding to one or more events, the pattern of occurrence of the first variable and the pattern of occurrence of the second variable, may be transmitted. A second data stream, including information that identifies the first variable and the second variables as the association variables, may be received. The information may be determined in accordance with the first statistical relationship between the one or more temporal onsets and the pattern of occurrence of the compound variable. The compound variable may correspond at least to the pattern of occurrence of the first variable and the pattern of occurrence of the second variable. The first statistical relationship may include contributions from presence and absence information in the pattern of occurrence of the compound variable.

The disclosed embodiments reduce or eliminate the problems described above and provide an analysis technique to determine association variables associated with time-varying phenomena having discrete epochs.

BRIEF DESCRIPTION OF THE DRAWINGS

Additional objects and features of the invention will be more readily apparent from the following detailed description and appended claims when taken in conjunction with the drawings.

FIG. 1A is a block diagram illustrating an existing unsupervised learning technique.

FIG. 1B is a block diagram illustrating an existing supervised learning technique.

Like reference numerals refer to corresponding parts throughout the several views of the drawings.

DETAILED DESCRIPTION

Figure 2:
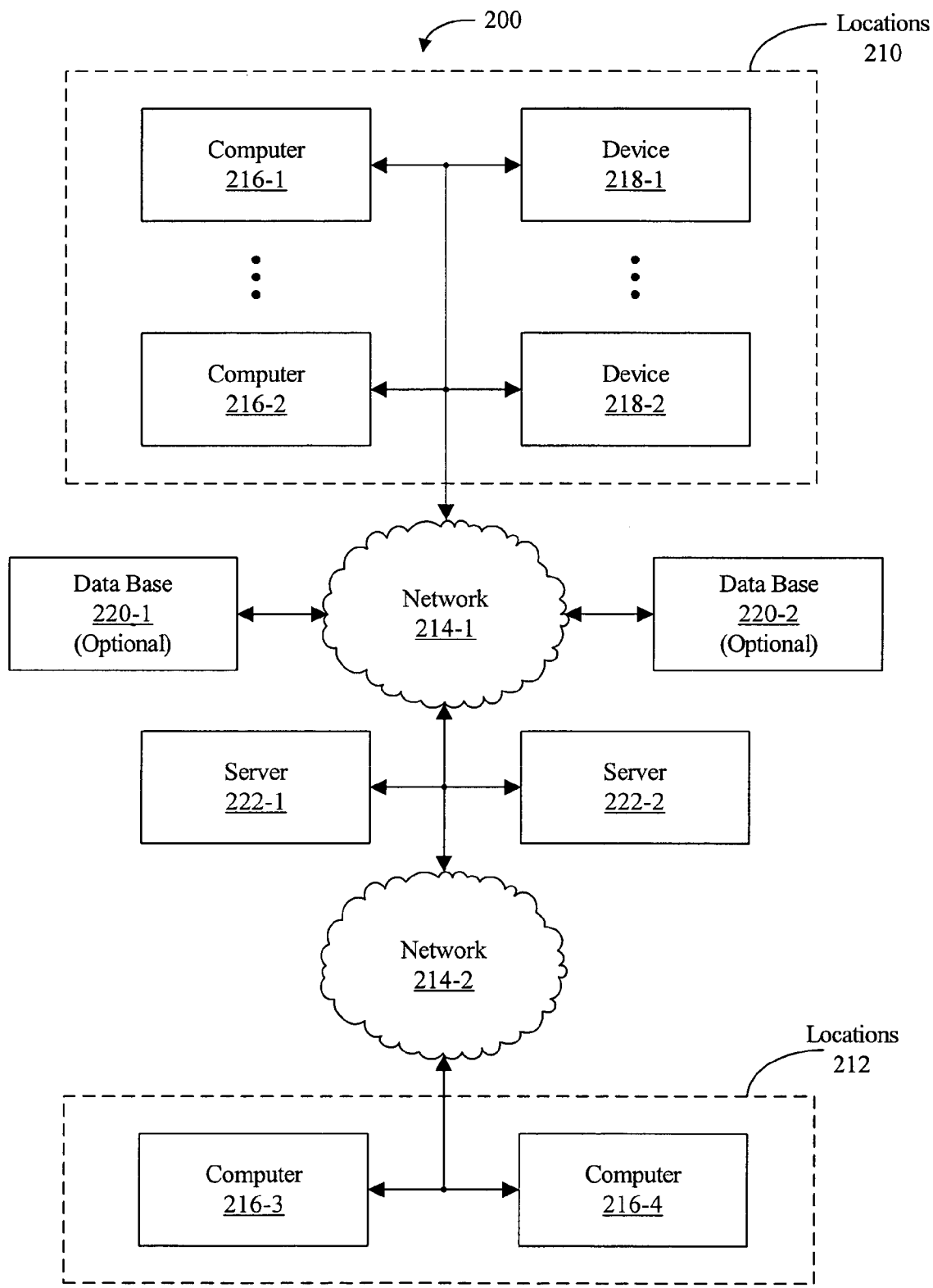
FIG. 2 is a block diagram illustrating an embodiment of a system for collecting and analyzing data, and for providing recommendations.

Reference will now be made in detail to embodiments, examples of which are illustrated in the accompanying drawings. In the following detailed description, numerous specific details are set forth in order to provide a thorough understanding of the present invention. However, it will be apparent to one of ordinary skill in the art that the present invention may be practiced without these specific details. In other instances, well-known methods, procedures, components, and circuits have not been described in detail so as not to unnecessarily obscure aspects of the embodiments.

Embodiments of one or more apparatuses, and related methods, for collecting information and determining one or more association variables are described. The information may be collected by asking a subset of pre-determined questions in a set of pre-determined questions one or more time during a data-collection time interval using the one or more apparatuses.

The subset of pre-determined questions may be varied during the data-collection time interval in accordance with configuration instructions received by the one or more apparatuses. In some embodiments, the configuration instructions correspond to non-executable instructions. The configuration instructions may be transmitted to the one or more apparatuses and answers to a subset of the pre-determined questions, selected in accordance with the configuration instructions, may be received from the one or more apparatuses using SMS messages and/or email messages.

The subset of pre-determined questions may include pre-selected answers that may be displayed for each question in at least a plurality of pre-determined questions in the subset of pre-determined questions. Answering a respective pre-determined question may only involve selection if the respective answer to the respective pre-determined question is different than the respective pre-selected answer. The pre-selected answers may be selected in accordance with an answer history for one or more individuals and/or one or more groups of individuals. In some embodiments, the pre-selected answers may correspond to one or more default answers.

In some embodiments, at least one apparatus or device, such as a personal digital assistant, a tablet computer, a Blackberry, a cellular telephone, and/or a hand-held computer, containing the set of pre-determined questions may be provided to at least one individual. In some embodiments, at least the one individual may be provided a memory card (such as a smart card, a subscriber identity module or SIMS card, and/or a card having ROM, FLASH or other memory) containing the set of pre-determined questions. In some embodiments, at least one server may transmit instructions corresponding to the subset of pre-determined questions to at least one computer. A browser in at least the one computer may render the instructions corresponding to the subset of pre-determined questions. Communication with apparatuses, devices, computers, and/or servers may occur via a network, such as the Internet (also known as the World Wide Web), an Intranet, a local area network (LAN), a wide area network (WAN), a metropolitan area network (MAN), and/or a wireless network.

The one or more association variables may be determined and/or identified, using one or more apparatuses, and/or the related methods, in accordance with one or more statistical relationships between one or more temporal onsets corresponding to one or more events and patterns of occurrence of one or more variables and/or one or more compound variables. The one or more compound variables may be determined using one or more variables in a set of variables. The one or more temporal onsets may include one or more onset times and/or one or more onsets during one or more time intervals.

A respective compound variable may correspond at least to a pattern of occurrence of a first variable during a first time interval preceding the one or more temporal onsets and a pattern of occurrence of a second variable during a second time interval preceding the one or more temporal onsets. The first time interval and/or the second time interval may be offset in time from the one or more temporal onsets. The first time interval may be different than the second time interval. In some embodiments, the respective compound variable may correspond to patterns of occurrence of three of more variables during corresponding time intervals preceding the one or more temporal onsets.

Contributions from presence and absence information in the pattern of occurrence of the one or more compound variables may be included when determining the one or more statistical relationships. The pattern of occurrence for the respective compound variable, such as the pattern of occurrence of the first variable and the pattern of occurrence of the second variable, may include presence and absence information.

The one or more statistical relationships may be determined using a non-parametric analysis technique (which makes few assumptions about an existence of a probability distribution function, such as a normal distribution, corresponding to a population from which samples are obtained, or regarding independence of the variables and/or the compound variables) and/or a supervised learning analysis technique. The analysis may perform hypothesis testing to determine if the one or more temporal onsets and the one or more compound variables and/or one or more variables are statistically independent (or dependent) in accordance with a statistical significance criterion. In the process, the analysis may increase an effective signal-to-noise ratio in an underdetermined problem (i.e., sparse sampling in a multi-dimensional variable space) by restricting a number of local fitting neighborhoods (i.e., a number of relevant variables and/or compound variables).

The one or more compound variables may be ranked in accordance with the one or more statistical relationships. The variables in the set of variables may be ranked in accordance with a number of occurrences of the variables in the compound variables having respective statistical relationships that approximately exceed the statistical confidence threshold corresponding to a noise floor. The statistical confidence threshold may be selected such that at least a subset of the ranking is approximately stable.

One or more variables in the one or more compound variables, such as the first variable and the second variable, may be identified as the one or more association variables. Additional association variables may be identified by associating the one or more association variables with one or more groups of association variables, including pre-determined groups of association variables. One or more recommendations may be provided to at least the one individual in accordance with the one or more association variables. In some embodiments, at least the one individual may be a healthcare provider (such as a physician, nurse, chiropractor, and/or an associated staff member), a parent, a guardian, and/or an individual that has a disease. The one or more recommendations may be included in one or more reports.

The one or more association variables may, at least in part, trigger, initiate, and/or precipitate the one or more events (henceforth referred to as trigger). The one or more association variables may directly or indirectly cause the one or more events. Alternatively, the one or more association variables may not directly or indirectly cause the one or more events. The one or more association variables may enable the one or more events. To make an analogy, in some embodiments the one or more association variables may function as keys in one or more locks (receptors), allowing a spring-loaded door (corresponding, for example, to a biochemical predisposition) to open. Two or more association variables may work in conjunction with one another, i.e., at least the one individual may experience at least one event if at least the one individual is exposed to two or more association variables in close temporal proximity, in a temporal sequence and/or in an ordered temporal sequence (i.e., a particular pattern of exposure to two or more association variables). An effect of the association variables may be cumulative. Exposure to a sufficient quantity of the respective association variable may trigger the one or more events, or exposure to quantities of two or more association variables may trigger the one or more events. Be it cumulative and/or cooperative, the respective association variable may correspond to 5%, 10% 25%, 50% or more of a total trigger for the one or more events. The one or more association variables may be specific to an individual and/or a group of two or more individuals. In some embodiments, the one or more events may correspond to an episodic increase in a severity of one or more symptoms associated with a disease, such as a chronic disease, and/or a disease condition in at least the one individual.

The disease may include a form of arthritis, rheumatoid arthritis, joint disease, an auto-immune disorder, an immune-related disorder, an inflammatory disease, lupus, thyroid disease, gout, diabetes, chronic fatigue syndrome, insomnia, depression, a psychological disease, gastrointestinal disease, colitis, ulcerative colitis, inflammatory bowel disease, Crohn's disease, candida, celiac disease, irritable bowel syndrome, one or more food allergies, one or more food sensitivities, morning sickness, menstrual cramps, chronic pain, back pain, facial pain, fibromyalgia, asthma, migraines, abdominal migraines, cyclic vomiting syndrome, cluster headaches, chronic headaches, tension headaches, another type of headaches, seizures, epilepsy, neurodermatitis, acne, psoriasis, adiposity, hypertonia, heart disease, hypertension, cardiovascular disease, arteriosclerosis, a form of cancer, and/or acquired immune deficiency syndrome. The system and method may also be applied to patients have multiple illnesses, such a geriatric patients.

The embodiments of the apparatuses, and related methods, may be used to collect and analyze information associated with time-varying phenomena having discrete epochs. The embodiments of the apparatuses, and related methods, may also be used to identify one or more association variables for such time-varying phenomena, thereby allowing remedial action to be taken (if appropriate). Technical effects for the embodiments of the apparatuses, and related methods, may include displaying one or more questionnaires, including a plurality of pre-selected answers, on at least one display, transmitting and receiving collected information using a network, determining one or more statistical relationships in at least one apparatus, identifying one or more association variables in at least the one apparatus, transmitting and receiving one or more recommendations and/or one or more reports using the network, and/or displaying the one or more recommendations and/or the one or more reports on at least one display.

The embodiments of the apparatuses, and related methods, may allow collected data or information to be converted into actionable information, such as one or more recommendations. In some embodiments, providing the recommendations to one or more healthcare providers and/or at least the one individual that has the disease may help convert this information into knowledge. The healthcare providers, who practice medicine, may use the knowledge to aid the one or more individuals that have the disease, including prescribing one or more diagnostic tests and/or one or more treatment modalities. In the hands of at least the one individual that has the disease, the information may motivate behavior modification that may mitigate or reduce a severity and/or frequency of one or more symptoms associated with the disease.

Attention is now directed towards embodiments of apparatuses, devices, computers, servers, and systems that may be used to implement the collection of information, the statistical analysis and/or the providing of recommendations. FIG. 2 is a block diagram illustrating an embodiment of a system 200 for collecting data or information, analyzing the information, and/or for providing recommendations (for example, in one or more reports). A network 214 couples servers 222 and optional databases 220 (located in one or more additional computers, servers, and/or network attached storage devices) to first locations 210 and second locations 212. The network 214 may include the Internet (also known as the World Wide Web), an Intranet, a local area network (LAN), a wide area network (WAN), a metropolitan area network (MAN), and/or a wireless network (including one or more cellular telephone networks, Bluetooth networks, Wi-MAX networks, and/or Wi-Fi networks using IEEE 802.11a, 802.11b, 802.11g and/or 802.11n).

The first locations 210 may correspond to one or more individuals or humans beings. In some embodiments, the one or more individuals may have been diagnosed as having the disease. At least one of the one or more individuals (henceforth referred to as a first individual) may interact with at least one of computers 216 and devices 218. The devices 218 may include one or more personal digital assistants, one or more tablet computers, one or more cellular telephones, one or more hand-held computers, and/or a combination of two or more of these items. One or more of the servers 222 may provide the subset of pre-determined questions one or more times during the data-collection time interval. Pre-determined questions may include questions that are determined prior to the beginning of the data-collection time interval. In some embodiments, the pre-determined questions may be generated for at least the first individual prior to the beginning of the data-collection time interval, for example, in accordance with an optional initial survey. In exemplary embodiments, the data-collection time interval may be approximately a fraction of a day (such as 1, 3, 4 or 6 hours), a day, several days, a week, a month, 2 months, 3 months, 4 months, 6 months, 9 months, a year, several years, and/or a combination of one or more of these items.

In some embodiments, one or more of the servers 222 may provide instructions for a web page corresponding to the subset of pre-determined questions which are rendered in a browser. The instructions for the web page may include embedded JavaScript instructions that may be executed by one or more of the computers 216 and/or devices 218. In some embodiments, one or more of the computers 216 and/or devices 218 may already contain the subset of pre-determined questions or the set of pre-determined questions. Configuration instructions, which may be non-executable, from the one or more servers 222 may select the subset of pre-determined questions. In other embodiments, at least the first individual may be asked one or more questions that are not pre-determined, such as one or more questions that may be dynamically generated in one or more of the servers 222. Such dynamically generated questions may be provided approximately in real-time during the data-collection time interval.

At least the first individual may provide answers to the subset of pre-determined questions one or more times during the data-collection time interval. The answers may be transmitted to one or more of the servers 222 and/or one or more of the optional databases 220. In some embodiments, the answers are transmitted at least in part using email messages and/or SMS messages, or only using email messages and/or SMS messages. The email messages and/or SMS messages may be encrypted. One or more of the servers 222, in conjunction with information stored in one or more of the optional databases 220, may analyze the answers to determine one or more statistical relations, the ranking of the variables, and/or to identify the one or more association variables. One or more of the servers 222 may revise the subset of pre-determined questions that are provided and/or provide revised configuration instructions, which may be non-executable, to at least one of the computers 216 and devices 218 in order to modify the subset of pre-determined questions for at least the first individual. In some embodiments, the configuration instructions may be provided at least in part using email messages and/or SMS messages, or only using email messages and/or SMS messages. The email messages and/or SMS messages may be encrypted. The configuration instructions may be determined in accordance with the answer history for at least a subset of the one or more individuals, one or more groups of individuals, and/or default answers to the subset of pre-determined questions that may be stored in at least one of the optional databases 220.

The second locations 212 may correspond to one or more healthcare providers (such as a physician, nurse, chiropractor, and/or an associated staff member), one or more parents, one or more guardians, and/or one or more additional individuals that have the disease (henceforth referred to as a second individual). In some embodiments, one or more of the servers 222, in conjunction with information stored in one or more of the optional databases 220, may provide one or more recommendations in accordance with the one or more determined association variables to at least the second individual. In some embodiments, one or more of the servers 222, in conjunction with information stored in one or more of the optional databases 220, may provide the one or more recommendations in accordance with the one or more determined association variables to at least the first individual at one or more of the first locations 210. The one or more recommendations may be in the form of one or more reports or documents; including soft or hard copies. In some embodiments, the recommendations may be provided by transmitting a data stream including the recommendations and/or transmitting a data stream including instructions corresponding to the recommendations (for example, the instructions may correspond to one or more web-pages) by email, SMS, and/or by regular mail.

In other embodiments, at least the first individual may be asked one or more questions that are provided by at least the second individual. Such questions from at least the second individual may be dynamically generated and may be provided approximately in real-time during the data-collection time interval. Answers to these and/or other dynamically generated questions (such as those that may be provided by the one or more servers 222) may be provided to at least the second individual and/or one or more servers 222 approximately in real-time or after a time delay. In some embodiment, at least the second individual may provide feedback and/or instructions to one or more of the servers 222 that is based on the one or more recommendations. In some embodiments, the feedback and/or instructions may be used to revise the configuration instructions. In some embodiments, the feedback and/or instructions may be used to determine one or more additional pre-determined questions that are provided to at least the first individual.

While the system 200 has been shown with two computers 216 and two devices 218 at the first locations 210, and two computers 216 at the second locations 212, there may be fewer or additional computers 216 and/or devices 218. In addition, one or more individuals at the first locations 210 and/or the second locations 212 may share a computer, a device, a set of computers, and/or a set of devices. Similarly, there may be fewer or more servers 222 and/or optional databases 220. One or more functions of one or more of the computers 216, devices 218, servers 222, and/or optional databases 220 may be combined into a single item in the system 200 and/or may be performed at one or more remote locations in the system 200. One or more positions of one or more items in the system 200 may be changed. In some embodiments, the functions of the one or more servers 222 and/or optional databases 220 may be performed in one or more of the computers 216 and/or one or more of the devices 218, for example, using one or more applications programs or modules installed on one or more of the computers 216 or in one or more removable storage media in one or more of the computers 216. In some embodiments, the one or more applications programs or modules installed on one or more of the computers 216 or in one or more removable storage media in one or more of the computers 216 may be dedicated or stand-alone applications that function without interactions with one of the servers 222 or only occasionally interact with one or more of the servers 222.

Figure 3:
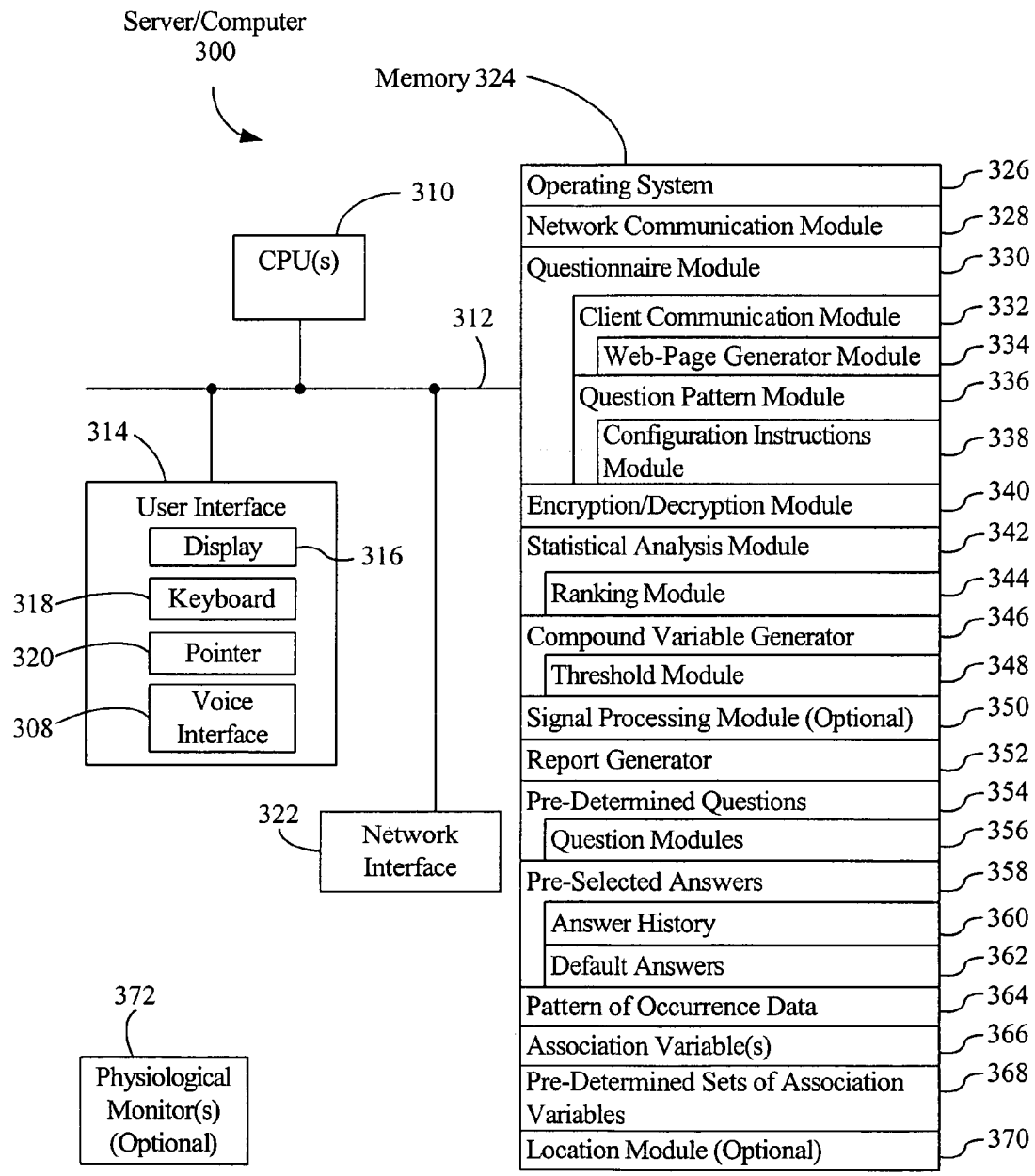
FIG. 3 is a block diagram illustrating an embodiment of a server or computer.

FIG. 3 is a block diagram illustrating an embodiment of a server or computer 300, such as one of the computers 216 and/or servers 222 in FIG. 2. The server or computer 300 includes one or more processing units (CPUs) 310, at least one network or communications interface 322 for communicating with other computers, servers, devices, and/or databases, a memory device 324 with primary and secondary storage, at least one optional user interface 314, and one or more signal lines 312 for connecting these components. The one or more processing units (CPUs) 310 may support parallel processing and/or multi-threaded operation. The optional user interface 314 may have one or more displays 316, keyboards 318, pointers 320 (such as a mouse), a touchpad (not shown), and/or a voice interface 308, including one or more speakers and/or microphones. The one or more displays 316 may include a touch screen (which may combine at least one of the keyboards 318 with at least one of the displays 316). The one or more signal lines 312 may constitute one or more communication buses. The network or communications interface 322 may have a persistent communication connection.

The memory device 324 may include high speed random access memory and/or non-volatile memory, including ROM, RAM, EPROM, EEPROM, FLASH, one or more smart cards, one or more magnetic disc storage devices, and/or one or more optical storage devices. The memory device 324 may store an operating system 326, such as LINUX, UNIX, OS10, or WINDOWS, that includes procedures (or a set of instructions) for handling various basic system services for performing hardware dependent tasks. The memory device 324 may also store procedures (or a set of instructions) in a network communications module 328. The communication procedures may be used for communicating with one or more computers 216 (FIG. 2), servers 222 (FIG. 2), optional databases 220 (FIG. 2), and/or devices 218 (FIG. 2). The communication procedures may include those for a parallel interface, a serial interface, an infrared interface, Bluetooth, Firewire (IEEE 1394A and/or IEEE 1394B), and/or a USB interface (for example, USB-1 and/or USB-2 or High-Speed USB). The communication procedures may include HyperText Transport Protocol (HTTP) to transport information using the Transmission Control Protocol/Internet Protocol (TCP/IP), as well as a secure or encrypted version of HTTP, such as Hypertext Transport Protocol over Secure Socket Layer (HTTPS), a Layer 2 Tunneling Protocol (L2TP), or another Internet Protocol Security, such as IPSEC.

The memory device 324 may also include the following elements, or a subset or superset of such elements, including a questionnaire module (or a set of instructions) 330, an encryption/decryption module (or a set of instructions) 340 (using, for example, pretty good privacy, symmetric encryption, and/or asymmetric encryption), a statistical analysis module (or a set of instructions) 342, a compound variable generator (or a set of instructions) 346, an optional signal processing module (or a set of instructions) 350, a report generator (or a set of instructions) 352 for formatting and providing recommendations and related information to at least one of the first individual and/or the second individual, pre-determined questions (or a set of instructions) 354, pre-selected answers (or a set of instructions) 358, pattern of occurrence data 364 corresponding to one or more events and/or one or more variables, association variable(s) 366, pre-determined sets of association variables 368, and/or an optional location module (or a set of instructions) 370 for determining a location of one or more computers 216 (FIG. 2) and/or one or more devices 218 (FIG. 2) (for example, using an IP address, a global positioning system, and/or remote localization capability associated with a portable device such as a cellular telephone).

The questionnaire module 330 may include a client communication module (or a set of instructions) 332 and/or a question pattern module (or a set of instructions) 336 for providing the subset of pre-determined questions to at least the first individual. The client communication module 332 may include a web-page generator module (or a set of instructions) 334 that generates instructions corresponding to one or more web pages, including HyperText Mark-up Language (HTML), eXtensible Mark-up Language (XML), Java, JavaScript, Perl, PHP, and/or NET. The question pattern module 330 may include a configuration instructions module (or a set of instructions) 338 for providing instructions that select the subset of pre-determined questions. The statistical analysis module 342 may include a ranking module (or a set of instructions) 344. The compound variable generator 346 may include a threshold module (or a set of instructions) 348 for determining if one or more entries in the pattern of occurrence data 364 for at least one variable correspond to a presence or an absence. The pre-determined questions 354 may include one or more question modules (or a set of instructions) 356. The pre-selected answers 358 may include answer history 360 for one or more individuals and/or one or more groups of individuals, and/or default answers (or a set of instructions) 362.

In some embodiments, the server or computer 300 may communicate with one or more optional physiological monitors 372. Communication may be via a cable (such as USB), infrared, Firewire and/or wireless (such as Wi-Fi or Bluetooth). In an alternate embodiment, at least the first individual may manually enter physiological data from the one or more optional physiological monitors 372 using one of the components in the optional user interface 314. In some embodiments, the physiological data may be entered using a binary search procedure corresponding to a series of questions, such as, "Is the physiological data value less than 0.5?," "Is the physiological data value less than 0.25?," "Is the physiological data value greater than 0.375?," and so on until a desired precision is obtained. (A similar binary search procedure may be used to answer one or more pre-determined questions in the subset of pre-determined questions.) Communication with the one or more optional physiological monitors 372 may be at discrete times or it may be continuous. The one or more optional physiological monitors 372 may include an electroencephalogram monitor (such as a respective Holter monitor), an electrocardiogram monitor (such as the respective Holter monitor), an electromyleogram monitor, an inflammatory response monitor, a respiratory monitor (such as the Air Watch II) of variables such as peak expiratory flow and/or a forced expiratory volume in 1 second, a blood glucose monitor, a blood pressure monitor, a thermometer, a vital sign monitor (such as those for pulse or respiration rate), a galvanometric response monitor, and/or a reflex arc monitor.

Instructions in the modules in the memory device 324 may be implemented in a high-level procedural language, an object-oriented programming language, and/or in an assembly or machine language. The programming language may be complied or interpreted, i.e, configurable or configured to be executed by the one or more processing units 310. In addition, the server or computer 300 may include fewer or additional executable procedures, sub-modules, tables, and/or other data structures (not shown). In some embodiments, additional or different modules and data structures may be used and some of the modules and/or data structures listed above may not be used. In some embodiments, the functions of two or more modules may be combined in a single module. In some embodiments, implementation of functionality of the server or computer 300 may be implemented more in hardware and less in software, or less in hardware and more in software, as is known in the art.

Although the server or computer 300 is illustrated as having a number of discrete items, FIG. 3 is intended more as a functional description of the various features which may be present in the server or computer 300 rather than as a structural schematic of the embodiments described herein. In practice, and as recognized by those of ordinary skill in the art, the functions of the server or computer 300 may be distributed over a large number of servers or computers, with various groups of the servers or computers performing particular subsets of the functions. Items shown separately in the server or computer 300 may be combined, some items may be separated and/or additional items may be added. The apparatuses and methods disclosed may be implemented in hardware and/or software. In alternate embodiments, some or all of the functionality of the server or computer 300 may be implemented in one or more application specific integrated circuits (ASICs) and/or one or more digital signal processors (DSPs).

Figure 4:
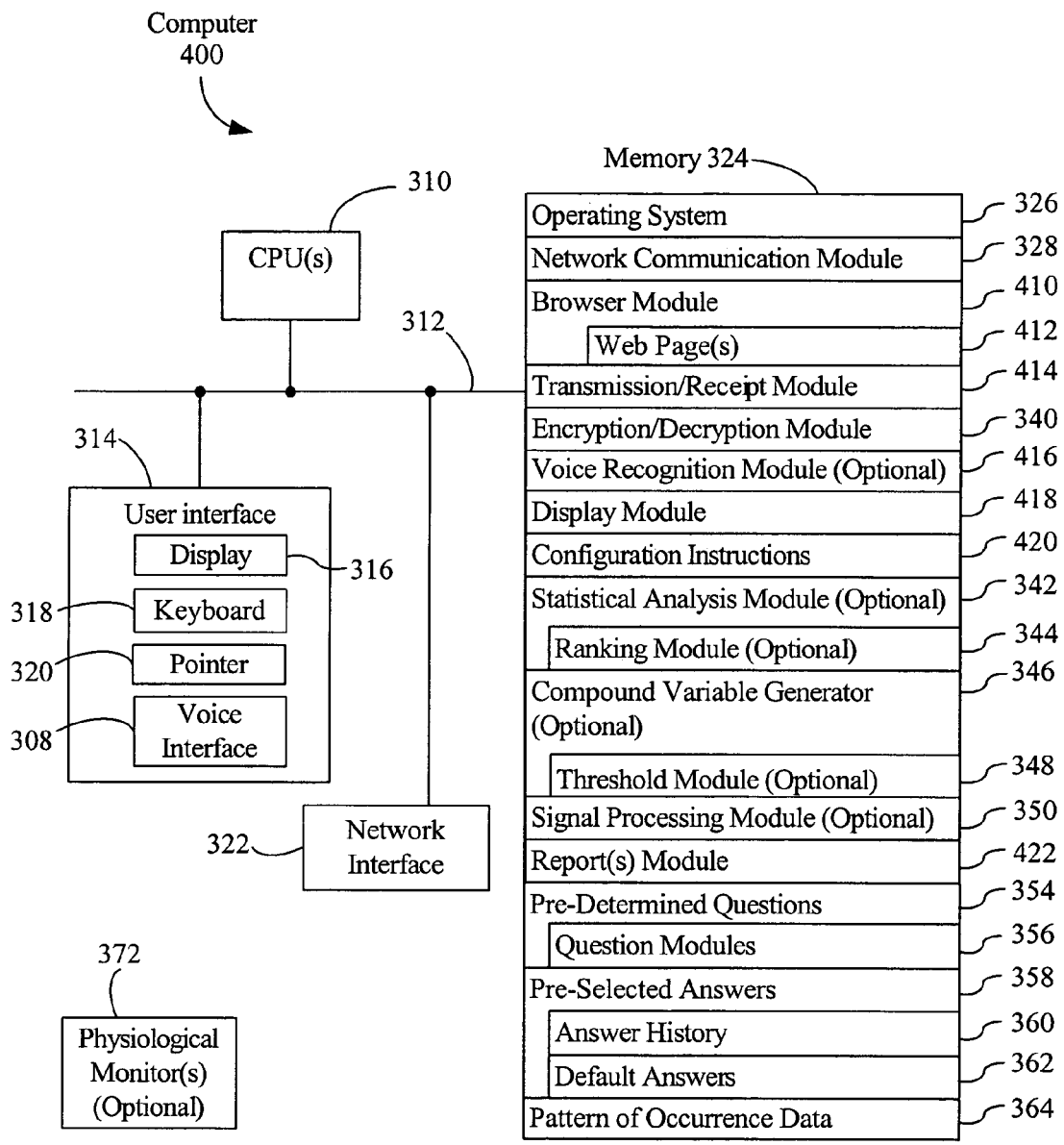
FIG. 4 is a block diagram illustrating an embodiment of a computer.

FIG. 4 is a block diagram illustrating an embodiment of a computer 400, such as one of the computers 216 (FIG. 2). The memory device 324 may include a browser module (or a set of instructions) 410 for rendering web-page instructions, a transmission/receipt module (or a set of instructions) 414 for handling information such the subset of pre-determined questions and corresponding answers, an optional voice recognition module (or a set of instructions) 416, a display module (or a set of instructions) 418 for displaying the subset of pre-determined questions and/or the pre-selected answers to at least the first individual, configuration instructions 420, and/or a report(s) module (or a set of instructions) 422 for formatting and presenting recommendations and related information to at least one of the first individual or the second individual. The browser module 410 may include instructions corresponding to one or more web pages 412. The computer 400 may optionally perform at least a portion of the analysis, such as the determining at least some of the statistical relationships. The computer 400 may store pattern of occurrence data 364 corresponding to one or more events and/or one or more variables. The pattern of occurrence data 364 may be stored temporarily as the subset of pre-determined questions are answered over at least a portion of the data-collection time interval. For example, answers for a respective day may be transmitted at night. In some embodiments, the pattern of occurrence data 364 may be communicated to one or more of the servers 222 (FIG. 2) and/or optional databases 220 (FIG. 2) approximately in real-time, for example, as respective pre-determined questions are answered. In some embodiments, the computer 400 may communicate with one or more optional physiological monitors 372.

Although the computer 400 is illustrated as having a number of discrete items, FIG. 4 is intended more as a functional description of the various features which may be present in the server or computer 400 rather than as a structural schematic of the embodiments described herein. In practice, and as recognized by those of ordinary skill in the art, the functions of the server or computer 400 may be distributed over a large number of servers or computers, with various groups of the servers or computers performing particular subsets of the functions. Items shown separately in the computer 400 may be combined, some items may be separated and/or additional items may be added. The apparatuses and methods disclosed may be implemented in hardware and/or software. In alternate embodiments, some or all of the functionality of the server or computer 400 may be implemented in one or more ASICs and/or one or more DSPs.

Figure 5:
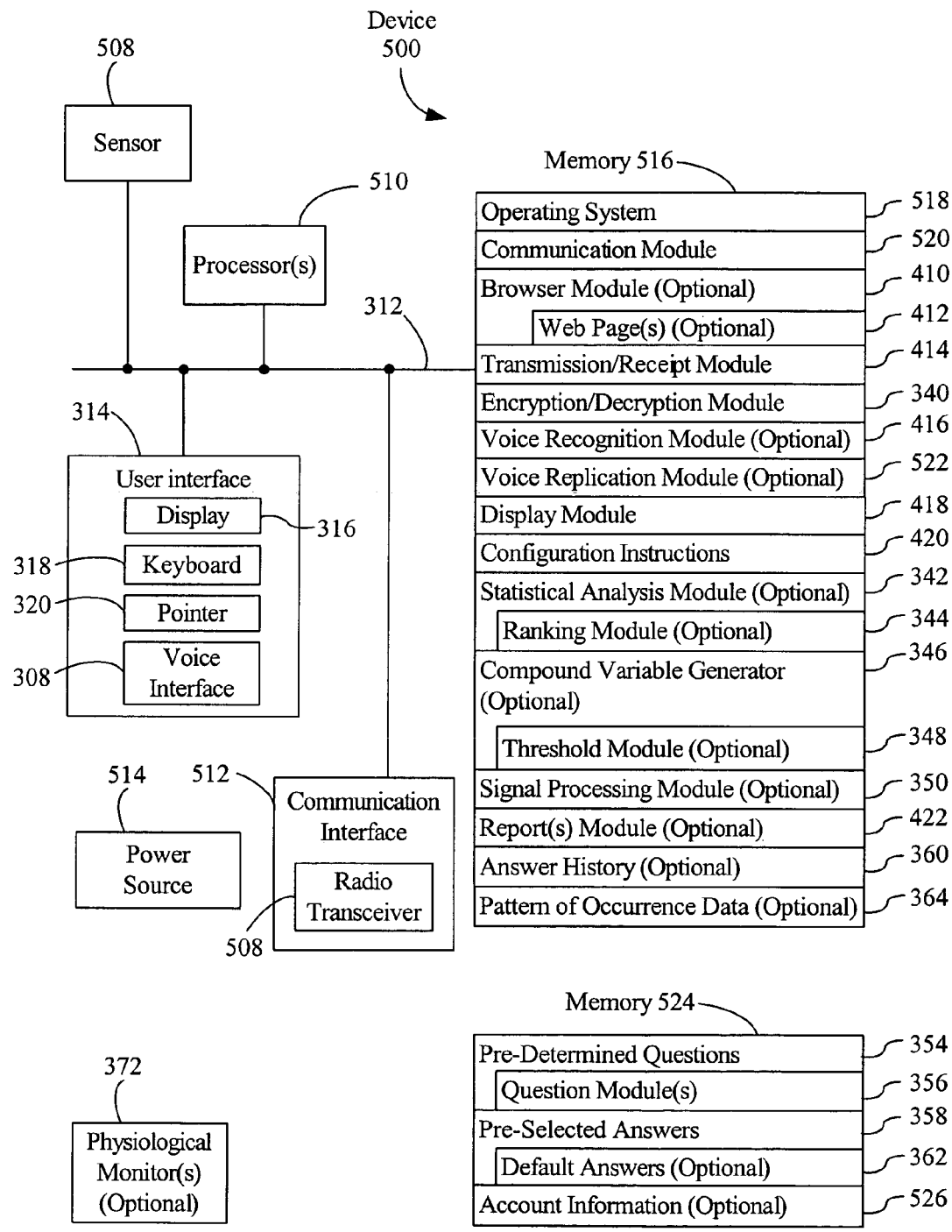
FIG. 5 is a block diagram illustrating an embodiment of a device.

FIG. 5 is a block diagram illustrating an embodiment of a device 500, such as one of the devices 218 (FIG. 2). The device 500 may include a cellular telephone, a personal digital assistant, a tablet computer, a Blackberry, a hand-held computer, and/or a combination of two or more of these items. In some embodiments, the device 500 may be an implantable medical device that collects and communicates data for at least the first individual. The device 500 may include one or more data processors, video processors and/or processors 510, at least one communications interface 512 for communicating with other computers, servers, devices and/or databases, a first memory device 516 with primary and/or secondary storage, a second optional memory device 524 that may be removable, at least the one user interface 314, a sensor 508, and one or more signal lines 312 for connecting these components. The one or more data processors, video processors and/or processors 510 may support parallel processing and/or multi-threaded operation. The user interface may have one or more displays 316, keyboards 318, pointers 320 (such as a mouse or a stylus), a touchpad (not shown), and/or a voice interface 308 including one or more speakers and/or microphones. The one or more displays 316 may include a touch screen (which may combine at least one of the keyboards 318 with at least one of the displays 316). The one or more signal lines 312 may constitute one or more communication buses. The communications interface 512 may include a radio transceiver 508 for converting signals from baseband to one or more carrier bands and/or from one or more carrier bands to baseband. The communications interface 512 may have a persistent communication connection. The device 500 may include a power source 514, such as a battery or a rechargeable battery, for supplying power to one or more of these components. The sensor 508 may be an imaging element, such as CCD array, for capturing one or more images (such as pictures).

The memory device 516 may include high speed random access memory and/or non-volatile memory, including ROM, RAM, EPROM, EEPROM, FLASH, one or more smart cards, one or more magnetic disc storage devices, and/or one or more optical storage devices. The memory device 516 may store an embedded operating system 518, such as LINUX, UNIX, OS10, PALM or WINDOWS, or a real-time operating system (such as VxWorks by Wind River System, Inc.) suitable for use in industrial or commercial devices. The operating system 518 may includes procedures (or a set of instructions) for handling various basic system services for performing hardware dependent tasks, including password and/or biometric security authentication. The memory device 516 may also store procedures (or a set of instructions) in a communications module 520.

The communication procedures in the communications module 520 may be used for communicating with one or more computers 216 (FIG. 2), servers 222 (FIG. 2), optional databases 220 (FIG. 2), and/or devices 218 (FIG. 2). The communication procedures may include those for a parallel interface, a serial interface, an infrared interface, Bluetooth, Firewire (IEEE 1394A and/or IEEE 1394B), and/or a USB interface (for example, USB-1 and/or USB-2 or High-Speed USB). The communication procedures may include one or more protocols corresponding to a Global System for Mobile Telecommunications (GSM), Code Division Multiple Access (CDMA), a Short Message Service (SMS), an Enhanced Messaging Service (EMS), a Multi-media Message Service (MMS), a General Packet Radio Service (GPRS), a Wireless Application Protocol (WAP), instant messaging, email, TCP/IP, and/or a voice over internet protocol (VoIP). Note that SMS supports communication of up to 160 characters using, for example, text messaging. Email may utilize an email address corresponding to a subscriber's 10-digit telephone number, such as 1234567890@messaging.carrier.com, where 'carrier' may be a cellular telephone provider such as Cingular. EMS includes text formatting, and supports communication of simple black and white images, as well as sound tones. MMS supports communication of a wide variety of media from text to video.

The memory device 516 may also include the following elements, or a subset or superset of such elements, including the optional browser module (or a set of instructions) 410, the transmission/receipt module (or a set of instructions) 414, the encryption/decryption module (or a set of instructions) 340, the optional voice recognition module (or a set of instructions) 416, an optional voice replication module (or a set of instructions) 522 for asking at least some of the subset of pre-determined questions using the voice interface 308, the display module (or a set of instructions) 418, the configuration instructions 420, the optional statistical analysis module (or a set of instructions) 342, the optional compound variable generator (or a set of instructions) 346, the optional signal processing module (or a set of instructions) 350, the optional report(s) module (or a set of instructions) 422, the optional answer history 360, and/or the optional pattern of occurrence data 364.

The optional browser module 410 may include instructions corresponding to one or more web pages 412. The optional statistical analysis module 342 may include the optional ranking module (or a set of instructions) 344. The optional compound variable module 346 may include the optional threshold module (or a set of instructions) 348. The device 500 may optionally perform at least a portion of the analysis, such as determining at least some of the statistical relationships. The encryption/decryption module 340 may include encryption/decryption that is supported in the GSM and/or CDMA protocols. In some embodiments, the encryption/decryption module 340 may include a virtual private network (VPN) tunneling application.

The optional pattern of occurrence data 364 may be stored temporarily as the subset of pre-determined questions are answered over at least a portion of the data-collection time interval. For example, answers for a respective day may be transmitted at night. In some embodiments, the optional pattern of occurrence data 364 may be communicated to one or more of the servers 222 (FIG. 2) and/or optional databases 220 (FIG. 2) approximately in real-time, for example, as respective pre-determined questions are answered.

In an exemplary embodiment, the configuration instructions 420 and the answers to the subset of pre-determined questions may be communicating using one or more SMS text messages and/or email messages. In some embodiments, only SMS text messages and/or email messages are used. The use of SMS text messaging and/or email messaging may result in cost savings associated with establishing accounts and/or with the communication. Receipt of a respective SMS text message by an end destination, such as one of the servers 222 (FIG. 2), may be confirmed using a handshake message (such as another SMS message). Upon receipt of such a handshake message, the device 500 may erase and/or delete information that was transmitted in the original SMS text message (such as one or more answers to the subset of pre-determined questions or at least a portion of the optional pattern of occurrence data 364).

In some embodiments, at least the first individual may use the device 500 to collect information that may be subsequently used to answer one or more of the subset of pre-determined questions. For example, the sensor 508 may be used to take a picture of a menu, a table of contents, and/or one or more medicines consumed. Or an audio file listing items consumed during a meal or snack may be recorded. The collected information may be processing in the device 500, or in one or more remote computers and/or one or more servers, using image processing, text recovery/identification, and/or speech recognition (using, for example, the optional voice recognition module 416. In some embodiments, the device 500 may communicate with one or more optional physiological monitors 372.

In some embodiments, the device 500 may provide at least the first individual with at least one reminder (such as a reminder to take a medicine at a respective time) using one or more messages transmitted to the device 500 and/or using one or more pre-stored messages in the device 500 that may be enabled by the configuration instructions 420. At least the one reminder may be provided using the voice replication module 522 and the voice interface 308.

The optional memory device 524 may include one or more FLASH drives, ROMs, memory sticks, optical storage media (such as rewritable or ROM CDs and/or DVDs), smart cards, SIMS cards, secure digital (SD) cards (compatible with devices that use a PALM embedded operating system), multimedia cards (MMCs), magnetic disc storage devices (such as disc drives), and/or magnetic media (such as floppy discs). The optional memory device 524 may also include the following elements, or a subset or superset of such elements, including the pre-determined questions (or a set of instructions) 354, the pre-selected answers 358 (or a set of instructions), and/or the optional account information 526. The pre-determined questions 354 may include the one or more question modules (or a set of instructions) 356. The pre-selected answers 358 may include optional default answers (or a set of instructions) 362. The optional account information 526 may include at least one carrier account number (for an Internet service provider, a cellular telephone provider, and/or a wireless services provider) and/or at least one telephone number that may enable at least the first individual to receive the configuration instructions 420 and to transmit the answers to the subset of pre-determined questions. The optional account information 526 may allow at least the first individual to communicate with one or more providers of services that determine one or more association variables.

In some embodiments, at least first individual is provided with the optional memory device 524, which may be installed in the device 500. One or more additional optional memory devices may also be provided to at least the first individual at later times during the data-collection time interval. The one or more additional optional memory devices may include revised pre-determined questions 354 and/or revised pre-selected answers 358.

In some embodiments, the optional memory device 524 is a SIMS card, an SD card, and/or a memory card and the device 500 is a cellular telephone. By including the optional account information 526, communication using at least the one carrier account number and/or at least the one telephone number may avoid the so-called SIMS card lock that prevents modification of such information in a cellular telephone that is issued by a cellular telephone provider to a subscriber. This may allow one or more modules or applications to be installed and/or executed on the cellular telephone independently of the cellular telephone provider. Address book and/or additional telephone numbers (such as a list of frequently used telephone numbers) on an existing SIMS card, SD card, and/or memory card for at least the first individual may be copied on to the optional memory device 524. Alternatively, at least the first individual may at least temporarily provide the existing SIMS card, SD card, and/or memory card, which may allow the address book and/or the additional telephone numbers to be copied on to a new optional memory device 524 that may be provided to at least the first individual.

In some embodiments, the pre-determined questions 354 and/or the pre-selected answers 358 may be copied on to the optional memory device 524 or the existing SIMS card, SD card, and/or memory card in a cellular telephone. Service, such as collecting the information, may be provided in conjunction with or separately from one or more cellular telephone service providers. In some embodiments, revised pre-determined questions 354 and/or revised pre-selected answers 358 may be transmitted to and stored on the optional memory device 524 on one or more occasions during the data-collection time interval.

In some embodiments, at least the first individual owns or rents the device 500, thereby reducing a cost associated with collecting information, as well as a cost and complexity associated with supporting and maintaining hardware in the field. In some embodiments, at least the first individual is provided, either temporarily or permanently, with the device 500.

The modules and/or some components in the memory device 516 may be arranged in a protocol stack, including a physical layer, a link layer, a network layer, a transport layer, and/or an application layer. In an alternate embodiment, the protocol stack may include the network layer, the transport layer, a security layer, a session transaction layer, and/or the application layer. Instructions in the modules in the memory device 516 may be implemented in a high-level procedural language, an object-oriented programming language, and/or in an assembly or machine language. The programming language may be complied or interpreted, i.e, configurable or configured to be executed by one or more processors 510. In addition, the device 500 may include fewer or additional executable procedures, sub-modules, tables and other data structures (not shown). In some embodiments, additional or different modules and data structures may be used and some of the modules and/or data structures listed above may not be used. In some embodiments, the functions of two or more modules may be combined in a single module. In some embodiments, implementation of functionality of the device 500 may be implemented more in hardware and less in software, or less in hardware and more in software, as is known in the art.

Although the device 500 is illustrated as having a number of discrete items, FIG. 5 is intended more as a functional description of the various features which may be present in the device 500 rather than as a structural schematic of the embodiments described herein. In practice, and as recognized by those of ordinary skill in the art, the functions of the device 500 may be distributed over a large number of servers or computers, with various groups of the servers or computers performing particular subsets of the functions. Items shown separately in the device 500 may be combined, some items may be separated and/or additional items may be added. One or more items or modules in the memory device 516, such as the configuration instructions 420, may be stored in the optional memory device 524 and vice versa. The apparatuses and methods disclosed may be implemented in hardware and/or software. In alternate embodiments, some or all of the functionality of the device 500 may be implemented in one or more ASICs and/or one or more DSPs.

Figure 6A:
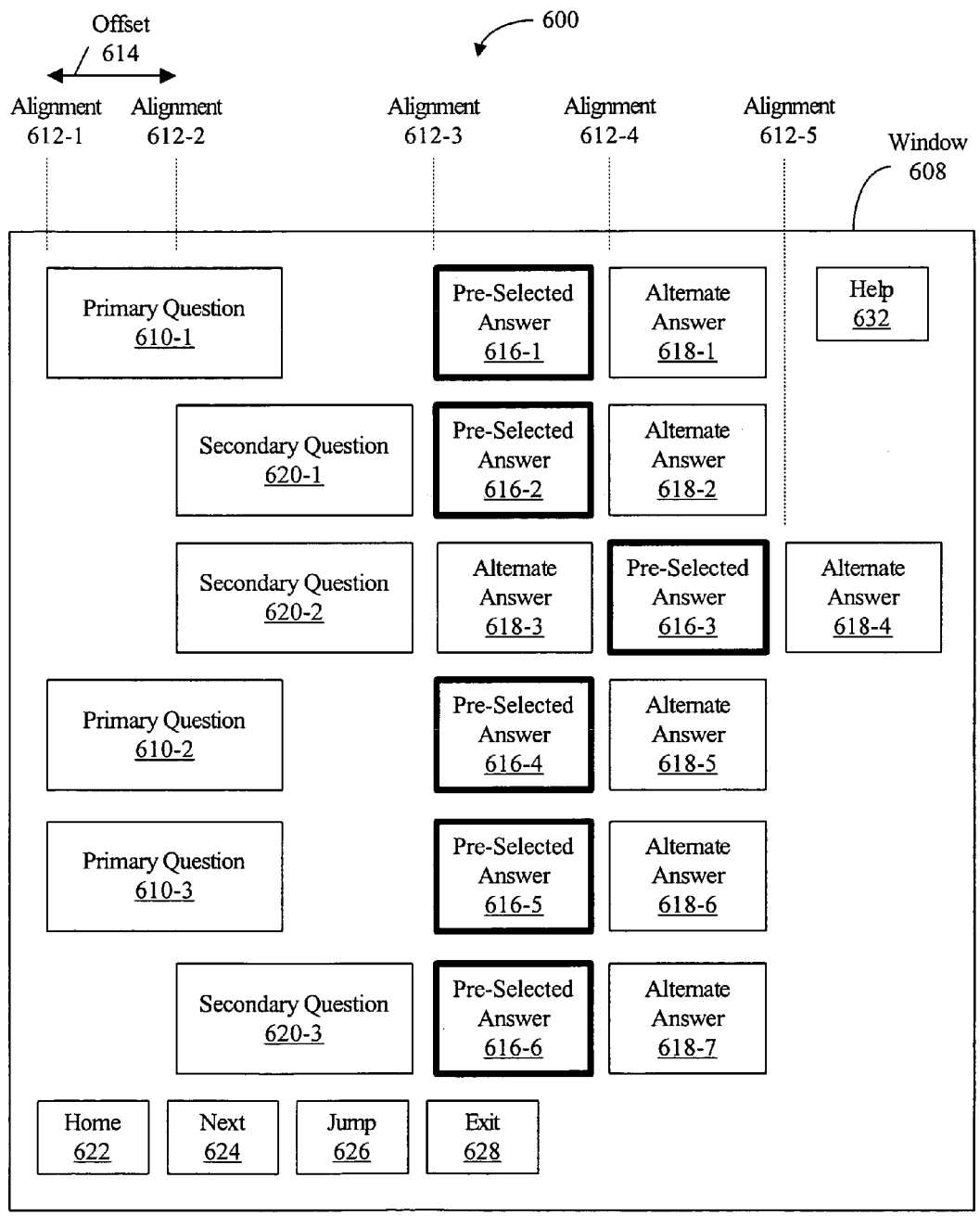
FIG. 6A is a block diagram illustrating an embodiment of a questionnaire.
Figure 6C:
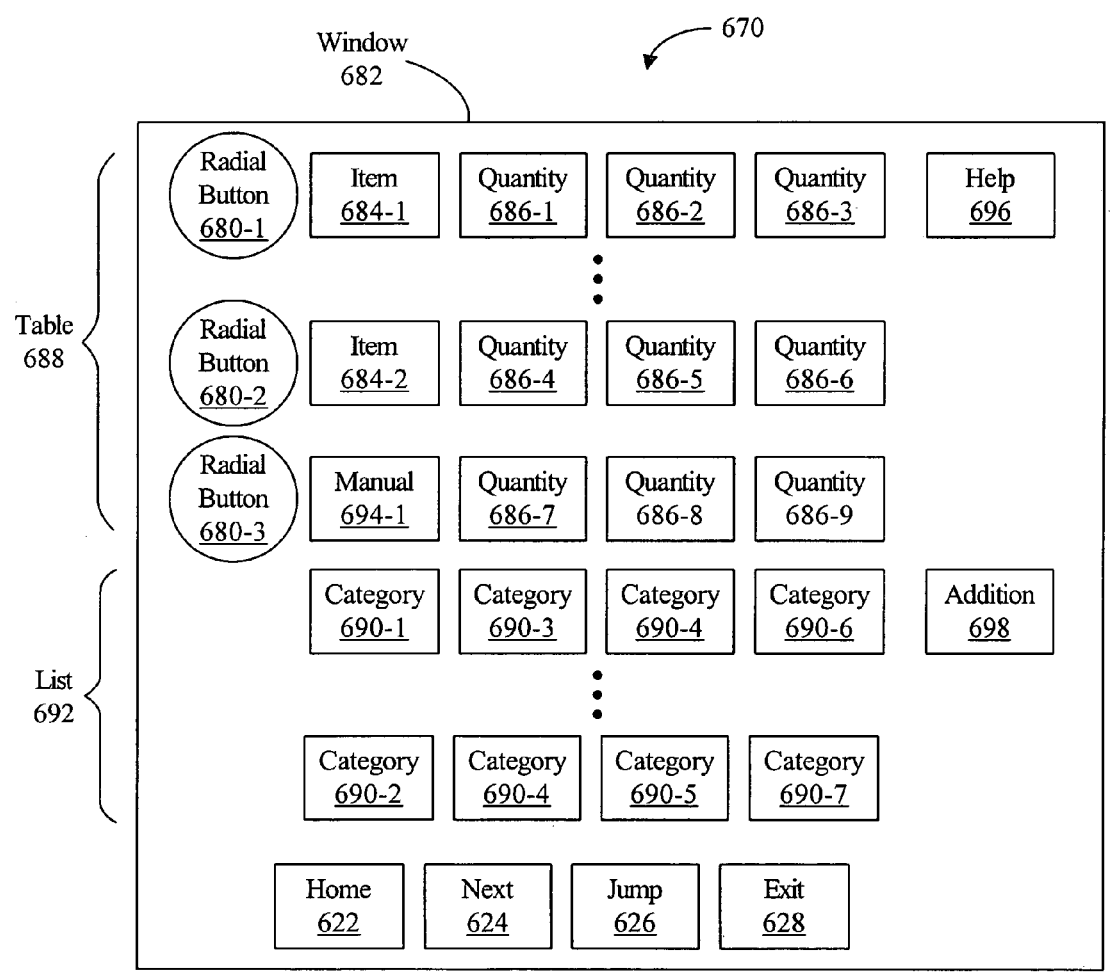
FIG. 6C is a block diagram illustrating an embodiment of a questionnaire.
Figure 6B:
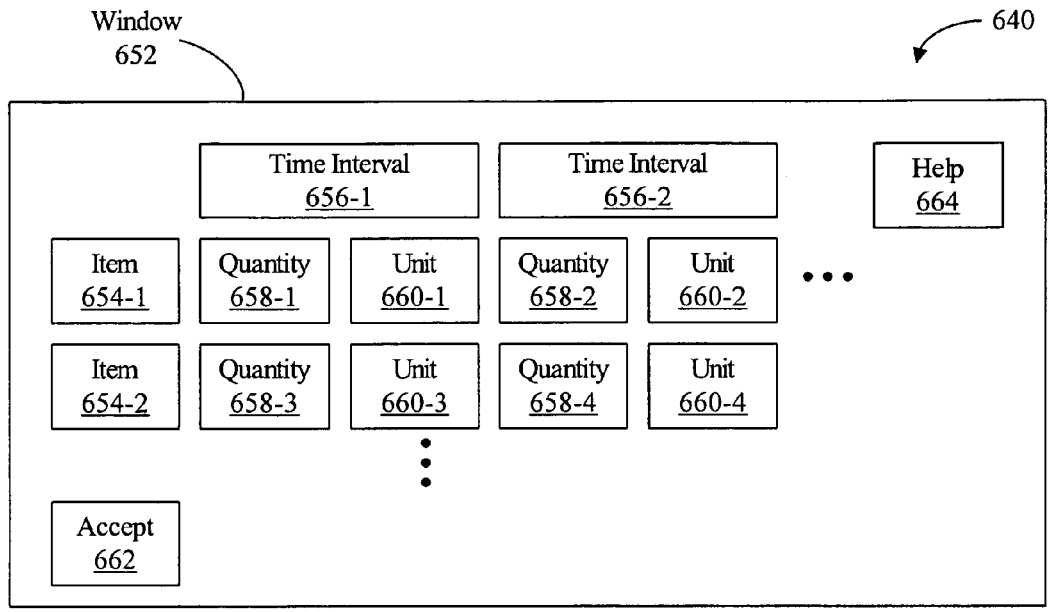
FIG. 6B is a block diagram illustrating an embodiment of a questionnaire.

Attention is now directed towards embodiments of the questionnaire and formats for displaying information contained in embodiments of the questionnaire. As noted previously, the subset of pre-determined questions may be provided (for example, displayed) to at least the first individual along with respective pre-selected answers for each question in at least a plurality of the pre-determined questions in the subset of pre-determined questions. In this way, answering a respective pre-determined question may involve selection if a respective answer to the respective pre-determined question is different than a respective pre-selected answer. The pre-selected answers may be selected in accordance with an answer history, such as the answer history 360 (FIG. 3), and/or default answers, such as the default answers 362 (FIG. 3). FIGS. 6A–6C illustrate embodiments of a questionnaire including pre-determined questions and pre-selected answers.

FIG. 6A is a block diagram illustrating an embodiment of a questionnaire 600, such as a questionnaire module (which may contain related questions in a category of questions). Questionnaire modules are discussed further below with reference to FIGS. 8A and 8B. In the questionnaire 600, several primary questions 610, including pre-selected answers 616 and alternate answers 618, are displayed in a window 608. The window may be a graphical user interface, such as a dialog box or window, and it may be displayed on a display, such as the display 316 (FIG. 4). A left edge of at least a plurality of the primary questions 610 may be aligned with alignment 612-1 such that the primary questions 610 are arranged in a column. A left edge of at least a plurality of the pre-selected answers 616 may be aligned with alignment 612-3 such that the pre-selected answers 616 are arranged in a column. A left edge of at least a plurality of the alternate answers 618 may be aligned with alignment 612-4 such that the alternate answers 618 are arranged in a column. In other embodiments, a right-edge, a center or another position in the primary questions 610, the pre-selected answers 616 and/or the alternate answers 618 may be used for purposes of alignment.

If the pre-selected answers 616 are correct, at least the first individual may select a next 624 icon at the bottom of the window 608 (for example, by positioning a cursor over the accept 624 icon and left clicking on a mouse) to accept the pre-selected answers 616 and request another window (unless the questionnaire 600 is completed) with additional pre-determined questions and/or pre-selected answers. Selection of one or more of the alternate answers 618, such as alternate answer 618-1, may occur if a corresponding pre-selected answer 616-1 is not the correct answer for a corresponding primary question, such as primary question 610-1.

If one or more of the alternate answers 618 are selected, secondary questions 620 may be displayed and/or enabled (i.e., at least the first individual may be able to modify the answer to a secondary question, such as secondary question 620-1). In some embodiments, when an alternate answer, such as alternate answer 618-1 is selected, a displayed color of one or more of one or more previously displayed secondary questions 620 may be changed, for example, from grey to black or from white to black. Note that some primary questions 610 may not have one or more associated secondary questions 620 associated with them. The secondary questions 620 may dependent on or may be conditional on the answers to corresponding primary questions 610. A left edge of at least a plurality of the secondary questions 620 may be aligned with alignment 612-2 such that the secondary questions 620 are arranged in a column. In other embodiments, a right-edge, a center or another position in the secondary questions 620 may be used for purposes of alignment. The alignment 612-2 may be offset 614 from the alignment 612-1.

In the questionnaire 600, the primary questions 610 may be categorical or discrete questions, i.e., having answers such as 'yes' or 'no'. In some embodiments, the pre-selected answers 616 may include both 'yes' and 'no' responses. As a consequence, the pre-selected answers 616 may alternate between 'yes' and 'no' for different primary questions 610. In an alternate embodiment, 'yes' answers may be arranged in a first column and 'no' answers may be arranged in a second column, such that a position for the pre-selected answers 616 and the alternate answers 618 may varying between the first column and the second column depending on the primary questions 610. In the questionnaire 600, the secondary questions 620 may include categorical questions as well as one or more ordered categorical secondary question 620-2. (A left edge of the alternate answer 618-4 may be aligned with alignment 612-5. In other embodiments, a right-edge, a center or another position in the alternate answer 618-4 may be used for purposes of alignment.) In an ordered categorical question, there is an ordering between values (such as answers of 'small', 'medium,' or 'large') but a scale or metric value may vary (a difference between 'medium' and 'small' may be different than a difference between 'large' and 'medium'). In some embodiments, an ordered categorical question may have a pre-selected answer, such as pre-selected answer 616-3, that is in a different column than other pre-selected answers 616. This may be useful when the ordered categories are time intervals, such as morning, afternoon, etc., and the pre-selected answer is not the left-most ordered category. Rather than rearranging the ordered categories, the pre-selected answer 616-3 may be in a different column.

In some embodiments, the primary questions 610 and the secondary questions 620 may include categorical, ordered categorical and/or quantitative questions. Quantitative questions have answers that are continuous variables. Answers to quantitative questions may be partition, for example using one or more thresholds or threshold values, to generate categorical or ordered categorical answers. In some embodiments, answers to one or more quantitative questions may be band limited prior to partitioning to reduce or eliminate aliasing. Categorical or ordered categorical answers may be converted into continuous answers using interpolation (such as minimum bandwidth interpolation), subject to the limitations associated with the Nyquist sampling criterion.

In the questionnaire 600, the window 608 may include one or more help icons 632, a home icon 622 to return to a master page in the questionnaire 600, a jump icon 626 to save answers and skip to another window, an exit icon 628 to save answers and exit the questionnaire 600. While the questionnaire 600 includes three primary questions 610 and three secondary questions 620, there may be fewer or more of either type of question. In some embodiments, a respective question may have one or more answers.

FIG. 6B is a block diagram illustrating an embodiment of a questionnaire 640. Selection of a respective alternate answer, such as alternate answer 618-6 (FIG. 6A), to one of the primary questions 610 (FIG. 6A) or secondary questions 620 (FIG. 6A) may lead to window 652 being displayed. The window 652 may include one or more help icons 664, and one or more items 654 with one or more quantities 658 and units 660 (henceforth collectively referred to as entries) during corresponding time intervals 656. At least the first individual may accept the entries using an accept icon 662 after making modifications (if any). Modifications may be made to one or more entries by positioning a cursor over an entry and manually typing one or more new values and/or by left clicking on the mouse with the cursor over the entry and selecting a new value from a list box (a static object in the window 652) that appears when the mouse is positioned over it and/or a content-dependent list or menu (a dynamic object) that may appear as a separate window when the mouse is positioned over it. A list box and/or a content-dependent list or menu may include related objects and/or items, such as those corresponding to a category of items. In some embodiments, the entries in the window 652 may blink to indicate that at least the first individual may modify one or more of them. In an exemplary embodiment, the items 654 may include pharmacological agents, prescription drugs, vitamins, herbs, supplements and/or recreational or illicit drugs (henceforth referred to as pharmacological agents). The quantities 658 and units 660 may correspond to dosages. The time intervals 656 may be a fraction of a day, such as approximately 1, 2, 3, 4, 6, 8, and/or 12 hours. Thus, 50 mg of a drug taken in the morning (such as between 6 AM and 11.59 AM), may correspond to a quantity 658-1 of '50' and a unit 660-1 of 'mg'. The entries in the window 652 may be pre-selected based on the answer history, default answers, and/or answers to one or more questions in the optional initial survey, which may include the usage of pharmacological agents (times and dosages) by at least the first individual. The optional initial survey may be conducted prior to or at the beginning or the data-collection time interval during which the subset of pre-determined questions corresponding to the questionnaire are asked.

FIG. 6C is a block diagram illustrating an embodiment of a questionnaire 670. A window 682 may include a table 688 including one or more items 684 and/or a list 692 including one or more categories 690. Each of the items 684 may have ordered categorical answers such as quantities 686. For example, quantity 686-1 may be 'less than usual', quantity 686-2 may be 'usual', quantity 686-3 may be 'more than usual'. One or more respective quantities 686, such as the quantity 686-1, for one or more respective items 684, such as the item 684-1, may be pre-selected. Categories 690 may be list boxes, and/or content-dependent lists or menus. The categories 690 may correspond to food or beverage categories, such as vegetables, fruits, meats, etc.

In an exemplary embodiment, the window 682 may be used to collect information corresponding to one or more meals or snacks, such as foods eaten or beverages consumed. In some embodiments, snacks eaten between meals may be included in the nearest previous meal. For example, a snack after dinner and before breakfast may be included with the entries for dinner. The items 684 may be included in accordance with answers to one or more pre-determined questions in the subset of pre-determined questions during a current questionnaire session (for example, in another questionnaire module) and/or may be previously consumed foods (which may be stored in an answer history, such as the answer history 360 in FIG. 3, corresponding to one or more previous answer sessions, i.e., on one or more earlier occasions). The one or more pre-selected quantities may be in accordance with the answer history. The previously consumed foods may be the most common foods (for example, a top 10 list) consumed by at least the first individual. At least one of the categories 690 may include additional consumed foods and/or previously consumed foods for at least the first individual that are not displayed in the table 688. The items 684 may include food brand and/or food category (such as Italian) information. In some embodiments, food brand and/or food category may be displayed using icons (not shown) situated between the items 684 and the quantities 686.

One or more items 684 may be selected by clicking on one or more radial buttons 680 (for example, positioning the mouse over a respective item and left clicking the mouse). A displayed color of one or more selected items may be changed, for example, from grey to black. In some embodiments, the window 682 may be refreshed such that selected items are displayed starting at the top of the table 688 and items that are currently not selected are displayed below the selected items, i.e., towards the bottom of the table 688. Additional items for inclusion in the table 688 may be selected from one or more categories 690 and/or may be manually entered using one or more optional manual entry boxes 694.

Selecting a category, such as category 690-1, may lead to a content-dependent list or menu being displayed in a separate dialog box or window. Entries selected from one or more categories 690 may be displayed in the table 688 as additional items with pre-selected quantities and/or pre-selected radial buttons. The window 682 may be refreshed and/or re-ordered when one or more of such entries are displayed. At least the first individual may modify, as needed, one or more pre-selected quantities for one or more of such entries displayed in the table 688 (for example, if one or more of the pre-selected quantities did not correspond to one or more actual quantities consumed by at least the first individual). In some embodiments, entries in the window 670 that may be modified, such as the one or more pre-selected quantities and/or the optional manual entry box 694, may blink to indicate that at least the first individual may modify one or more of them. Selecting an addition 698 icon may display a window that allows at least the first individual to add one or more entries to one or more categories 690. Alternative, the separate dialog box or window for a respective content-dependent list that has been selected may include a manual entry option so at least the first individual may add one or more entries to the respective content-dependent list. The optional manual entry boxes, such as the optional manual entry box 694, in the table 688 may be used to enter one or more new items, food brands, and/or food categories. Corresponding quantities may be entered using the quantities 686. While the questionnaire 670 shows one optional manual entry box 694, in some embodiments there may be additional manual entry boxes in one or more additional rows. Each row may be used to enter at least one new item.

In embodiments where windows in the questionnaire 670 are provided in one or more web pages, JavaScript instructions included with the one or more web pages may allow the table 688 to be updated without blinking the displayed window 682, i.e., without transmitting revised web page instructions from a remote server or computer, such as the server or computer 300 (FIG. 3). In the questionnaire 670, the window 682 may include one or more help icons 696, the home icon 622, the next icon 624, the jump icon 626 and/or the exit icon 628. In some embodiments, the window 682 may include additional or fewer items 684 and/or categories 690.

A better understanding of the questionnaire and the determining of one or more association variables (described further below with reference to FIGS. 9–14) may be provided by considering application to a class of problems, such as those associated with one or more diseases. Migraines are used as an illustrative example. In this example, at least the first individual may be a migraine patient. In some embodiments, migraines may include probable migraine, also referred to as migrainous, in which patients exhibit migraines minus one migraine symptom (which are discussed below).

Migraine is a neurovascular disorder characterized by a family of symptoms that often include severe, recurring headache usually on one-side of the head. Migraine attacks are debilitating and have a duration that may last from several hours to days. During attacks, many patients also exhibit sensitivity to environmental stimuli, such as light and sound, and/or experience nausea or vomiting. Some characteristics of migraines, with and without aura, are summarized in Tables I and II. Migraines typically follow a cycle, including an initial or prodrome phase during which premonitory symptoms (discussed further below with reference to FIG. 8A) may be present, an aura phase (for patients that have migraine with aura) during which visual disturbances may be present, a resolution or recovery phase, and a normal (i.e., non-migraine) phase.

TABLE I

Some characteristics of migraine without aura.

A. Headache attacks lasting 4–72 hours (untreated or unsuccessfully treated).
B. Headache has at least two of the following characteristics:
   1. Unilateral location;
   2. Moderate or severe pain intensity;
   3. Pulsating quality;
   4. Aggravated by or causing avoidance of routine physical activity (for example, walking or climbing stairs).
C. During headache at least one of the following:
   1. Nausea and/or vomiting;
   2. Light sensitivity (photophobia) and sound sensitivity (phonophobia).

TABLE II

Some characteristics of migraine with aura.

A. Aura consisting of at least one of the following, but no motor weakness:
   1. Fully reversible visual symptoms including positive features (for example, flickering lights, spots or lines) and/or negative features (such as, loss of vision);
   2. Fully reversible sensory symptoms including positive features (such as, pins and needles) and/or negative features (such as, numbness);
   3. Fully reversible dysphasic speech disturbance.
B. At least two of the following:
   1. Homonymous visual symptoms and/or unilateral sensory symptoms;
   2. At least one aura symptom develops gradually over $\geq 5$ minutes and/or different aura symptoms occur in succession over $\geq 5$ minutes;
   3. Each symptom lasts $\geq 5$ and $\leq 60$ minutes.
C. Headache fulfilling criteria B–D for migraine without aura (Table I) begins during the aura or follows aura within 60 minutes.

The medical approach to managing migraine headaches is typically three-pronged, including acute therapy, preventive therapy, and identification and avoidance of migraine triggers. Acute therapy includes administering acute or prophylactic pharmacological agents, such as painkillers or analgesics, (for example, aspirin, acetaminophen or naproxen), ergotamine, dihydroergotamine, and/or a new class of medications known as "triptans" (selective serotonin 5-hydroxytryptamine or 5-HT receptor agonists, such as imitrex and maxalt), which are migraine-specific medications that may treat the entire migraine complex, relieving the head pain, nausea, vomiting, and associated light and sound sensitivity, typically within 1–2 hours. Most patients with migraine are prescribed one or more forms of acute therapy.

Preventive therapy includes pharmacological agents or medications taken on a daily basis to reduce migraine headache frequency (a number of headaches during a time period) and severity (for example, a rating of headache pain by a patient). These pharmacological agents may be taken whether a migraine headache is present or not. Prevention strategies are typically employed for patients who suffer from one or more migraine headaches per week. Only a minority of patients require this form of therapy.

Identification and avoidance of migraine triggers is typically a mainstay in the treatment of patients suffering from migraine. If patients successfully avoid their migraine triggers, migraine headache frequency and severity may be improved. (Note that some migraine triggers, such as certain hormones, may be intrinsic or internal to the patient. As such, the patient may still have spontaneous migraine attacks even if he or she successfully avoids his or her dominant migraine triggers.) Identifying migraine triggers, however, remains challenging and is often a source of frustration for patients and healthcare providers. This is partly an outgrowth of the apparent complexity of migraine triggers. A myriad of probable or putative migraine triggers are thought to exist. It has been hypothesized that the migraine triggers may vary significantly from one patient to another, may vary within a respective patient (as discussed below with reference to FIG. 7, the respective patient's sensitivity threshold for a respective trigger may vary as a function of time), may depend on a quantity of exposure, and/or may depend on exposure to two or more triggers in close temporal proximity.

In addition, current approaches for screening for migraine triggers may pose challenges. Typically, patients are given paper diaries and are asked to list what they think may have triggered an attack on a respective day. This approach may rely on the patients' recall of events, as diaries are often filled in days after a migraine attack, and may therefore miss an exposure to migraine triggers. Patients may also assign a cause when one may not exist, or patients may assign blame to an incorrect variable(s). The apparent complexity of migraine triggers may compound these difficulties.

Figure 7:
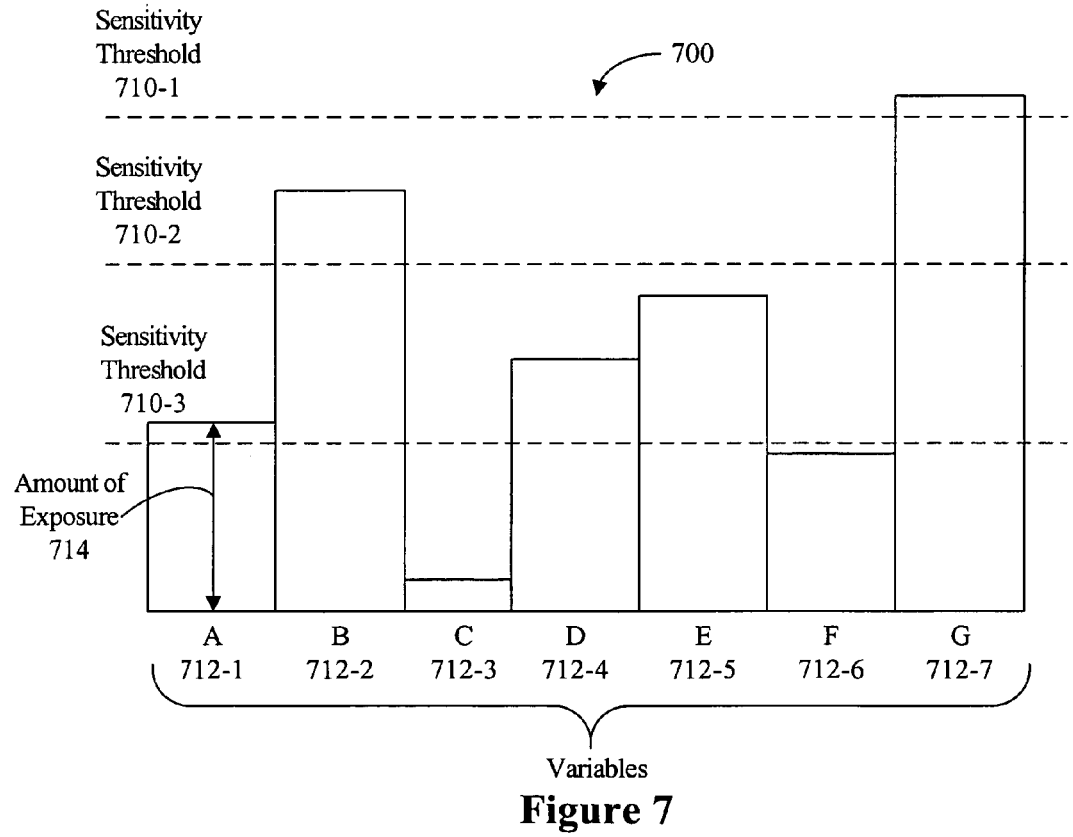
FIG. 7 is a block diagram illustrating an embodiment of migraine triggers and sensitivity thresholds.

FIG. 7 is a block diagram illustrating an embodiment 700 of migraine triggers and sensitivity thresholds. A plurality of variables 712, corresponding to migraine triggers, each having a length corresponding to an amount of exposure 714 during a time interval are illustrated. Sensitivity thresholds 710 illustrate several effective sensitivities for at least the first individual. At any given time, one or more of the sensitivity thresholds 710 may be operative for one or more of the variables 712. The sensitivity thresholds 710 may vary as a function of time. Such variation may occur slowly, for example, over a period of months or even years. Variables 712 that exceed one of the sensitivity thresholds 710 corresponding to a current sensitivity for at least the first individual, such as variable B 712-2 and sensitivity threshold 710-2, may trigger a migraine attack. Alternatively, combinations of variables 712, such as variable C 712-3 and variable F 712-6, may exceed a sensitivity threshold 710-3 and trigger a migraine. The combinations may be cumulative, may correspond to variables 712 that occur in close temporal proximity, may correspond to respective temporal sequences of variables 712, and/or may correspond to respective ordered temporal sequences of variables 712 during the data-collection time interval. While embodiment 700 illustrates 7 variables 712, in some embodiments there may be fewer or more variables 712.

Other intricacies associated with migraines are so-called rebound and recurrence headaches. While analgesics are designed to relieve pain, if such pharmacological agents (both prescription and nonprescription) are overused (repetitive and chronic use), they can actually cause headaches. This is known as analgesic rebound headache (ARH) or "rebound headache." Headache sufferers taking analgesic medications every day, or even as infrequently as two times a week, may find that they must take ever-increasing dosages to achieve relief. With continued overuse the medication becomes less and less effective, with pain-free periods between headaches becoming shorter and shorter. The result can be a self-sustaining cycle of increasing pain and medication.

Recurrences headaches are associated with headaches returning after a pain-free period following treatment with one or more medicines. In essence, the migraine attack "outlasts" the treatment, so the headache returns when the medication wears off. Recurrence is commonly seen following treatment with a triptan. For example, a headache resolves within one to two hours after taking a triptan, only to return full blown (i.e., with full severity) within 24 hours. In some embodiments, a recurrence headache may be defined as any headache occurring after a headache-free state at 2 hours and within 12 hours after intake of an acute pharmacological agent. In some embodiments, a recurrence headache may be defined as any headache occurring after a headache-free state at 2 hours and within 24 hours after intake of an acute pharmacological agent. A recurrence headache may have different characteristics of intensity, severity and/or associated features than an original headache episode during a migraine attack. In some cases, a recurrence headache may be of migraine or tension-type. (Some characteristics of tension headaches are summarized in Table III.)

TABLE III

Some characteristics of tension headaches.

A. At least 2 of the following 4 headache features:
   1. Bilateral location;
   2. Pressing/tightening quality;
   3. Mild or moderate intensity;
   4. Not aggravated by routine physical activity.
B. Both of the following:
   1. No nausea or vomiting
   2. Not more than one of light or sound sensitivity.
C. Duration lasting from 30 minutes to 7 days.

In the context of the disclosed embodiments, the one or more events may be one or more migraines, and the one or more temporal onsets corresponding to the one or more events may be a respective onset time and/or a respective onset time interval for one or more migraines. Onset times for migraines may be determined in accordance with one or more premonitory symptoms (discussed further below with reference to FIG. 8A) that may be experienced by at least the first individual during the prodrome phase of a migraine attack, one or more migraine symptoms during the aura phase of a migraine attack, one or more migraine symptoms during the headache phase of a migraine attack, and/or an onset of head pain as indicated by at least the first individual.

In some embodiments, the one or more physiological monitors 372 (FIG. 3) may, at least in part, determine one or more onset times for migraines. Since migraines impact the hypothalamus, with consequences for the endocrine system, the limbic system and the autonomic nervous system, a variety of physiological changes may be observable in one or more migraine patients. These physiological changes may include changes in a circadian rhythm, changes in one or more vital signs (such as pulse, respiration, systolic blood pressure, and/or diastolic blood pressure), hormonal changes, emotional changes, changes in a pulse pressure (defined as a difference of the systolic blood pressure and the diastolic blood pressure), changes in skin electrical or thermal conductivity (such as perspiration), and/or changes in at least one reflex arc. The physiological changes may be bilateral or unilateral. In an exemplary embodiment, the pulse pressure may increase or decrease by 1%, 3%, 5% or more than 10% during the prodrome phase. In some embodiments, the one or more physiological monitors 372 (FIG. 3) may determine a presence of (sub-) cutaneous allodynia or 'skin pain' (such as a sensitive or painful scalp), a condition associated with central sensitization, which is indicative of a deeply entrench migraine attack. In some embodiments, the one or more physiological monitors 372 (FIG. 3) may provide a metric of chronic disease regulation, for example, a frequency and/or a severity of migraines.

The pre-determined questions in the questionnaire, such as the questionnaire 600 (FIG. 6A), may correspond to patterns of occurrence (including presence and absence information) of the set of variables that are potential migraine triggers. The one or more association variables may correspond to one or more migraine triggers, and/or one or more probable or putative migraine triggers. The one or more association variables may be patient-specific, may occur in one or more groups of migraine patients, and/or may occur in at least a plurality of migraine patients. The one or more association variables may at least in part induce a migraine in at least the first individual if at least the first individual is exposed to one or more of the association variables. In some embodiments, the one or more association variables may be the dominant migraine triggers, such as those migraine triggers associated with 10%, 25%, 33%, 50%, or more of the migraine attacks, for at least the first individual.

Variables that may be migraine triggers may include weather changes, allergens, compounds containing phenols (also referred to as phenolic compounds), pollution, hormonal fluctuations (such as during the menstrual cycle, pregnancy, post partum, and/or menopause), trauma, illness, hypoglycemia, sensory stimuli (such as lights, sounds, and/or smells), physical exertion, sexual activity, motion, travel, sleep patterns (when and/or how much sleep), intense emotion, withdrawal of intense emotion, stress, withdrawal of stress, certain pharmacological agents (such as MAO inhibitors, oral contraceptives, estrogen replacement therapy, recreational drugs, and/or tobacco products), dietary patterns (when food is consumed), and/or diet (what and/or how much is consumed). Dietary migraine triggers may include alcohol (for example, wine), sugar substitutes (such as Aspartame), caffeine (including caffeine withdrawal), food additives (such as monosodium glutamate or MSG), one or more fruits, one or more vegetables, one or more spices, one or more nuts, fermented food (such as vinegar), foods containing amounts of certain amino acids (such as tyramine) that exceed one or more quantity thresholds, foods containing amounts of nitrates that exceed a first quantity threshold, foods containing amounts of sulfites that exceed a second quantity threshold, and/or foods containing amounts of tannins that exceed a third quantity threshold. For example, dietary migraine triggers may include blue cheese, oranges, carrots, vinegar and caffeine.

Attention is now directed towards application of the embodiments of the questionnaire for collecting information associated with migraines, such as variables corresponding to potential or putative migraine triggers. It should be understood, however, that the description applies to numerous applications and embodiments, including non-medical applications.

Prior to or at the beginning of the data-collection time interval, at least the first individual may answer one or more questions in the optional initial survey. In some embodiments, the questions may be based on at least the first individual's medical history. The optional initial survey may confirm that at least the first individual meets any applicable entry criteria, determine one or more questionnaire modules (discussed further below with reference to FIG. 8A) that may be relevant for at least the first individual, and collect initial information, such any pharmacological agents that at least the first individual takes on a regular basis (for example, daily). In the case of migraines, entry criteria may include determining that the disease in a respective patient, such as at least the first individual, is sufficiently well controlled that migraine attacks are not occurring too often (such as every day) or too infrequently (such as once a year) to preclude determination of one or more migraine triggers. For migraines, pharmacological agents may include one or more acute therapies and/or one or more preventive therapies. The pharmacological agents may include other medicines (prescription and/or non-prescription), vitamins, herbs, supplements, and/or recreational drugs that at least the first individual takes on a regular basis. The initial information may include quantities and/or times when one or more of the pharmacological agents are used.

Figure 8A:
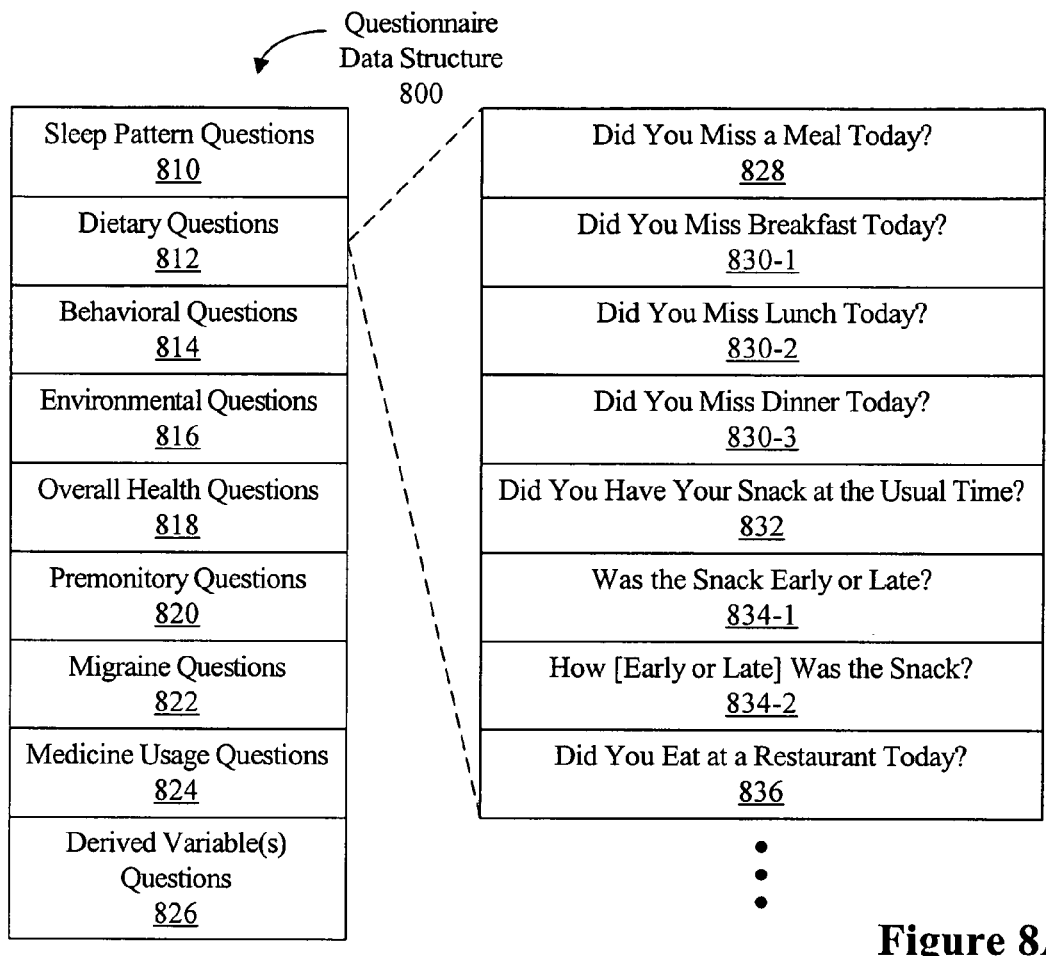
FIG. 8A is a block diagram illustrating an embodiment of a questionnaire data structure.

As noted above, pre-determined-questions in the questionnaire may be grouped into questionnaire modules. FIG. 8A is a block diagram illustrating an embodiment of a questionnaire data structure 800 including multiple pre-determined questions, such as the pre-determined questions 354 (FIG. 3), arranged in multiple questionnaire modules, such as the questionnaire modules 356 (FIG. 3). The questionnaire data structure 800 may include sleep pattern questions 810 (including questions related to sleep apnea and/or insomnia), dietary questions 812 (such as dietary patterns and diet), behavioral questions 814 (such as hormonal fluctuations, physical exertion, sexual activity, motion, travel, exposure to intense emotion, withdrawal of intense emotion, exposure to stress, withdrawal of stress, and/or a use of tobacco products), environmental questions 816 (such as exposure to sensory stimuli, exposure to compounds containing phenols, and/or exposure to weather conditions such as strong wind), overall health questions 818 (such as pregnancy, a presence of trauma, illness, depression, and/or hypoglycemia), premonitory questions 820, migraine questions 822, medicine usage questions 824 (such as preventive therapies, vitamins, herbs, oral contraceptives, estrogen replacement therapy, recreational drugs, and/or pharmacological agents, including analgesics, other than migraine-specific drugs such as triptans), and/or derived variable(s) questions 826.

The premonitory questions 820 include symptoms that may be experienced and/or exhibited by at least the first individual during the prodrome phase of a migraine attack. Premonitory symptoms may include excitatory symptoms, inhibitory symptoms and/or localized pain (for example, in the head, neck and/or shoulders). Excitatory symptoms may include cravings (such as hunger and/or thirst), increased activity, sweating, a sense of well being, emotional changes (such as irritability), increased urination or bowel movements, and/or increased sensitivity to sensory stimuli. Inhibitory symptoms may include confusion, difficulty concentrating, depression, dizziness, fatigue, constricted circulation, yawning, and/or a lack of appetite.

The migraine questions 822 may include migraine occurrence information, migraine information (such as pain location, severity, quality or description, patterns, and/or temporal variation), use of medicines (including pharmacological agents such as one or more acute therapies), use of non-pharmacological treatments, a presence of visual disturbances, symptoms of (sub-) cutaneous allodynia, and/or other migraines symptoms (such as nausea and/or vomiting). The migraine occurrence information may include one or more temporal onsets or onset times.

In some embodiments, at least the first individual may be asked the derived variable(s) questions 826. One or more answers to the derived variable(s) questions 826 may be determined in accordance with one or more answers to one or more pre-determined questions in one of the other questionnaire modules. For example, exposure to a food containing tyramine may be determined based on one or more answers to one or more pre-determined questions in the dietary questions module 812. One or more answers to the derived variable(s) questions 826 may be determined in accordance with a mapping operation performed on one or more answers to one or more pre-determined questions in the dietary questions module 812. For example, one or more foods consumed (such as mayonnaise) may be mapped to basic constituents (egg, vinegar, and/or mustard) and/or elemental constituents (minerals, fats, carbohydrates, and proteins). The mapping operation may be performed using tables of related information, such as one or more recipes and/or elemental constituent information. Elemental constituent information for some foods may be obtained in the National Nutrient Database on the United States Department of Agriculture's website at www.nal.usda.gov/fnic/food-comp/Data. One or more answers to the derived variable(s) questions 826 may be determined in accordance with other public information, such as weather (conditions and/or changes), altitude, allergen, and/or pollution information. For example, pollution information may be obtained from the United States Environmental Protection Agency's website at www.epa.gov/air/data. In some embodiments, one or more answers to the derived variable(s) questions 826 may be determined in accordance with at least the first individual's location(s), which may determined using the optional location module 370 (FIG. 3), during the data-collection time interval.

The pre-determined questions in one or more of the questionnaire modules may correspond to deviations from normal or usual behavior for at least the first individual. For example, deviations from normal sleep patterns for at least the first individual, deviations from normal behavior while at least the first individual is awake, and/or deviations from normal dietary behavior for at least the first individual.

In some embodiments, a respective questionnaire module, such as the dietary questions 812, may include primary questions, such as the primary questions 610 (FIG. 6A), and secondary questions, such as the secondary questions 620 (FIG. 6B). For example, the dietary questions 812 may include are primary questions such as pre-determined questions 828 ("Did you miss a meal today?"), 832 ("Did you have your snack at the usual time?") and 836 ("Did you eat at a restaurant today?"). Pre-determined questions 830-1 (Did you miss breakfast today?"), pre-determined questions 830-2 ("Did you miss lunch today?"), pre-determined questions 830-3 ("Did you miss dinner today?"), pre-determined questions 834-1 ("Was the snack early or late?") and pre-determined questions 834-2 ("How [Early or Late] was the snack?") may be secondary questions. Note that pre-determined (secondary) question 834-2 may depend on the answer to pre-determined (secondary) question 834-1.

At least some of the dietary questions 812 may be displayed using a format such as that illustrated in FIG. 6A and/or 6C. Other questions in one or more other questionnaire modules may be displayed using a format such as that illustrated in FIG. 6B. For example, medicine usage questions 824 and/or the use of medicines pre-determined questions in the migraine questions 822 may be displayed using the format in FIG. 6B. Pre-selected answers 616 (FIG. 6A) for some of the pre-determined questions may correspond to a usual or a normal behavior for at least the first individual in accordance with at least the first individual's answer history 360 (FIG. 3), the answer history 360 (FIG. 3) for one or more groups (such as men, women, an age group, a demographic group, groups of migraine patients, and/or groups of migraine patients having one or more migraine triggers in common), one or more answers to the optional initial survey, and/or one or more default answers 362 (FIG. 3).

Answers, be they pre-selected or not, to the pre-determined questions in the dietary questions 812, as well as in one or more other questionnaire modules, may be categorical, ordered categorical, and/or quantitative. For example, the answer to pre-determined question 828 may be 'yes' or 'no'. The answer to pre-determined (secondary) question 834-2 may be quantitative (a time in hours, minutes and/or seconds) and/or ordered categorical (between 0–1 hours, between 1–2 hours, etc.). Ordered categorical answers to some of the primary or secondary questions may include time intervals, such as the time intervals 656 (FIG. 6B), that correspond to a fraction of a day. In an exemplary embodiment, a presence or absence of a respective variable may be determined in accordance with a selection of a 'yes' answer to a primary question and a selection of one or more time intervals that correspond to a fraction of a day in answer to a related secondary question. The time intervals may include night, morning, afternoon and evening, where night is between 12 am and 5.59 am, morning is between 6 am and 11.59 am, afternoon is between 12 pm and 5.59 pm and evening is between 6 pm and 11.59 pm.

The questionnaire data structure 800 may include fewer or additional questionnaire modules. One or more of the questionnaire modules may include one or more questions corresponding to feedback from at least the first individual and/or suggestions for additional variables to be tracked (information to be collected) and/or analyzed. Such feedback may allow a knowledge base to grow and improve as the approach is scaled to more individuals. Two or more questionnaire modules may be combined. Some pre-determined questions may be included in more than one questionnaire modules. One or more questionnaire modules may include fewer or more pre-determined questions. In some embodiments, one or more pre-determined questions may be moved from one questionnaire module to another.

As noted previously, the subset of pre-determined questions may be varied during the data-collection time interval, i.e., the questionnaire may be used dynamically. The varying may be in accordance with the configuration instructions 420 (FIG. 4), with providing one or more pre-determined questions 354 in FIGS. 3 and 4 (for example, in a data stream that is transmitted and stored in the memory device 324 in FIG. 3), with providing instructions corresponding to one or more pre determined questions (such as in instructions corresponding to one or more web pages 412 in FIG. 4), and/or with providing the optional memory device 524 in FIG. 5 containing one or more pre-determined questions 354.

In some embodiments, an initial phase of the data-collection time interval may, at least in part, correspond to a training phase, for at least the first individual (i.e., how to answer the pre-determined questions), for one or more of the apparatuses, and/or for one or more algorithms implementing the questionnaire (for example, how best to determine the one or more temporal onsets for at least the first individual). During the training phase, the subset of pre-determined may initially include one or more pre-determined questions selected from the premonitory questions 820, the migraine questions 822 and/or the medicine usage questions 824.

The questionnaire, and the related statistical analysis (described below with reference to FIGS. 9–14), may be applied iteratively. For example, pre-determined questions in one or more of the questionnaire modules may be tree-based or hierarchical, ranging from general or broad in scope to narrow or specific in scope. General pre-determined questions may be asked one or more times during the data-collection time interval. Based on one or more answers to these general pre-determined questions, additional narrow pre-determined questions may be asked one or more times. In some embodiments, the subset of pre-determined questions may be asked, one or more association variables (for example, migraine triggers) may be identified and at least the first individual may exclude one or more of the identified association variables (for example, by modifying behavior, changing diet, etc.). This process of asking, identifying and excluding may be repeated one or more times until diminishing returns (for example, it may become difficult to readily and/or reliably identify one or more additional association variables).

Figure 8B:
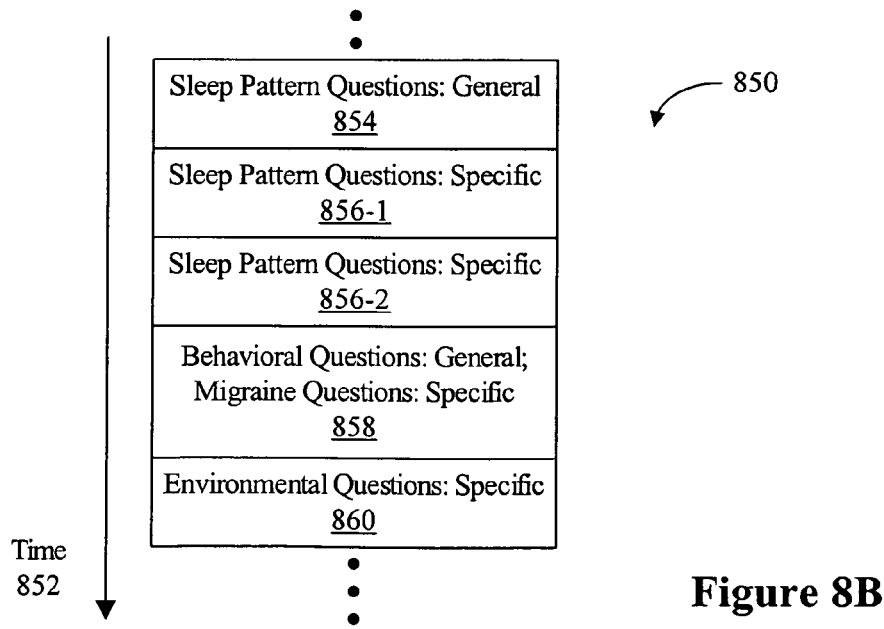
FIG. 8B is a block diagram illustrating an embodiment of a questionnaire.

FIG. 8B is a block diagram illustrating an embodiment of a questionnaire 850 that is dynamic and hierarchical. One or more pre-determined questions in question modules are included in the subset of pre-determined questions as a function of time 852. General sleep pattern questions 854 may be included. Specific sleep pattern questions 856 may be included on two occasions. General behavioral questions and specific migraine questions 858 may be included. Specific migraine questions 860 may be included. The questionnaire 850 is meant to be illustrative of a dynamic questionnaire and is not indicative of a specific implementation. Thus, there may additional or fewer portions of question modules, additional or fewer question modules, an order or two or more of the question modules may be changed, at least a portion of two or more the question modules may be combined, and/or at least a portion of one or more additional question modules may be included at any instance in time.

In order to reduce or eliminate inaccuracies associated with memory or recall errors, in some embodiments at least the first individual may not be able to answer or modify answers in one or more subsets of pre-determined questions, such as those in the questionnaire 850, that were asked at previous instances in time, for example, on one or more previous days.

Figure 9A:
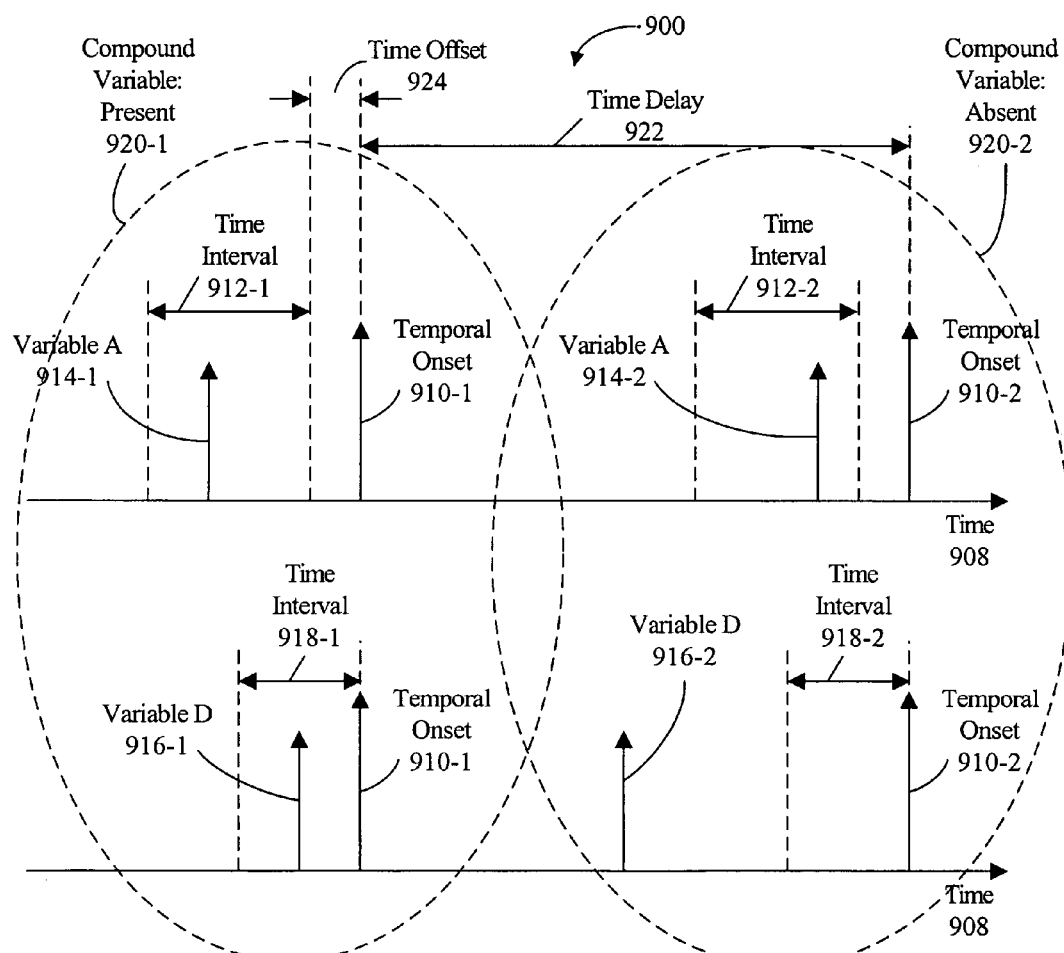
FIG. 9A is a block diagram illustrating an embodiment of determining a compound variable associated with events having different temporal onsets.

Attention is now directed towards embodiments of the statistical analysis, including the determination of one or more statistical relationships between one or more temporal onsets and one or more variables and/or one or more compound variables, and the identification of one or more association variables. The statistical analysis may include classification and/or regression (such as determining a model of the temporal onsets including one or more variables and/or one or more compound variables with corresponding weights). FIG. 9A is a block diagram illustrating an embodiment 900 of determining a compound variable 920 associated with events having different temporal onsets 910. In some embodiments, the events may be migraine attacks and the temporal onsets 910 may be onset times for migraine attacks. Temporal onsets 910 are shown as a function of time 908. The temporal onsets 910 may include one or more onset times and/or one or more onsets during one or more time windows or time intervals. There is a time delay 922 between temporal onset 910-1 and temporal onset 910-2. An inverse of the time delay 922 may correspond to a frequency of the events. Patterns of occurrence of variable A 914 and variable D 916, including instances or entries corresponding to presence information (illustrated by arrows) and corresponding to absence information (illustrated by absences of arrows), as function of time 908 are illustrated on separate but identical axes for clarity.

The compound variable 920 may correspond to at least a pattern of occurrence of variable A 914 during a first time interval 912 preceding the temporal onsets 910 and a pattern of occurrence of variable D 916 during a second time interval 918 preceding the temporal onsets 910. Note that in embodiment 900, the first time interval 912 may be offset 924 from the temporal onsets 910. In some embodiments, the first time interval 912, the second time interval 918, and/or additional time intervals corresponding to additional variables may be offset from the temporal onsets 910. In some embodiments, a pattern of occurrence of at least one variable may be in accordance with one or more time intervals having a width that corresponds to a precision of a time measurement, i.e., each of the one or more time stamps corresponds to a respective time.

In some embodiments, the first time interval 912, the second time interval 918, and/or other time intervals may have the same duration and/or offsets 924. In some embodiments, the first time interval 912, the second time interval 918, and/or other time intervals may have a different duration and/or offsets 924. In some embodiments, one or more of the time intervals may be adjustable. In exemplary embodiments, the time intervals may have a duration of a fraction of a day (such as 1, 2, 3, 4, 6, 12, and/or 18 hours), one day, two days, three days, more days, and/or combinations of these items. In some embodiments, offsets, such as offset 924, may be between 0 and up to 3, 5, and/or 10 or more days. In exemplary embodiments, the offset 924 may be a fraction of a day (such as 1, 2, 3, 4, 6, 12, and/or 18 hours), one day, two days, three days, more days, and/or combinations of these items.

A respective instance or entry for the compound variable 920, such as compound variable 920-1, may correspond to a presence if variable A is present during the first time interval 912-1 (a presence entry in the pattern of occurrence of variable A 914) and variable D is present during the second time interval 918-1 (a presence entry in the pattern of occurrence of variable D 916). Alternatively, a respective instance or entry for the compound variable 920, such as compound variable 920-2, may correspond to an absence if variable A is absent during a first time interval 912-2 (an absence entry in the pattern of occurrence of variable A 914) and/or variable D is absent during a second time interval 918-2 (an absence entry in the pattern of occurrence of variable D 916).

In an exemplary embodiment, entries for the pattern of occurrence of variable A 914 during the first time interval 912 and the pattern of occurrence of variable D 916 during the second time interval 918 may be categorical or may be converted from quantitative to categorical by partitioning using one or more thresholds. In some embodiments, different thresholds may be used for different variables. In some embodiments, one or more compound variables may be a weighted summation of one or more variables. The resulting one or more compound variables may be converted into categorical data using one or more thresholds and/or one or more quantitative variables may be converted into categorical data using one or more thresholds prior to generating one or more compound variables using a weighted summation.

Note that entries in the patterns of occurrence for categorical variables are typically represented by codes. For categorical variables having two class or categories, a single binary digit may be used, such as 0 or 1, or −1 or 1. When there are more than two categories, such as with ordered categorical variables, a dummy variable having K values or bits may be used. Entries for the compound variable 920 may determined by performing an operation and/or a logical operation on corresponding entries in the pattern of occurrence of the variable A 914 and the pattern of occurrence of the variable D 916. The operation may include multiplication. The logical operation may include a Boolean operation, such as AND. A wide variety of coding approaches, however, may be used in different embodiments for representing presence and absence information in the pattern of occurrence of variable A 914 and the pattern of occurrence of variable D 916. Therefore, in some embodiments the logical operation may include AND, OR, NOT, XOR, as well as combinations of these operations.

While FIG. 9A illustrates two variables, in some embodiments 3 or more variables may be used to determine the pattern of occurrence (including presence and absence information) for the compound variable 920. While a respective variable has a corresponding time interval and offset (which may be zero or finite), in some embodiments at least two variables may have time intervals having the same duration and/or the same offset. Similarly, while FIG. 9A illustrates 2 temporal onsets 910, in some embodiments there may be one temporal onset 910 or 3 or more temporal onsets 910, which may be used in determining the pattern of occurrence of the compound variable 920.

Figure 9B:
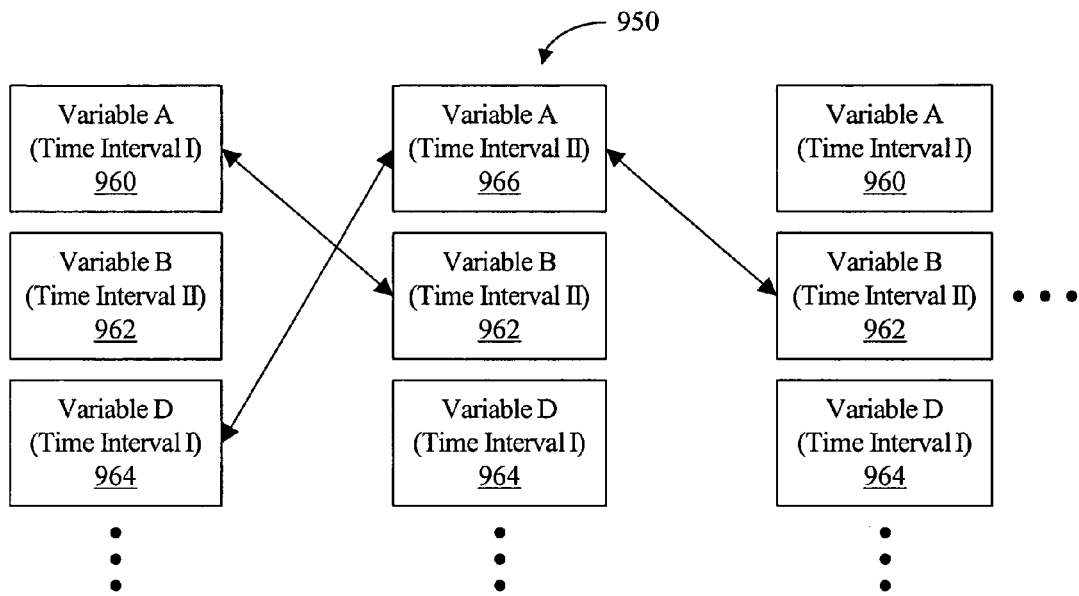
FIG. 9B is a block diagram illustrating an embodiment of determining compound variables.

FIG. 9B is a block diagram illustrating an embodiment 950 that summarizes the determining of compound variables. Logical operations are performed on the patterns of occurrence of one or more subsets of variables, such as variable A (during time interval I) 960 and variable B (during time interval II) 962, and variable D (during time interval I) 964, variable A (during time interval II) 966 and variable B (during time interval II) 962.

A number of variables included in determining a respective compound variable is henceforth referred to as an order n. FIG. 9B illustrates determination of a compound variable of order 2 and a compound variable of order 3. In some embodiments, a respective variable during a time interval, such as variable D (during time interval I) 964, may be included once in determining a respective compound variable, i.e., multiple instances of the respective variable during the time interval may not be included in determining the respective compound variable. However, the respective variable may be included more than once in determining the respective compound variable if different time intervals are used, such as variable A (during time interval I) 960 and variable A (during time interval II) 966. In some embodiments, there may be additional or fewer variables, i.e., the order may be 1 (a respective compound variable is merely a variable) or 4 or more. In some embodiments, time interval I may correspond to a duration of 24 hours with an offset 924 (FIG. 9A) of zero from the temporal onsets 910 (FIG. 9A). Time interval II may correspond to a duration of 24 hours with an offset 924 (FIG. 9A) of 48 or 72 hours from the temporal offsets 910 (FIG. 9A). In some embodiments, there may be additional or fewer variables included in a respective compound variable, and/or there may be fewer or additional time intervals.

Referring back to FIG. 9A, as discussed further below one or more statistical relationships between the patterns of occurrence of one or more compound variable, such as compound variable 920, and/or the pattern of occurrence of one or more of the variables, such as variable A 914, and the temporal onsets 910 may be determined. In the case of migraines, however, one or more temporal onsets 910 corresponding to one or more rebound headaches, one or more recurrence headaches, and/or one or more tension headaches may be excluded during the determining of the one or more statistical relationships. This may improve the results of the statistical analysis. For example, the one or more rebound headaches may be identified in accordance with a medicine usage history for pharmacological agents, such as analgesics and/or triptans. In some embodiments, the one or more rebound headaches may be identified, at least in part, if there is no pain-free period between migraines attacks.

Figure 10:
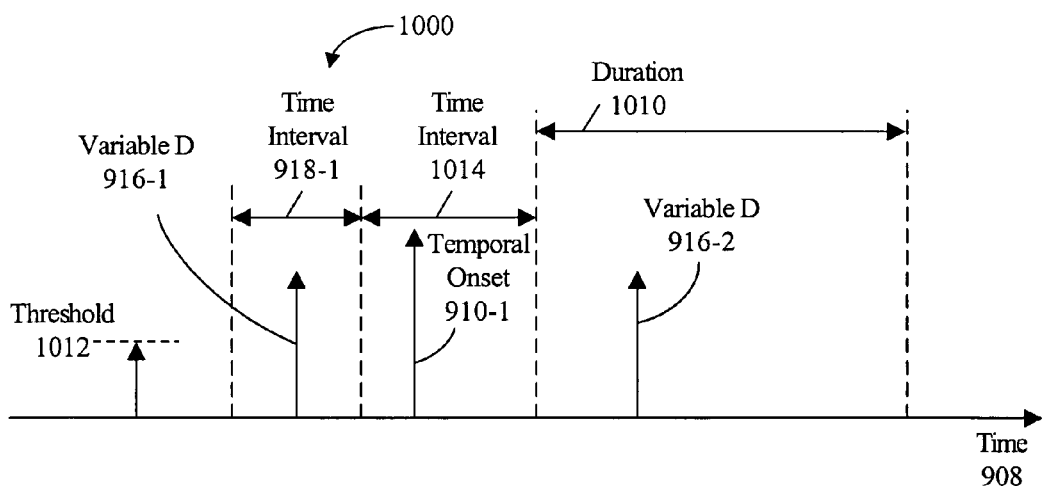
FIG. 10 is a block diagram illustrating an embodiment of a variable occurring during a duration of an event.

In addition, entries in the pattern of occurrence of one or more variables that occur during the duration of an event, such as a migraine, may be excluded in determining one or more compound variables and/or one or more statistical relationships. The reason for this exclusion operation may be that such entries, corresponding to the presence of one or more variables, may not trigger an event since an event is already occurring. Said differently, it may not be possible to initiate something that is already occurring. FIG. 10 is a block diagram illustrating an embodiment 1000 with a variable D 916-2 occurring during a duration 1010 of a migraine. As a consequence, the presence of variable D 916-2 may be excluded from the determining of compound variable 920 (FIG. 9A) and/or one or more statistical relationships, such as those between temporal onsets 910 and the pattern of occurrence of the compound variable 920 (FIG. 9A) and/or between temporal onsets 910 and the pattern of occurrence of variable D 916. Note that the temporal onset 910-1 is illustrated as occurring during a time interval 1014. In some embodiments, the temporal onset 910-1 corresponds to an onset time (i.e., a specific time). In alternate embodiments, the duration 1010 may be defined with respect to a beginning of the time interval 1014, a center of the time interval 1014, or the onset time corresponding to the temporal onset 910-1. Embodiment 1000 also illustrates a threshold 1012 that may be used to convert a quantitative variable into a categorical variable by partitioning. In other embodiments, one or more thresholds may include one or more geographic directions. While embodiments 900 (FIG. 9A) and 1000, illustrate variables, such as the variable D 916, occurring in time intervals 912 (FIG. 9A), 918 (FIG. 9A) and 1014 preceding corresponding temporal onsets 910, in some embodiments one or more occurrences of one or more of the variables in one or more time intervals corresponding to one or more temporal onsets 910, i.e., one or more time intervals containing both a respective temporal onset and at least a respective variable, may be included when determining one or more of the statistical relationships.

A wide variety of computational techniques may be used to determine the one or more statistical relationships, including one or more parametric analysis techniques, one or more non-parametric analysis techniques, one or more supervised learning techniques and/or one or more unsupervised learning techniques. In some embodiments, one or more non-parametric analysis techniques may be used. As noted previously, non-parametric analysis techniques make few assumptions about an existence of a probability distribution function, such as a normal distribution, corresponding to a population from which samples or entries are obtained, or regarding independence of the variables and/or the compound variables. In general, non-parametric analysis techniques may use rank or naturally occurring frequency information in the data to draw conclusions about the differences between populations.

The one or more non-parametric analysis techniques may perform hypothesis testing, i.e., to test a statistical significance of a hypothesis. In particular, the one or more non-parametric analysis techniques may determine if the one or more temporal onsets and the one or more compound variables and/or one or more variables are statistically independent (or dependent) in accordance with a statistical significance criterion. One or more variables and/or one or more compound variables having a statistically significant relationship with the temporal onsets may be used to identify one or more association variables. In the case of migraines, the one or more association variables may be migraine triggers or potential migraine triggers.

In exemplary embodiments, the non-parametric analysis technique may include a chi-square analysis technique, a log-likelihood ratio analysis technique (also referred to as G-test), and/or a Fisher's exact probability analysis technique. In addition to their other advantages, these techniques may be well suited to analyzing an underdetermined problem (i.e., sparse sampling in a multi-dimensional variable space), in which there may be a plurality of variables and/or compound variables and a limited number of entries or samples.

The chi-square analysis technique, the log-likelihood ratio analysis technique, and the Fisher's exact probability analysis technique may be determined using a cross-tabulation or contingency tables (sometimes referred to as bivariate tables). The Fisher's exact probability analysis technique computes the sum of conditional probabilities of obtaining the observed frequencies in a respective contingency table and the conditional probabilities of obtaining exactly the same observed frequencies for any configuration that is more extreme (i.e., having a smaller conditional probability). The chi-square ($\chi^2$) may be determined using $$\chi^2 = \sum_i \frac{(O_i - E_i)^2}{E_i},$$

and the log-likelihood ratio (LLR) using $$LLR = \sum_i O_i \ln\left(\frac{O_i}{E_i}\right),$$

where the summation is over the entries in the respective contingency table, $O_i$ is the i-th observed frequency value, and $E_i$ is the i-th expected frequency value. The following example illustrates an embodiment of determining a statistical relationship using the log-likelihood ratio.

Consider the data in Table IV. The first column contains the number of entries in the pattern of occurrence where a variable or compound variable is present during a time interval, such as the first time interval 912 (FIG. 9A), and a temporal onset is present after a time offset, such as the time offset 924 (FIG. 9A) (henceforth denoted by $X_{11}$) plus the number of entries in the pattern or occurrence where the variable or compound variable is absent during the time interval and a temporal onset is absent after the time offset (henceforth denoted by $X_{00}$). $X_{11}$ is sometimes referred to as a true-true and $X_{00}$ is sometimes referred to as a false-false. $X_{11}$ and $X_{00}$ are henceforth referred to as co-occurrences.

The second column contains the number of entries in the pattern of occurrence where the variable or compound variable is present during the time interval and a temporal onset is absent after the time offset (henceforth denoted by $X_{10}$) plus the number of entries in the pattern of occurrence where the variable or compound variable is absent during the time interval and a temporal onset is present after the time offset (henceforth denoted by $X_{01}$). $X_{10}$ is sometimes referred to as a true-false and $X_{01}$ is sometimes referred to as a false-true. $X_{10}$ and $X_{01}$ are henceforth referred to as cross occurrences.

TABLE IV

An embodiment of a contingency table.

| Number of Co-Occurrences ($X_{11} + X_{00}$) | Number of Cross Occurrences ($X_{10} + X_{01}$) |
|---|---|
| 46 | 11 |

If the variable or the compound variable and the temporal onsets are completely independent, the expected frequency values for each column, $E_1$ and $E_2$, would equal 28.5, one half of the sum of the number of co-occurrences and cross-occurrences, i.e., the total number of observations (data points or samples) in Table IV. Therefore, for Table IV $$LLR = 2 \cdot 46 \ln\left(\frac{46}{28.5}\right) + 2 \cdot 11 \ln\left(\frac{11}{28.5}\right) = 44.04 - 20.94 = 23.10.$$

A one-sided minimal statistical significance confidence criterion of 5% ($\alpha=0.05$) or statistical confidence threshold based on the number of degrees of freedom (the size of the contingency table) corresponds to an LLR of 3.841. Since the LLR for Table IV is greater than 3.841, it is statistically significant. From a statistical significance perspective, therefore, the temporal onsets and the pattern of occurrence of the variable or compound variable in this example are dependent. Note that the determination of the statistical relationship for the temporal onsets and the variable or the compound variable in this embodiment uses presence and absence information in the pattern of occurrence of the variable or compound variable. In some embodiments, one or more of the statistical relationships may be determined using presence information, i.e., the presence of one or more variables or one or more compound variables during one or more time intervals, without using absence information. In alternate embodiments, a wide variety of analysis techniques may be used to determine the one or more statistical relationships, including one or more non-parametric analysis techniques and one or more parametric analysis techniques.

In parametric analysis, a Pearson's product-moment correlation coefficient r may be useful in summarizing a statistical relationship. For some contingency tables, Cramer's phi $\phi$, the square root of $\chi^2$ or the LLR divided by the number of observations N, may have a similar interpretation to r (although, it is known that Cramer's phi $\phi$ may underestimate r). In the example illustrated in Table IV, $$\varphi = \sqrt{\frac{LLR}{N}} = \sqrt{\frac{23.1}{57}} = 0.64.$$

The chi-square analysis technique and the log-likelihood ratio analysis technique may have a maximal sensitivity for contingency tables based on patterns of occurrence of variables or compound variables having 50% presence entries and 50% absence entries. In addition, in embodiments where temporal onsets, such as temporal onsets 910 (FIG. 9A), correspond to onsets during one or more time windows or time intervals, maximal sensitivity may occur if 50% of these time windows or time intervals have a temporal onset (i.e., a presence entry). In some embodiments, one or more contingency tables may be generated to achieve approximately 50% presence entries for patterns of occurrence of one or more variables or one or more compound variables, and/or 50% temporal onsets by using a subset of the collected information or data. In an exemplary embodiment, one or more contingency tables may be generated by approximately randomly (including the use of a pseudo-random number generator or algorithm) selecting a subset of the temporal onsets, and/or approximately randomly selecting a subset of the presence or absence entries of one or more patterns of occurrence of one or more variables or one or more compound variables such that the one or more contingency tables may have approximately 50% presence entries and 50% absence entries distributed over $X_{00}$, $X_{11}$, $X_{10}$, and $X_{01}$. For infrequently occurring events, variables, and/or compound variables, there may be more absence entries than presence entries in the collected data or information. As a consequence, different sampling ratios may be used for presence and absence entries.

In some embodiments, boosting may be used when generating one or more contingency tables. The fraction of the collected information may be approximately randomly sampled to generate one or more contingency tables. A respective contingency table may be generated N times using approximate random sampling. Statistical relationships for at least M of these N contingency tables may be used (including combining and/or averaging) to determine whether or not the temporal onsets and the corresponding variable or compound variable are independent. In an exemplary embodiment, N may be 5, 10, 25, 50, 100 or more. M may be 50% (rounded to the nearest integer), 60%, 66%, 70%, 75%, 80% or more of N.

In some embodiments, there may be too few presence entries or too many presence entries in one or more patterns of occurrence of one or more variables or compound variables to reliably determine statistically significant independence (or dependence) from the temporal onsets. As a consequence one or more of these variables or one or more of these compound variables may be excluded when determining one or more statistical relationships. In an exemplary embodiment, one or more variables or one or more compound variables having patterns of occurrence with less than 10% presence entries or more than 85% presence entries may be excluded. To assist in obtaining sufficient presence and absence entries, in some embodiments at least the first individual may be instructed to vary their activities and/or diet from day to day during the data collection time interval.

Figure 11:
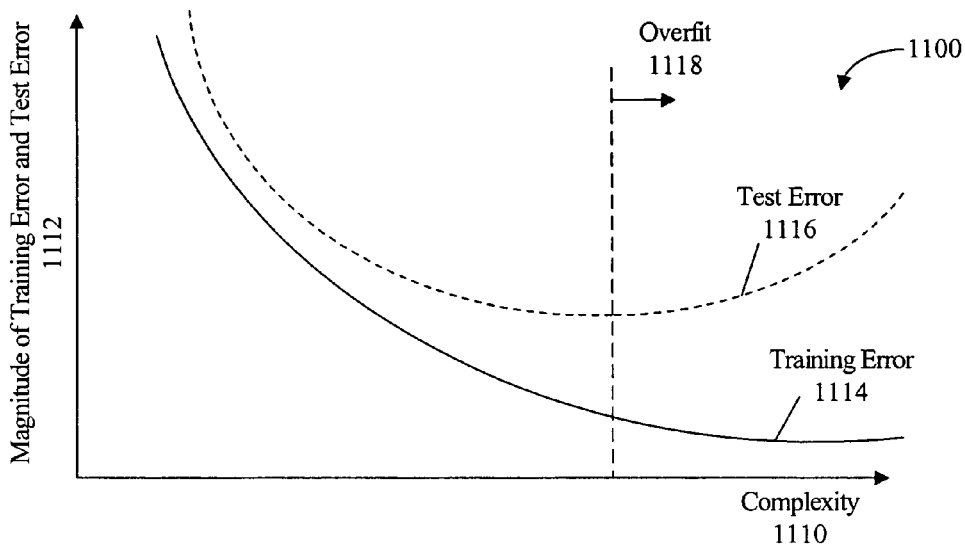
FIG. 11 is a block diagram illustrating an embodiment of determining model complexity.

Overfitting is a risk when developing a model in a statistical learning problem. In some embodiments, this risk may be addressed by using a fraction or percentage of the collected data or information (patterns of occurrence and temporal onsets) for training, i.e., to develop the model, and a remainder for testing the resulting model. This is illustrated in FIG. 11, which is a block diagram illustrating an embodiment 1100 of determining model complexity. In some embodiments, the model complexity may correspond to a number of variables or compound variables that have statistically significant dependence on the temporal onsets. In some embodiments, the model complexity may, at least in part, correspond to a number of variables included in a respective compound variable, i.e. the order n. Embodiment 1100 shows a magnitude of a training and/or a test error 1112 as a function of model complexity 1110. A training error 1114 typically decreases as the model complexity 1110 increases (the model better fits or predicts a training set of data). A test error 1116 typically exhibits a minimum. Additional model complexity 1110 beyond this point does not generalize well (the model offers a poorer fit or prediction for a test set of data). Beyond this point, therefore, the training set of data may be overfit 1118. In an exemplary embodiment, the percentage of the collected information used for training may be 70%, 75%, 80%, 85% or 90%.

An additional metric of the model complexity may be determined. This metric may be used in conjunction with or independently of the training set of data and the test set of data. The additional metric is described below. In some problems and/or embodiments, determining one or more statistical relationships for one or more variables (or, said differently, one or more compound variables of order 1) may not be sufficient to determine statistically significant independence (or dependence) with respect to the temporal onsets. For example, in multi-dimensional problems, where exposure to two or more variables in at least close temporal proximity may be necessary to initiate a temporal onset (such as a migraine), a value of the Fisher's exact probability, $\chi^2$, and/or LLR for a compound variable of order 1 may be reduced since there is a penalty for the presence of the cross occurrences, $X_{10}$ and $X_{01}$.

More generally, the value of the Fisher's exact probability, $\chi^2$, and/or LLR may be reduced if the order n of one or more compound variables is less than an intrinsic order of the multi-dimensional problem. In the case of $X_{10}$, a temporal onset may or may not occur unless a certain number of variables or a set of variables (which may be inter-operative) are present in close temporal proximity. And in the case of $X_{01}$, more than one set of variables may be present, i.e., one or more variables in another set of variables may have triggered the corresponding temporal onsets. As illustrated in FIG. 7, in the embodiments for migraines there may also be variations in a patient's sensitivity threshold to a variable or one or more sets of variables as a function of time.

To assess whether or not the model has sufficient complexity, i.e., whether or not one or more compound variables have been determined to sufficient order n, a ratio R may be determined. R is defined as $X_{11}$ divided by the total number of occurrences of the variable or compound variable of order n, i.e., $$R = \frac{X_{11}}{(X_{11} + X_{10})}.$$

An increasing value of R, and/or Cramer's phi $\phi$, as statistical analysis is performed to higher order (i.e., n+1) may be metrics of goodness, i.e., it may indicate that the higher order does a better job determining statistically significant independence or dependence between one or more compound variables and the temporal onsets. In some embodiments, contingency tables for one or more compound variables may be generated for progressively higher orders. Once the ratio R is close to or equal to one, i.e., $X_{10}$ is close to or equal to zero, further increases in the order of one or more compound variables may not be needed, i.e., the model has sufficient complexity.

One or more variables and/or compound variables having statistically significant statistical relationships with the temporal onsets may be identified as one or more association variables. For a respective compound variable or order n having a significant statistical relationships with the temporal onsets, the n constituent variables may be identified as n association variables and/or as a set of association variables.

In some embodiments, one or more statistically significant compound variables of order n having the ratio R approximately equal to 1 may be identified as one or more association variables. In the embodiments for migraines, one or more association variables may be one or more migraine triggers or one or more probable migraine triggers.

In some embodiments, one or more compound variables of order n and/or one or more constituent variables in the one or more compound variables of order n may be ranked in accordance with the corresponding determined statistical relationships that are statistically significant. In some embodiments, a ranking of a respective constituent variable is in accordance with a number of occurrences of the respective constituent variable in one or more compound variables of order n having statistical relationships that are statistically significant. Ranking may be performed as the statistical significance confidence criterion ($\alpha$) is progressively increased.

In exemplary embodiments, $\alpha$ may be 0.05 or lower. For a respective ranking, a pareto corresponding to at least a subset of the respective ranking may be defined. The pareto may correspond to variables or compound variables having a statistical relationship or a number of occurrences exceeding a threshold. In some embodiments, a top 10, 20, 50 or 100 variables or compound variables may be used, or a plurality of the top 10, 20, 50 or 100 variables or compound variables may be used. For compound variables of order n, approximate stability of the pareto as the statistical significance confidence criterion is increased may be used to identify a noise floor. Approximately stability may include an approximately unchanged order n in the ranking or a presence of approximately the same variables (for example, more than 70%) in the ranking. In exemplary embodiments, the noise floor may correspond to an $\alpha$ of 0.01 or lower, an $\alpha$ of 0.001 or lower, or an $\alpha$ of 0.0001 or lower. One or more variables and/or one or more compound variables in paretos corresponding to one or more statistical significance confidence criteria that exceed the noise floor may be identified as association variables.

In some embodiments, one or more variables and/or one or more compound variables in paretos corresponding to one or more statistical significance confidence criteria that exceed the noise floor may be used as a seed set in a subsequent statistical analysis. The subsequent statistical analysis may determine statistical relationships for compound variables of a higher order. In some embodiments, the subsequent analysis may utilize an analysis technique such as SVM or CART. These and other analysis techniques are discussed further below.

Figure 12:
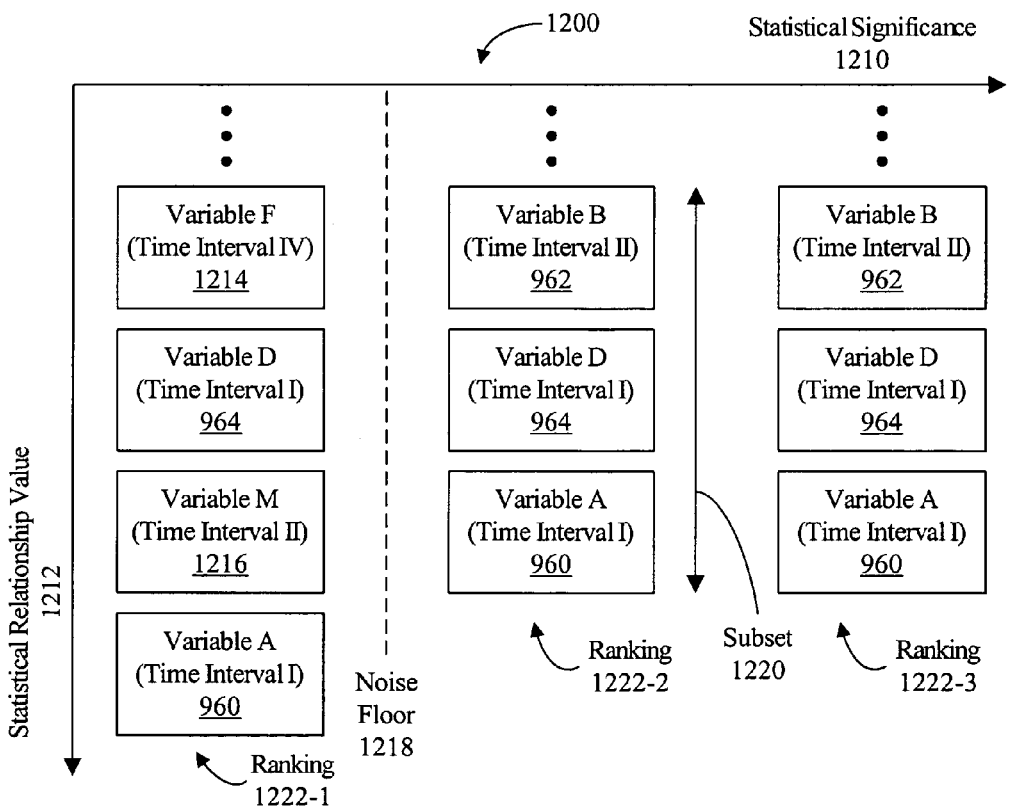
FIG. 12 is a block diagram illustrating an embodiment of ranking variables.

FIG. 12 is a block diagram illustrating an embodiment of ranking variables 1200. Statistical relationship value 1212 is plotted as a function of statistical significance 1210, such as the statistical significance confidence criteria. Several rankings 1222 are illustrated. Ranking 1222-1, including variable F (during time interval IV) 1214 and variable M (during time interval II) 1216, is below a noise floor 1218. Ranking 1222-2 and ranking 1222-3 are above the noise floor 1218. A subset 1220 of ranking 1222-2 and ranking 1222-3 is stable. The subset 1220 may identified as the pareto.

In an exemplary embodiment for migraines, the noise floor 1218 corresponds to an $\alpha$ of approximately 0.001. At least 8 of the top-10 variables in paretos for more stringent statistical significance confidence criteria than that corresponding to the noise floor 1218 are present even when an approximately random subset corresponding to 80% of the patterns of occurrence and the temporal onset data is used. Excluding probable recurrence headaches, rebound headaches and tension headaches increases the statistical relationship values 1212 for compound variables having an order n corresponding to the pareto. Compound variables of at least order 4 have ratio R values approximately equal to 1.

Having identified one or more association variables for at least the first individual, one or more additional association variables may identified. For example, if one or more groups of association variables have been previously determined for one or more other individuals, the one or more association variables identified for at least the first individual may be used to associate at least the first individual with one or more of these groups. In this way, one or more of the association variables in one or more of the groups may be identified as additional association variables for at least the first individual. For example, the one or more additional association variables may be groups of migraine triggers and at least the first individual may be associated (classified) with one or more of these groups in accordance with one or more identified migraine triggers for at least the first individual.

Alternatively, additional association variables may be identified by associating the identified one or more association variables for at least the first individual with previously determined groups of variables. For example, the identified one or more association variables for at least the first individual may be foods and additional association variables may be identified by associating the foods with corresponding food groups, such as pine-apple, mushroom, melon, cashew, banana, or citrus, or groups determined based on an amount of constituent elements (minerals, fats, carbohydrates, and/or proteins) in foods. For example, if an identified association variable is in the beet family or the citrus family, other members of the beet or citrus families may be identified as association variables.

Figure 13:
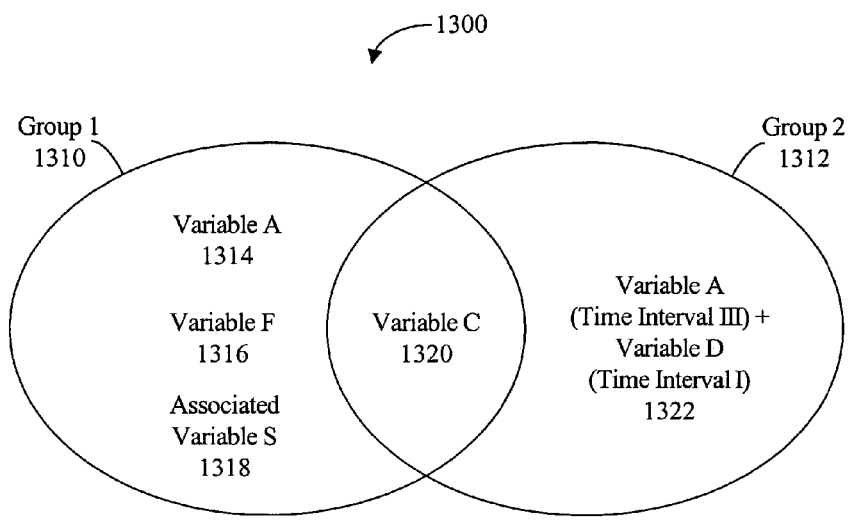
FIG. 13 is a block diagram illustrating an embodiment of associating one or more variables with one or more groups of variables.

FIG. 13 is a block diagram illustrating an embodiment 1300 of associating one or more variables with one or more groups of variables. Group I 1310 may include variable A 1314, variable F 1316, associated variable S 1318, and variable C 1320. Group II 1312 may include variable C 1320 and a compound variable 1322, including variable A (during time interval III) plus variable D (during time interval I). If a variable, such as variable A 1314, is determined or identified, one or more of the other variables in group I 1310 may be identified. In some embodiments, there may be additional groups, there may or may not be overlap (such as variable C 1320) between two or more of the groups, and/or a respective group may include fewer or more variables, fewer or more associated variables, and/or fewer or more compound variables.

Having identified one or more association variables in accordance with one or more statistical relationships, rankings, and/or associated groups of associated variables, one or more recommendations and/or one or more reports may be provided to at least the second individual and/or at least the first individual. In an exemplary embodiment, the one or more recommendations may include a listing of one or more migraine triggers and/or one or more probable migraine triggers for at least the first individual. The one or more recommendations may include one or more variables for which the statistical analysis was unable to determine a statistically significant relationship. In some embodiments, the one or more recommendations may indicate one or more migraine triggers and/or one or more probable migraine triggers that at least the first individual may wish to modify (such as for behaviors) and/or avoid. The one or more recommendations may indicate additional analysis that may be advisable in accordance with one or more of the statistical relationships and/or the one or more association variables. One or more corresponding reports may include the one or more recommendations. The one or more reports may include a summary for at least the first individual. The summary may include a health overview for at least the first individual during at least a portion of the data-collection time interval. In the case of migraines, the health overview may include a summary of migraine frequency, migraine severity and/or the use of one or more pharmacological agents, such as one or more acute therapies and/or one or more preventive therapies.

In some embodiments, the one or more recommendations may include placebo information, for example, placebo migraine triggers. After this placebo information is provided to at least the first individual (possibly via an intermediary such as at least the second individual), an impact on at least the first individual may be determined. For example, migraine frequency, migraine severity, and/or use of pharmacological agents during a subsequent time interval may be determined. An efficacy of the identified association variables may be determined by comparing these metrics with those that occur when non-placebo information is used, i.e., when actual association variables are provided to at least the first individual. The difference of these two metrics can be used to define a therapeutic gain. In some embodiments, the therapeutic gain may be determined by averaging results for two or more individuals such as at least the first individual.

Attention is now given to other techniques of performing statistical analysis, such as determining the one or more statistical relationships. As discussed previously, one or more variables or one or more compound variables determined during the statistical analysis, for example, in one or more paretos, may be used in subsequent analysis. In some embodiments, the subsequent analysis may utilize a non-parametric analysis technique as an initial or first stage. In other embodiments, the subsequent analysis may not utilize a non-parametric analysis technique. The subsequent analysis may be used as the initial or first stage, to refine the model (including adding or removing one or more variables and/or one or more compound variables), and/or identify one or more association variables. The subsequent analysis may include classification and/or regression (such as determining a model of the temporal onsets including one or more variables and/or one or more compound variables with corresponding weights). As with the initial statistical analysis, a wide variety of techniques may be used in the subsequent analysis. Two such techniques, SVM and CART, are described further below.

Embodiments of SVM are instances of supervised learning techniques that may be applied to classification and regression problems. For binary classification, a set of binary labeled data points (training data or examples) is provided. SVMs may be used to determine an optimal separation boundary, defined by the variables and/or compound variables, between two classes of data points. A separation boundary is optimal if using it as a decision rule to classify future data points minimizes an expected classification error. For linearly separable data sets (i.e., a class of absences, which may be indicated by −1, and a class of presences, which may be indicated by +1, may be separated by a line in 2 dimensions, or a so-called hyperplane in higher dimensions), SVMs may be used to determine a maximal margin hyperplane. For the maximal margin hyperplane, a linear decision boundary may be positioned such that it separates both classes and such that the distance to the closest point from each class is maximized. For non-linearly separable data sets, some training data points may be allowed on the opposite or "wrong" side of the hyperplane, i.e., a classification error on the training data set may be allowed and may be minimized, while the margin, measured between points on the "correct" side of the hyperplane, is maximized.

If a linear decision boundary is not sufficiently complicated to model the separation between classes accurately, the corresponding linear model may be transformed into a non-linear model by non-linearly transforming the variables and/or compound variables into a possibly higher dimensional Euclidean space. A linear decision boundary constructed in such a higher dimensional Euclidean space may correspond to a non-linear decision boundary in the original space of variables and/or compound variables. This approach is referred to as kernel SVM.

Depending on how the margin and training error are measured, and how a trade-off between maximizing the margin and minimizing the training error is established, different types of SVMs may be obtained. In some embodiments, SVM may include standard 1-norm SVM (measuring the margin using Euclidean distance, i.e., a $L_2$-norm, and the training error using a $L_1$-norm), standard 2-norm SVM (measuring the margin using Euclidean distance, i.e., the $L_2$-norm, and the training error using the $L_1$-norm), and/or LP-SVM (measuring the margin using the $L_1$-norm and the training error using the $L_1$-norm). Each of these 3 types of SVM may be a C-type or nu-type SVM. These two varieties correspond to different ways of trading-off maximizing the margin against minimizing the training error. The 1-norm SVM, standard 2-norm SVM, and/or LP-SVM may be a C+/C− or nu+/nu− type (when errors on positive (+1) labeled training data are weighted differently than errors on negative (−1) labeled training data).

The principle for binary classification described above may be extended to regression, for example, by copying the regression data twice, shifting both copies in opposite directions (over a distance epsilon) with respect to the continuous output dimension or variable and establishing a regression surface as a decision boundary between the two shifted copies that may be regarded as two classes for binary classification. As a consequence, in some embodiments, regression versions of SVMs corresponding to previously described SVMs may be used.

The decision boundary determined using one or more SVMs may be used to discriminate between temporal onsets and non-temporal onsets. For binary classification, measures of goodness for the resulting model include a prediction accuracy that is better than predicting 50% of the positive data (i.e., occurrences, which may be indicated by a +1) as positive (i.e., true positive predictions) and better than predicting 50% of the negative data (i.e., absences, which may be indicated by a −1) as negative (i.e., true negative predictions). Doing better than 50/50 corresponds to doing better than random. In an exemplary embodiment, the resulting model successfully predicts at least 80–85% of the true-false ($X_{10}$) and false-false events ($X_{00}$), i.e., the true negatives, while predicting significantly more than 50% of the true positives correctly, i.e., false-true (false-true ($X_{01}$) and true-true events ($X_{11}$)).

CART is non-parametric multivariate analysis technique. It involves the determination of a binary decision tree using the training set of data. Predictions based on the resulting tree may be compared to the test set of data (cross validation). A decision tree provides a hierarchical representation of the feature space in which explanatory variables are allocated to classes (such as temporal onsets or non-temporal onsets) according to the result obtained by following decisions made at a sequence of nodes at which branches of the tree diverge. Branches or divisions of the tree may be chosen to provide the greatest reduction in the entropy of the variables (for a classification tree based on categorical data), such as a small or zero standard deviation, or the greatest reduction in the deviation between the variables (and/or compound variables) and one or more variables being fit (for a regression tree based on quantitative data). A tree stops growing when no significant additional reduction can be obtained by division. A node that is not further sub-divided is a terminal node. It is associated with a class. A desirable decision tree is one having a relatively small number of branches, a relatively small number of intermediate nodes from which these branches diverge, terminal nodes with a non-zero number of entries, and high prediction power (correct classifications at the terminal nodes). In some embodiments, CART may be used in conjunction with a gradient boosting algorithm, where each boosted tree is combined with its mates using a weighted voting scheme. Gradient boosting may be used to force the binary decision tree to classify data that was previously misclassified.

As noted above, a wide variety of statistical analysis techniques may be used to determine the one or more statistical relationships. These may include one or more supervised learning techniques, one or more unsupervised learning techniques, one or more parametric analysis techniques (such as a Pearson's product-moment correlation coefficient r or an inner product), and/or one or more non-parametric analysis techniques. Non-parametric analysis techniques may include a Wilcoxon matched pairs signed-rank test (for ordinal or ranked data), a Kolmagorov-Smirnov one-sample test (for ordinal or ranked data), a dependent t-test (for interval or ratio data), a Pearson chi-square, a chi-square test with a continuity correction (such as Yate's chi-square), a Mantel Heanszel chi-square test, a linear-by-linear association test, a maximum likelihood test, a risk ratio, an odds ratio, a log odds ratio, a Yule Q, a Yule Y, a phi-square, a Kappa measure of agreement, a McNemar change test, a Mann Whitney U-test, a Spearman's rank order correlation coefficient, a Kendall's rank correlation, a Krushcal-Wallis One-Way Analysis of Variance, and a Turkey's quick test.

Supervised learning techniques may include least-squares regression (including correlation), ridge regression, partial least-squares (also referred to as partial correlation), a perceptron algorithm, a winnow algorithm, linear discriminant analysis (LDA), Fisher discriminant analysis (FDA), logistic regression (LR), a Parzen windows classifier, a (k−) nearest-neighbor classification, multivariate adaptive regression splines (MARS), multiple additive regression trees (MART), SVM, LASSO (a regularized linear regression technique like ridge regression, but with $L_1$-norm regularization of the coefficients), least angle regression (LARS), decision trees (such as CART, with and without gradient boosting, such as ID3 and C4.5), bagging, boosting (such as, adaboost) of simple classifiers, kernel density classification, a minimax probability machine (MPM), multi-class classification, multi-label classification, a Gaussian Process classification and regression, Bayesian statistical analysis, a Naive Bayes classifier, and neural networks for regression and classification. While some of these supervised learning algorithms are linear, it should be understood that one or more additional non-linear versions may be derived using the same "kernel-methodology", as previously described for the SVM, leading to a spectrum of kernel-based learning methods, for example, kernel FDA, kernelized logistic regression, the kernelized perceptron algorithm, etc. One or more of these non-linear versions may be used to perform the statistical analysis.

Unsupervised learning techniques may include a kernel density estimation (using, for example, Parzen windows or k-nearest neighbors), more general density estimation techniques, quantile estimation, clustering, spectral clustering, k-means clustering, Gaussian mixture models, an algorithm using hierarchical clustering, dimensionality reduction, such as principal component analysis or PCA, multi-dimensional scaling (MDS), isomap, local linear embedding (LLE), self-organizing maps (SOM), novelty detection (also referred to as single-class classification, such as single-class SVM or single-class MPM), canonical correlation analysis (CCA), independent component analysis (ICA), factor analysis, and/or non-parametric Bayesian techniques like Dirichlet processes. As noted above for the supervised learning techniques, one or more additional non-linear versions of one or more linear unsupervised learning techniques may be used to perform the statistical analysis, such as kernel PCA, kernel CCA and/or kernel ICA.

In some embodiments, at least a portion of the statistical analysis, such as determination of one or more statistical relationships and/or identification of one or more association variables may include spectral analysis. For example, a Fourier transform or a discrete Fourier transform may be performed on the temporal onsets, one or more patterns of occurrence of one or more variables, and/or one or more patterns of occurrence of one or more compound variables. Analysis in the frequency domain may allow patterns in at least some of the data, such an impact of a woman's menstrual cycle, to be determined.

In some embodiments, determination of one or more statistical relationships and/or identification of one or more association variables may include the use of design of experiments.

In some embodiments, at least a portion of the statistical analysis and/or identification of one or more association variables may be implemented using one or more filters, including analog filters, digital filters, adaptive filters (using, for example, a least square error or gradient approach, such as steepest decent), and/or neural networks. The one or more filters may be implemented using one or more DSPs. In some embodiments, the statistical analysis and/or identification of one or more association variables may be implemented in hardware, for example, using one or more ASICs, and/or software.

Figure 14:
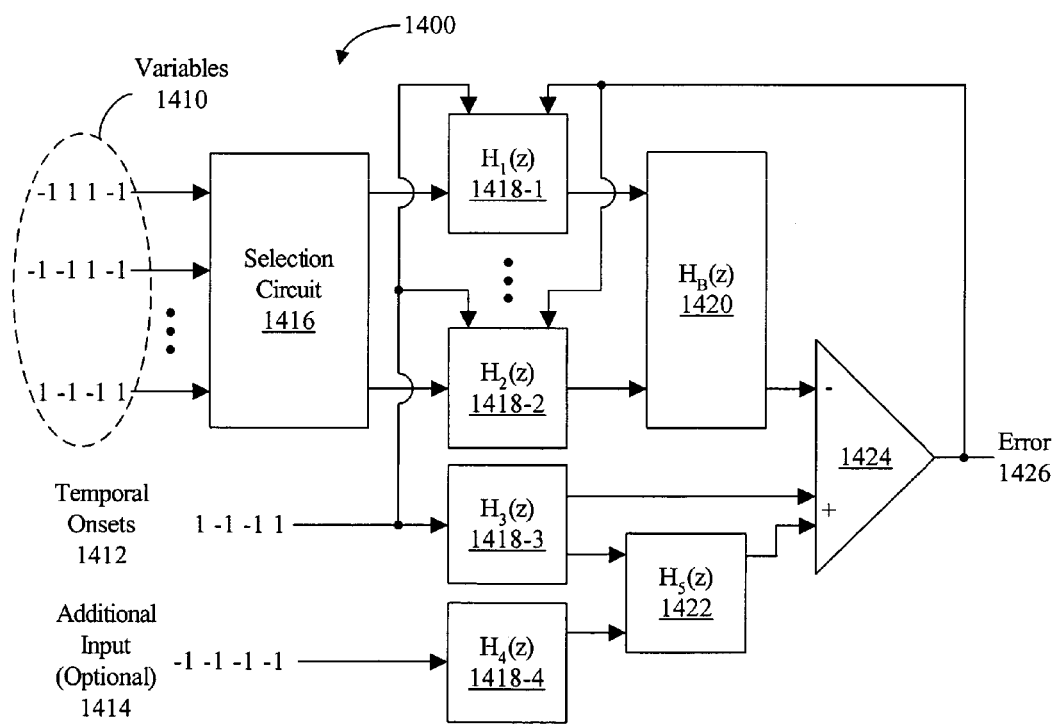
FIG. 14 is a block diagram illustrating an embodiment of a signal processing circuit.

FIG. 14 is a block diagram illustrating an embodiment of a signal processing circuit 1400 for determining one or more statistical relationships and/or identifying one or more association variables. Presence (coded with 1s) and absence information (coded with −1s) for one or more variables 1410 are selectively coupled using selection circuit 1416 to one or more filters $H_i$ 1418. The selection circuit 1416 may be a multiplexer. The filters $H_i$ 1418 may perform spectral modification, such as limiting one or more of the variables 1410 to one or more time intervals, or one or more sequences of time intervals. The filters $H_i$ 1418 may convert the presence and absence information for one or more of the variables 1410 into one or more patterns of occurrence.

The filters $H_i$ 1418 may be adaptive. The adaptation may be in accordance with temporal onsets 1412 and/or an error 1426. The adaptation may include one or more time intervals, such as the first time intervals 912 (FIG. 9A), and/or one or more offsets, such as the offset 924 (FIG. 9A). In some embodiments, the adaptation may minimize or reduce the error 1426 or a portion of the error 1426. In the embodiments for migraine, for example, the adaptation may reduce a predicted number of migraines, a predicted severity and/or a predicted frequency.

Outputs from one or more of the filters $H_i$ 1418 may be coupled to filter $H_B$ 1420. The filter $H_B$ 1420 may perform additional spectral modification. As a consequence, an arbitrary filtering operation may be implemented using one or more of the filters $H_i$ 1418 and/or the filter $H_B$ 1420. The filter $H_B$ 1420 may determine a pattern of occurrence for one or more variables 1410 and/or one or more compound variables.

The temporal onsets 1412 may be filtered using filter $H_3$ 1418-3. Comparisons between an output of filter $H_3$ 1418-3 and an output of the filter $H_B$ 1420 may be performed using statistical analysis element 1424. In some embodiments, the statistical analysis element 1424 may be a comparator. Statistical analysis element may implement one or more statistical analysis techniques, such as the log likelihood ratio. The statistical analysis element 1424 may generate the error 1426. The error 1426 may be a scalar, a vector, or a matrix. In some embodiments, the statistical analysis element 1424 may perform a relative time shifting of the output of filter $H_3$ 1418-3 and the output of the filter $H_B$ 1420. In an exemplary embodiment, the statistical analysis element 1424 may determine one or more statistical relationships between the temporal onsets 1412 and one or more patterns of occurrence of one or more variables and/or one or more compound variables. The one or more statistical relationships may be determined sequentially and/or substantially concurrently. The error 1426 may correspond to the one or more statistical relationships.

In some embodiments, one or more optional additional inputs, such as optional additional input 1414, may be filtered using one or more filters, such as filter $H_4$ 1418-4, and/or combined with the temporal onsets 1412 using a filter, such as filter/combiner $H_5$ 1422. An output from the filter/combiner $H_5$ 1422 may be included in the analysis performed by the statistical analysis element 1424. The one or more optional additional inputs may allow inclusion of cross-terms. In some embodiments, the one or more optional additional inputs may include other disease symptoms and/or disease conditions.

While a single output is shown for the filter $H_B$ 1420, there may be additional outputs that are used by the statistical analysis element 1424. Similarly, there may be additional outputs from the filter/combiner $H_5$ 1422 that are used by the statistical analysis element 1424. While embodiment 1400 uses presence and absence information in the one or more variables 1410, the temporal onsets 1412, and the optional additional input 1414, in some embodiments one or more of these items may only use presence information. Embodiment 1400 may include fewer elements or additional elements. A position of at least two elements may be switched. Functions of two or more elements may be combined into a single element.

Figure 15:
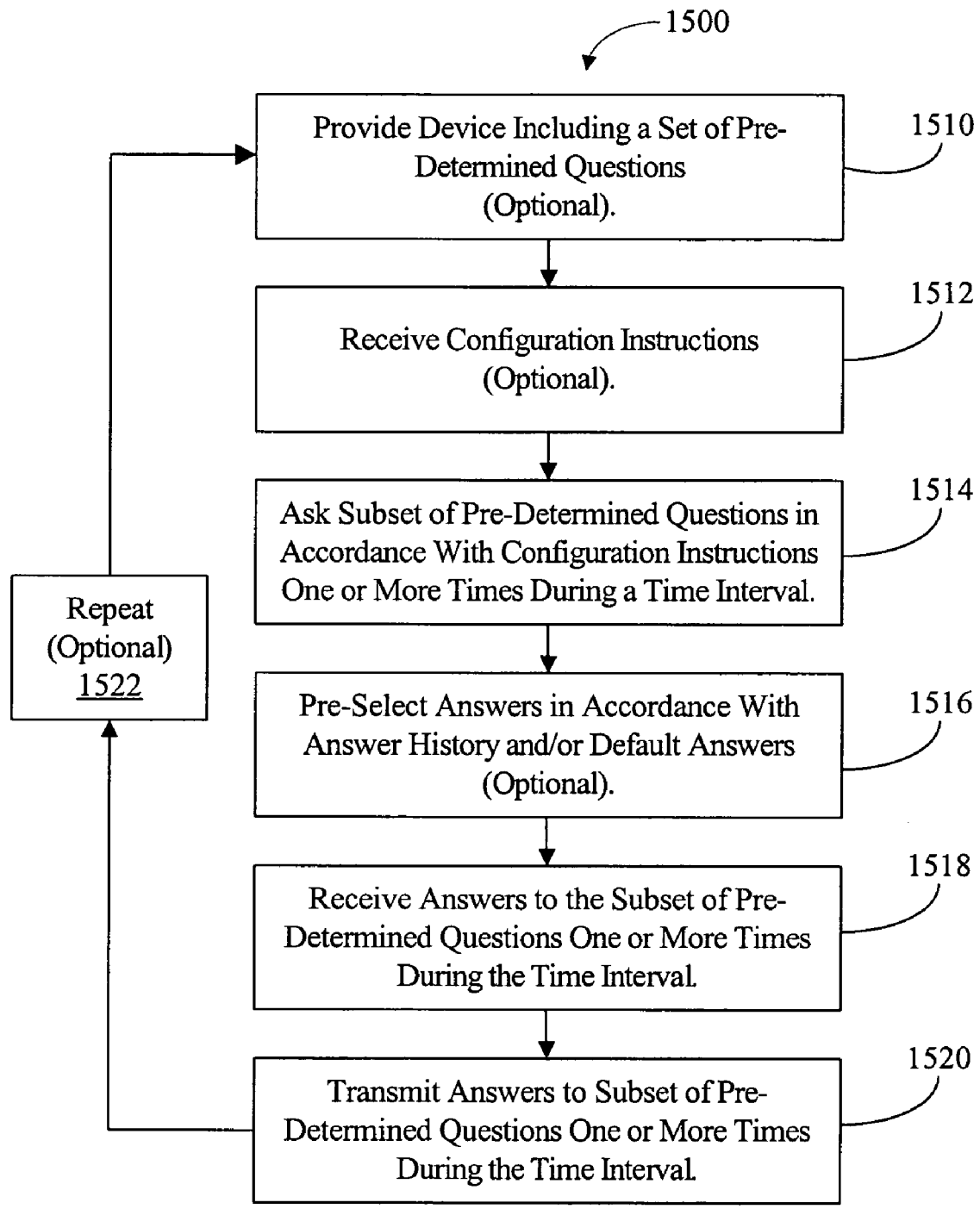
FIG. 15 is a flow diagram illustrating an embodiment of a process for collecting information.

Attention is now directed to embodiments of processes for implementing the collection of information during the data-collection time interval, the determining of one or more statistical relationships, the identification of one or more association variables, and/or the providing of recommendations to at least the first individual and/or at least the second individual. FIG. 15 is a flow diagram illustrating an embodiment 1500 of a process for collecting information. A device including a set of pre-determined questions may be optionally provided (1510). Configuration instructions may be optionally received (1512). A subset of pre-determined questions may be asked, one or more times during a time interval, in accordance with the configuration instructions (1514). Answers may be optionally pre-selected in accordance with an answer history and/or default answers (1516). Answers to the subset of pre-determined questions may be received one or more times during the time interval (1518). Answers to the subset of pre-determined questions may be transmitted one or more times during the time interval (1520). Operations in embodiment 1500 may be optionally repeated, one or more times (1522). The process in embodiment 1500 may include fewer operations or additional operations. A position of at least two operations may be switched. Two or more operations may be combined into a single operation.

Figure 16:
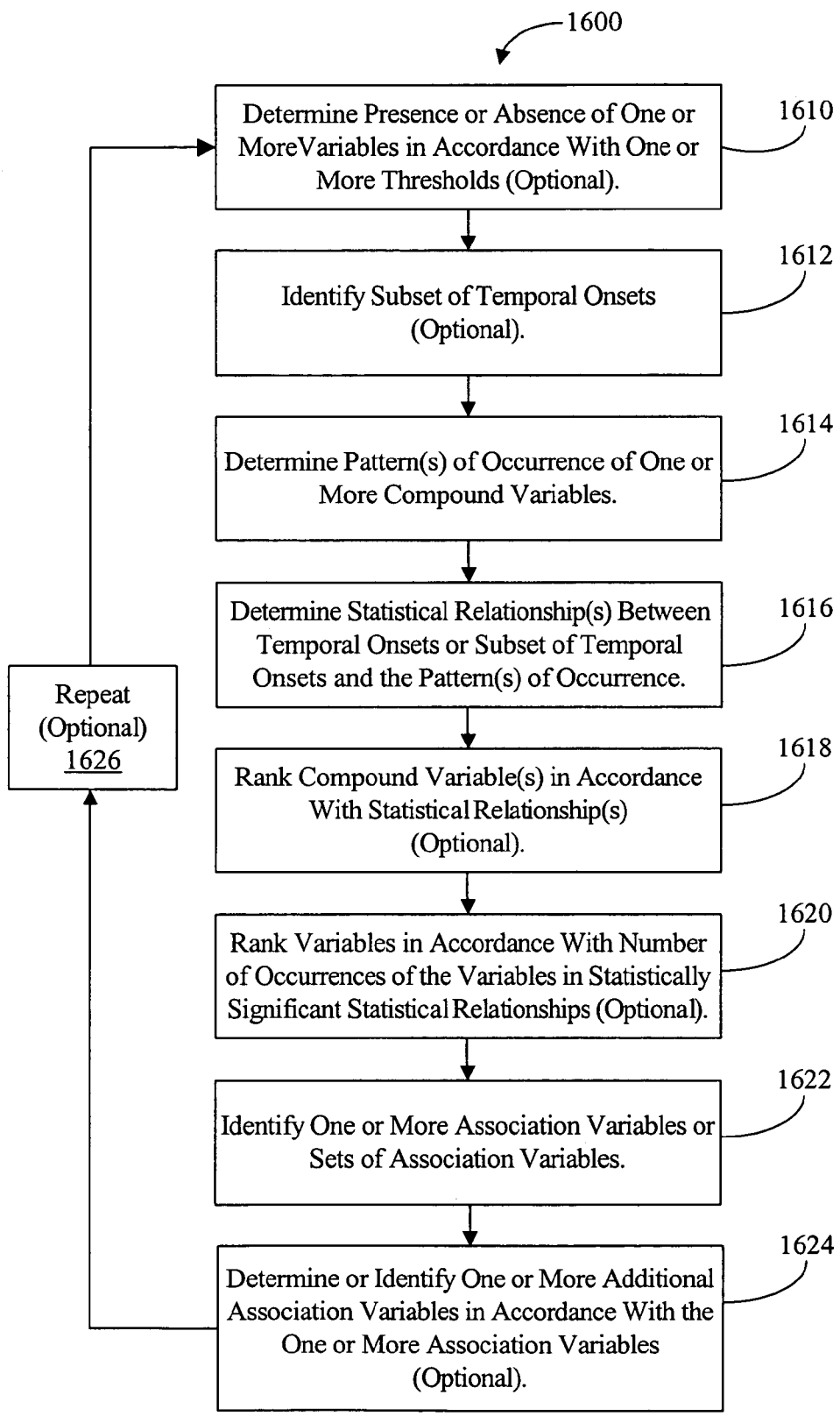
FIG. 16 is a flow diagram illustrating an embodiment of a process for determining one or more association variables.

FIG. 16 is a flow diagram illustrating an embodiment 1600 of a process for determining one or more association variables. Presence or absence of one or more variables may be optionally determined in accordance with one or more thresholds (1610). A subset of temporal onsets may be optionally identified (1612). Pattern(s) of occurrence of one or more compound variables may be determined (1614). Statistical relationship(s) between temporal onsets or the subset of temporal onsets and the pattern(s) of occurrence may be determined (1616). The compound variable(s) may be optionally ranked in accordance with the statistical relationship(s) (1618). The variables may be optionally ranked in accordance with a number of occurrences of the variables in statistically significant statistical relationships (1620). One or more association variables or sets of association variables may be identified (1622). One or more additional association variables may be optionally determined or identified in accordance with the one or more association variables (1624). Operations in embodiment 1600 may be optionally repeated one or more times (1626). The process in embodiment 1600 may include fewer operations or additional operations. A position of at least two operations may be switched. Two or more operations may be combined into a single operation.

Figure 17:
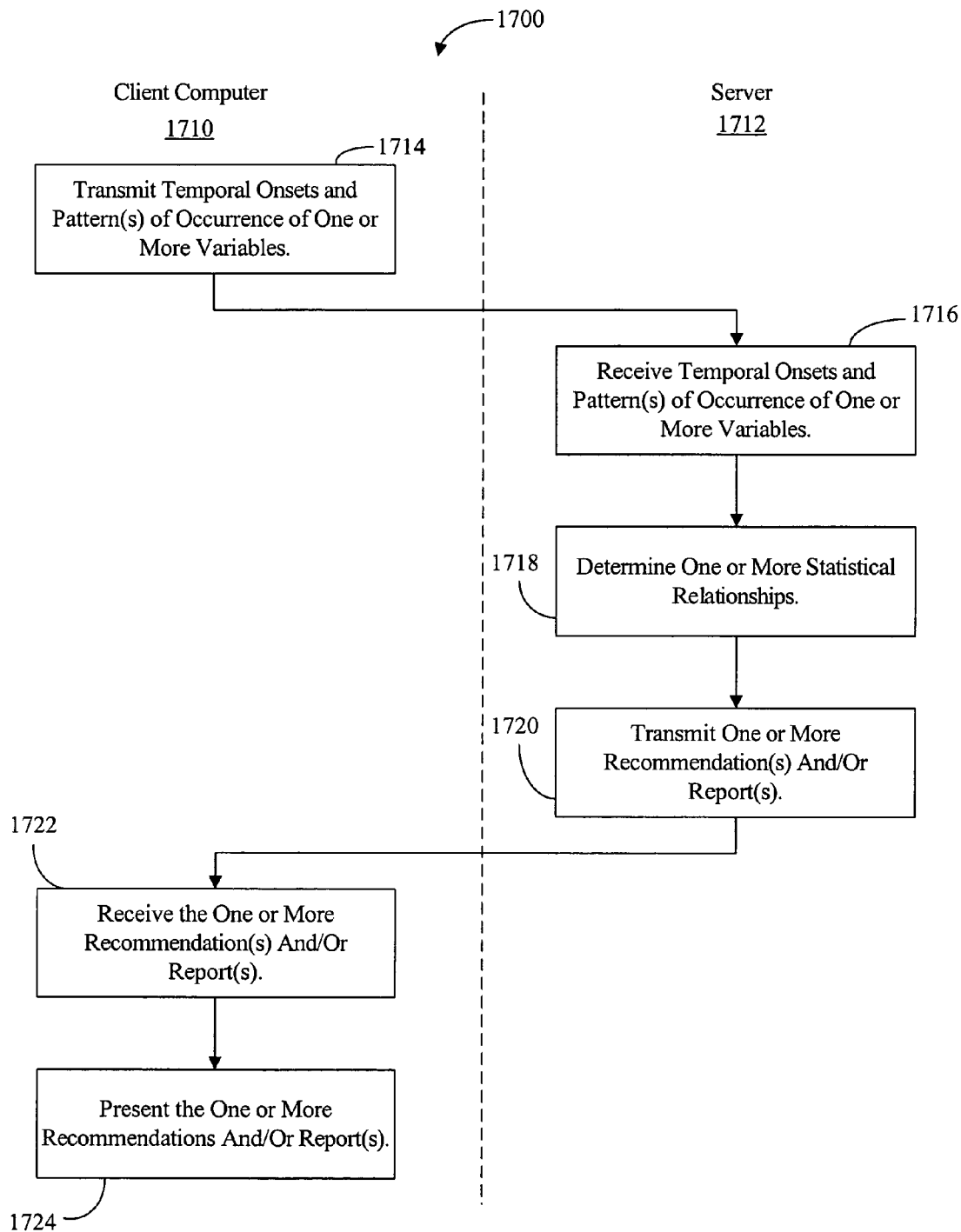
FIG. 17 is a flow diagram illustrating an embodiment of a process for providing recommendation(s) and/or report(s).

FIG. 17 is a flow diagram illustrating an embodiment 1700 of a process for providing recommendation(s) and/or report(s). Temporal onsets and pattern(s) of occurrence of one or more variables may be transmitted (1714) from a client computer 1710 to a server computer 1712. The temporal onsets and the pattern(s) of occurrence of one or more variables may be received (1716). One or more statistical relationships may be determined (1718). One or more recommendation(s) and/or report(s) may be transmitted (1720) from the server 1712 to the client computer 1710. The one or more recommendation(s) and/or report(s) may be received (1722). The one or more recommendations and/or report(s) may be presented (1724). The process in embodiment 1700 may include fewer operations or additional operations. A position of at least two operations may be switched. Two or more operations may be combined into a single operation.

Figure 18:
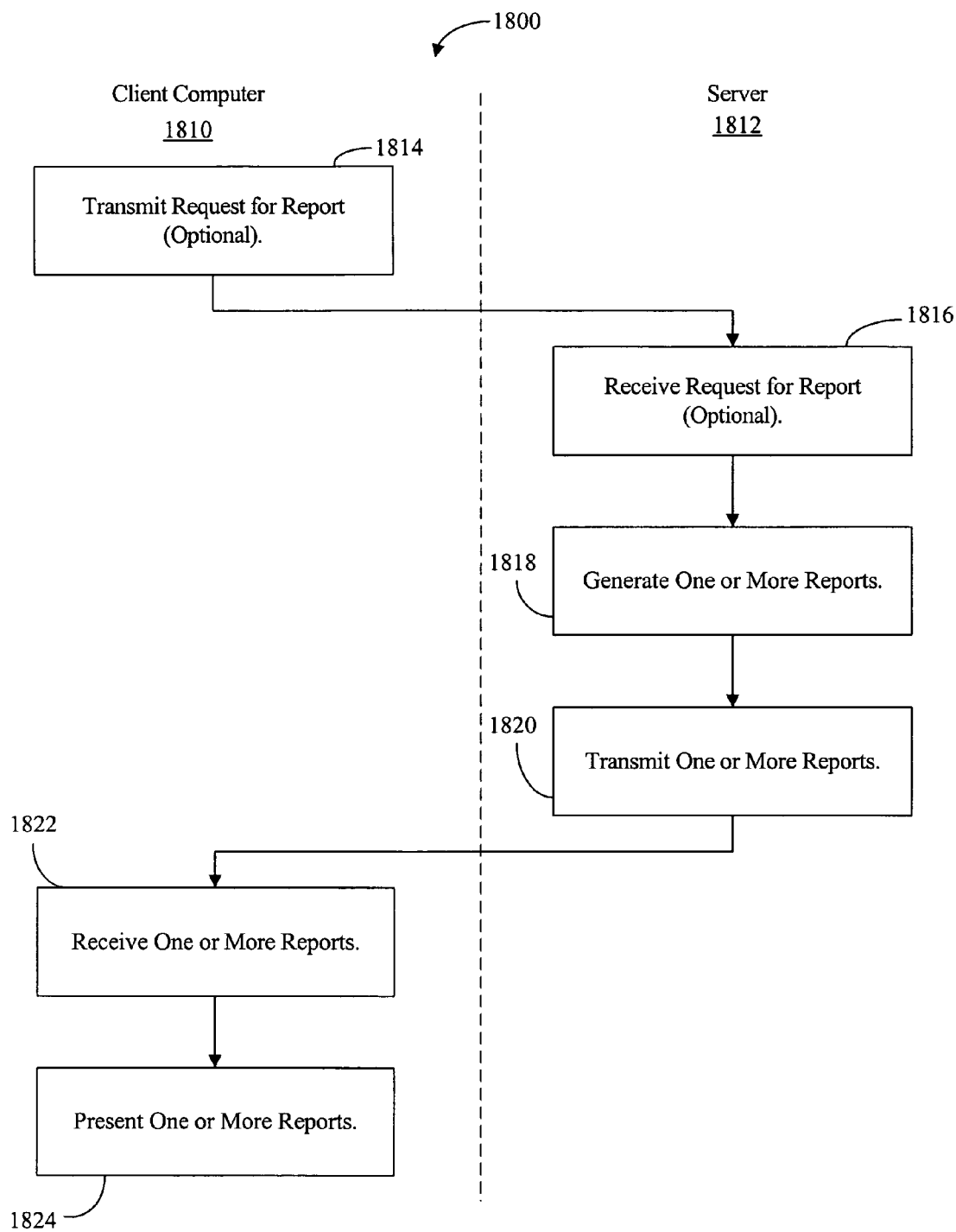
FIG. 18 is a flow diagram illustrating an embodiment of a process for providing one or more reports.

FIG. 18 is a flow diagram illustrating an embodiment 1800 of a process for providing one or more reports. A request for a report may be optionally transmitted (1814) from a client computer 1810 to a server computer 1812. The request for the report may be optionally received (1816). One or more reports may be generated (1818). The one or more reports may be transmitted (1820) from the server 1812 to the client computer 1810. The one or more reports may be received (1822). The one or more reports may be presented (1824). The process in embodiment 1800 may include fewer operations or additional operations. A position of at least two operations may be switched. Two or more operations may be combined into a single operation.

Figure 19:
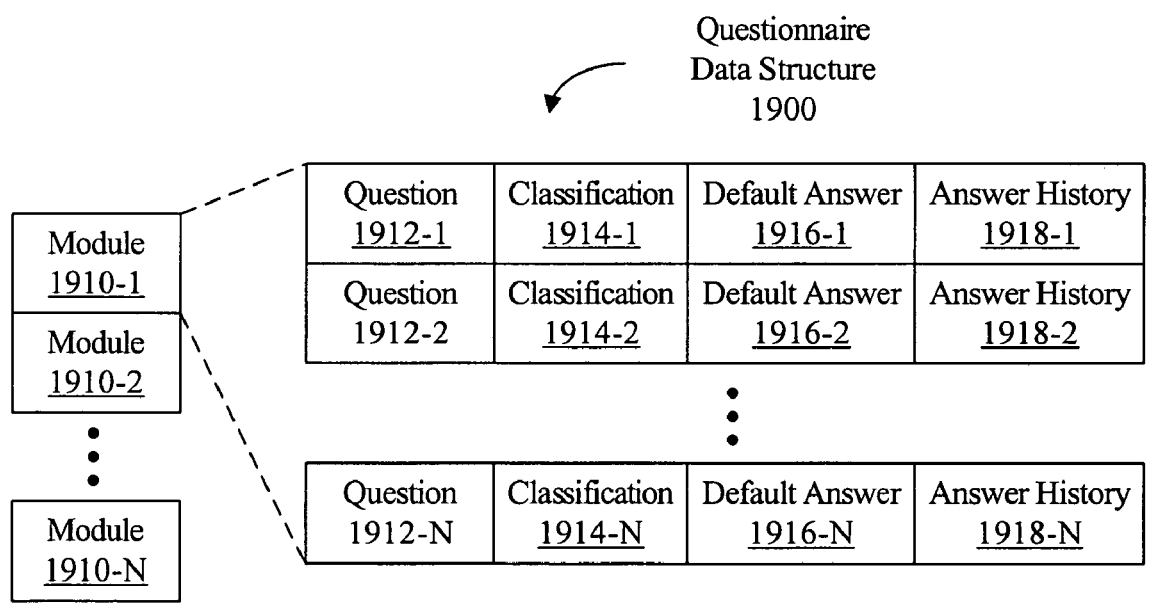
FIG. 19 is a block diagram illustrating an embodiment of a questionnaire data structure.

Attention is now directed to embodiments of data structures that may be used in implementing the collection of information during the data-collection time interval, the determining of one or more statistical relationships, the identification of one or more association variables, and/or the providing of one or more recommendations and/or one or more reports to at least the first individual and/or at least the second individual. FIG. 19 is a block diagram illustrating an embodiment of a questionnaire data structure 1900. The questionnaire data structure 1900 may include one or more modules 1910. A respective module, such as module 1910-1, may include entries for one or more questions 1912, one or more classifications 1914 for the questions 1912 (such as primary or secondary, or general or specific), one or more default answers 1916, and/or one or more answer histories 1918. The questionnaire data structure 1900 may include fewer or addition modules and/or entries. A position of two modules and/or a position of two entries may be switched. Two or more modules may be combined into a single module. Two or more entries may be combined into a single entry.

Figure 20:
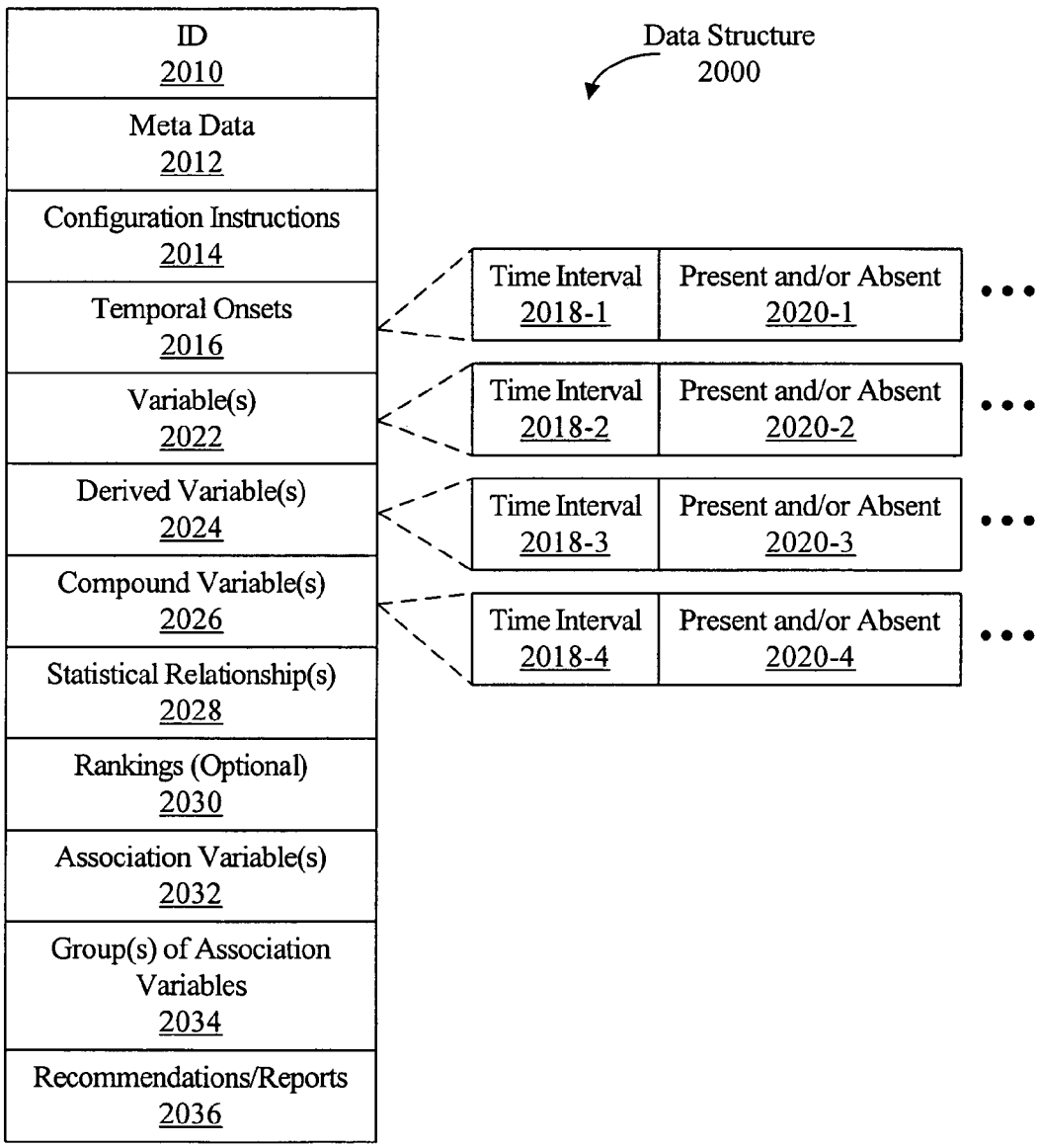
FIG. 20 is a block diagram illustrating an embodiment of a data structure.

FIG. 20 is a block diagram illustrating an embodiment of a data structure 2000. The data structure 2000 may include one or more sets of categories. A respective set of categories may correspond to at least the first individual. The respective set of categories may include identification 2010 for at least the first individual, meta data 2012 (such as relevant demographic, billing and/or medical history data for at least the first individual), configuration instructions 2014, temporal onsets 2016, variable(s) 2022, derived variable(s) 2024, compound variable(s) 2026, statistical relationships 2028, optional rankings 2030, association variable(s) 2032, group(s) of association variables 2034 and/or recommendations/reports 2036. The temporal onsets 2016, the variable(s) 2022, the derived variable(s) 2024, and/or the compound variable(s) 2026 may include one or more entries including time intervals 2018 and corresponding presence and/or absence information 2020. The data structure 2000 may include fewer or addition categories and/or entries. Two or more categories may be combined into a single category. A position of two categories and/or a position of two entries may be switched. Two or more entries may be combined into a single entry.

Attention is now directed towards alternative applications for the processes and apparatuses for collection of information, determining one or more statistical relationships, identifying one or more association variables, and providing one or more recommendations and/or one or more reports. In some embodiments, one or more fees may be charged for offering the service of collecting the information and/or identifying one or more association variables (such as one or more migraine triggers) for at least the first individual. In some embodiments, the one or more fees may be in accordance with a cost savings associated with a reduced usage of one or more pharmacological agents (such as one or more acute and/or preventive therapies). The one or more fees may be collected from at least the first individual, at least the second individual, and/or one or more insurance providers. In some embodiments, information associated with the one or more identified association variables may be sold to third parties. In some embodiments, advertising may be presented to at least the first individual and/or at least the second individual during the collection of information, the providing of one or more recommendations and/or the providing of one or more reports. Fees may be charged to advertisers for such services.

In some embodiments, at least the first individual may be associated with one or more groups, such as one or more groups of migraine patients, in accordance with one or more identified association variables (such as migraine triggers). A respective group may be analyzed to determine one or more existing or new acute and/or preventive therapies that may provide improved efficacy for the respective group. Using migraine as an exemplary embodiment, improved efficacy may include a reduction in migraine frequency, a reduction in migraine severity, a reduction in recurrence, a reduction in one or more adverse reactions or side effects, a reduction in the use of one or more pharmacological agents, and/or an improved efficacy in aborting one or more migraine attacks relative to other acute and/or preventive therapies.

In some embodiments, association with one or more groups and/or analysis of the respective group may include statistical analysis and/or determining a presence or an absence of one or more biological markers, including genetic material, deoxyribonucleic acid, ribonucleic acid, one or more genes, one or more proteins, and/or one or more enzymes that may be common to the respective group and/or two or more groups. The one or more biological markers may be determined by testing one or more biological samples, including a blood sample, a urine sample, a stool sample, a saliva sample, a sweat sample, a mucus sample, a skin scrapping, and/or a tear. The one or more biological samples may be analyzed using chemical analysis, genetic analysis (such as genetic sequencing), nuclear quadrapole resonance, nuclear magnetic resonance, and/or electron spin resonance. In some embodiments, one or more patients that have been diagnosed with a respective disease, such as migraine, may be tested for the one or more biological markers to associate the one or more patients with one or more of the groups of patients, and to recommend one or more pharmacological agents (such as one or more acute pharmacological agents, for example, a respective family of triptans, and/or one or more preventive therapies) that may offer improved efficacy relative to other pharmacological agents for the one or more patients. Such a test or tests, based on the one or more biological markers, may reduce or eliminate the current approach of trial and error in searching for one or more pharmacological agents for patients, such as one or more effective acute and/or preventive therapies, which results in delays in patient treatment and additional expense.

In some embodiments, the information collected during the data-collection time interval may be analyzed to determine one or more subgroups within a population of patients, such as the group of migraine patients mentioned above. The one or more subgroups may be determined based on the one or more identified association variables (such as migraine triggers), an efficacy of one or more pharmacological agents (such as one or more acute and/or preventive therapies), side effects or adverse reactions to one or more pharmacological agents, and/or patient symptoms (such as migraine severity and/or frequency). The subgroups may be determined using statistical analysis and/or determining a presence or an absence of the one or more biological markers. In some embodiments, the one or more subgroups may be used to study drug interactions in a real-world setting and patient population. In some embodiments, the one or more subgroups may be indicative of underlying polymorphism in a genetic basis for a respective disease. Information corresponding to the one or more subgroups may be sold to a third party, for example, for use in molecular biology studies of the respective disease, the development of one or more pharmacological agents, and/or a management of costs associated with the disease.

In an exemplary embodiment, a genetic polymorphism for migraine may be determined. Migraine is a genetically heterogeneous (polygenetic) disorder. While there is a strong familial aggregation of migraine (it runs in families) and there is increased concordance for the disease in mono-zygote twins over di-zygote twins, suggesting that it has a significant genetic component, in part it may be explained by environmental determinants. Thus, heritability estimates are calculated to be between 40 and 60%. The complex genetics of migraine (heterogeneity) may have hampered gene identification. Grouping migraine patients into one or more subgroups based on identified migraine triggers may aid in the identification of one or more genetic bases of and/or in the determination of genetic information for this disease.

Additional applications in determining one or more asthma triggers and/or one or more probable asthma triggers for one or more patients with asthma, determining one or more drug interactions in one or more patients with hypertension, and pattern mapping for one or more patients with diabetes mellitus are described below. The apparatuses and processes disclosed may also be used to determine an efficacy of one or more homeopathic remedies, such as an efficacy of one or more herbs.

Asthma is a chronic inflammatory condition characterized by excessive sensitivity of the lungs to various stimuli. As with migraine patients, many asthma patients are instructed to keep written patient diaries and to attempt to identify patient-specific trigger mechanisms. Asthma triggers may be specific to an individual, such as at least the first individual, or may correspond to one or more groups of individuals. Asthma triggers may be cumulative and/or inter-operative. One or more asthma triggers may be required to trigger an attack in a respective patient.

In some embodiments, entry criteria may include that asthma in the respective patient may be sufficiently well controlled that asthma attacks are not occurring too often of too infrequently to preclude determination of triggers. In some embodiments, the subset of pre-determined questions may be used to collect information for one or more variables that correspond to one or more potential asthma triggers. Asthma triggers may include respiratory infections (such as viral infections or colds), allergies (including pollen, mold, animal dander, feather, dust, food, and/or cockroaches), irritating gases (such as cigarette smoke), particles in the air (indoor and/or outdoor air pollutants, including ozone), activities (such as exercise and vigorous exercise), behaviors (such as excitement or stress), and/or environmental conditions (such as exposure to cold air or a sudden temperature change). For asthma, the temporal onsets 910 (FIG. 9A) may correspond to onset times and/or an onset time intervals for one or more asthma attacks, which are the events. Statistical analysis may determine one or more statistical relationships between the temporal onsets and patterns of occurrence of one or more variables and/or one or more compound variables allowing one or more association variables (asthma triggers) to be identified. The one or more association variables may be provided to at least the first individual and/or at least the second individual in the form of one or more recommendations and/or one or more reports. The one or more recommendations may include one or more asthma triggers that at least the first individual may wish to avoid.

In some embodiments, the information collected during the data-collection time interval may include one or more metrics corresponding to measures of asthma control in at least the first individual. The one or more metrics may include day and/or night symptoms (such as wheeze and cough), interventions such as a quantified use of inhaled bronchodilators (such as a number of treatments with pharmacological agents such as albuterol) and/or oral corticosteroid (including a dosage), daytime activity levels, peak expiratory flow in 1 second, and/or forced expiratory volume in 1 second. Day symptoms may include if vigorous activity is okay, if the respective patient can only run briefly, if the respective patient can only walk, and/or if the respective patient must rest at home. Night symptoms may include whether it was a good night (such as the respective patient slept well but there was some wheeze or cough, or the respective patient was awake briefly with wheeze or cough) or a bad night (the respective patient was awake repeatedly). Wheeze may be described as none, briefly, not troublesome, several times, or continuous. Cough may be described as none, persistent but not troublesome, interrupted activities once, or interrupted activities more than once. Peak flow and/or volume may be measured in the morning (best of three efforts) and/or the evening (best of 3 efforts).

Hypertension (high blood pressure) is a multi-factorial disease. As a consequence, many patients that are treated for hypertension may be prescribed two or more pharmacological agents in an attempt to control or regulate the disease. Some patients may use dozens of drugs concurrently. Such pharmacological agents, however, many have side effects and there may be interactions between drugs. It may be difficult for at least the second individual to determine which pharmacological agent(s) may be associated with which side effect, and to modify drug choice and dosage accordingly.

In some embodiments, the subset of pre-determined questions may be used to collect information corresponding to variables such as what pharmacological agents were taken and when, what the dosages were (time and quantity), side effect symptoms, and/or blood pressure data. Some information, such as test results corresponding to side effects of one or more pharmacological agents, may be provided by and/or collected from at least the second individual. The events and temporal onsets (including onset times and/or onset time intervals) may include improved regulation of hypertension, poorer regulation of hypertension, a reduction in one or more side effects, and/or an increase in a severity of one or more side effects. Statistical analysis, including one or more look-up tables of possible side effects of (discussed further below) and/or metabolic pathways for one or more pharmacological agents, may be used to determine the one or more statistical relationships and identify the one or more association variables. One or more side effects may be used as one or more additional inputs 1414 (FIG. 14). One or more recommendations and/or reports may be provided to at least the first individual and/or at least the second individual. These may include suggestions on one or more association variables that may be avoided and/or modified (such as for behaviors) to improve control of hypertension. The one or more recommendations and/or reports may include suggestions for pharmacological agents and/or dosage (time and/or quantity) to reduce or eliminate one or more side effects and/or to improve regulation of hypertension.

Pharmacological agents may include diuretics, beta blockers, ACE inhibitors, angiotensin II receptor blockers, calcium channel blockers, alpha blockers, central agonists, peripheral adrenergic inhibitors, and/or blood vessel dilators. Diuretics may decrease potassium levels. As a consequence, "potassium sparing" pharmacological agents such as amiloride, spironolactone or triamterene may be taken concurrently. Side effects may include weakness, leg cramps, being tired, gout and/or impotence. In diabetics, diuretics may change the blood glucose level. This may be addressed by changing the diuretic, diet, activity insulin type, insulin dosage, and/or the use of additional pharmacological agents to change insulin sensitivity. Side effects of beta blockers may include insomnia, cold hands and feet, tiredness, depression, a slow heartbeat, symptoms of asthma, and/or impotence. Beta blockers may also complicate the treatment of diabetes mellitus. Side effects of ACE inhibitors may include a skin rash, loss of taste, a chronic dry hacking cough, and/or kidney damage. Side effects of angiotensin II receptor blockers may include dizziness. Side effects of calcium channel blockers may include heart palpitations, swollen ankles, constipation, headache, and/or dizziness. Side effects of alpha blockers may include a fast heart rate, dizziness, and/or a drop in blood pressure when the respective patient stands up. A combination of alpha and beta blockers may result in a drop in blood pressure when the respective patient stands up. Side effects of central agonists may include a drop in blood pressure (including a feeling of weakness and/or fainting) when the respective patient is in an upright position (standing or walking), drowsiness, sluggishness, dryness of the mouth, constipation, fever, anemia, and/or impotence. Side effects of peripheral adrenergic inhibitors may include a stuffy nose, diarrhea, heartburn, nightmares, insomnia, depression, diarrhea, impotence, and/or a drop in blood pressure when the respective patient stands. Side effects of blood vessel dilators may include headaches, swelling around the eyes, heart palpitations, aches or pains in the joints, fluid retention (with a marked weight gain), and/or excessive hair growth.

Diabetes mellitus (including insulin dependence) is a complex disease that is often difficult to manage. Diabetes mellitus may be classified as one of two types. Type I is thought to be an auto-immune disorder where the pancreas is no longer able to produce sufficient insulin. In type II, cellular membranes may become less sensitive to the effects of insulin. In addition, over time the resulting elevated blood glucose levels may cause the pancreas to produce insufficient insulin. Blood glucose level is dependent on a large number of time varying, interdependent parameters in several sub-systems in the body. In addition, there can be secondary effects on the vascular and neurological systems. Many diabetic patients are instructed to keep written patient diary and to attempt to identify reasons why the blood glucose level is high or low (which is referred to as pattern matching).

In some embodiments, entry criteria for the respective patient, such as at least the first individual, may include classification of the disease as early stage, middle stage, or late stage depending on a severity of secondary effects of this disease, such as vascular and neurological damage. A level of control of the disease in the respective patient may be determined to confirm that conditions such as diabetic coma and insulin shock are either not present or are unlikely to occur. This may allow reliable information to be collected during the data-collection time interval. In some embodiments, the initial survey may include information from at least the first individual and/or at least the second individual corresponding to a performance of the liver and/or the kidneys. The performance of the liver and/or the kidneys may be in accordance with the classification as early stage, middle stage, or late stage. In some embodiments, the initial survey may include a fat percentage, for example, in accordance with a body mass index. In some embodiments, the initial survey may include measurements of one or more blood glucose step responses for one or more types of carbohydrates, fats, protein, and/or minerals.

The subset of pre-determined questions may be used to collect information corresponding to variables such as diet, activity, use of one or more pharmacological agents (which may include one or more diabetes medicines and/or one or more insulin types, such as fast acting or slow acting, one or more injection sites, usage times, and/or quantities), a presence of infection (such as a measure of body temperature), hydration or dehydration, hormonal changes (such as those associated with pregnancy, puberty, menstruation, and/or menopause), dawn phenomenon, behaviors (such as stress and/or emotion), and/or one or more daily blood glucose measurements (for example, before meals, 2 hours after meals, and/or before bedtime). Diet may include a food consumption history, including timing of meals, types of foods, brands, quantities, carbohydrates consumed (which may include amounts and types), fats consumed (which may include amounts and types), proteins consumed (which may include amounts and types), minerals consumed (which may include amounts and types), how full the respective patient was when he or she ate, and/or if a respective meal was home made. Activity may include an activity level (such as exercise) and/or an activity history (which may extend over several days).

In some embodiments, the events and temporal onsets (including onset times and/or onset time intervals) correspond to deviations of blood glucose for at least the first individual outside of a regulation band, for example, between 80–120 mg/dl or 80–200 mg/dl. Statistical analysis of one or more temporal onsets and patterns of occurrence of one or more variables and/or one or more compound variables may be in accordance with a metabolic model. The metabolic model may include one or more feedback loops, variable sensitivities, and/or impulse (linear) responses for one or more types of carbohydrates, fats, proteins, and/or minerals. The metabolic model may include a model for glucagon, insulin absorption, digestion (which may include an absorption rate for different types of carbohydrates, fats, proteins, and/or minerals), storage in the liver (an insulin sensitivity of liver), and/or a renal threshold for glucose. The metabolic model may also include one or more non-linear responses, such as for (peripheral) insulin sensitivity, glucose level (which is typically linear within bounds, such as above 70 mg/dl and below 300 mg/dl) and behavior/activity (such as activity history). The metabolic model may allow extraneous variables to be excluded in comparisons of different temporal onsets.

One or more statistical relationships may allow one or more association variables, such as one or more variables and/or one or more compound variables that may be associated with a deviation in blood glucose level, to be identified. One or more recommendations and/or one or more reports may be provided to at least the first individual and/or at least the second individual in accordance with the one or more identified association variables. These may include recommendations regarding one or more association variables that may be avoided and/or modified (such as for behaviors) to improve control of blood glucose. This may include specific circumstances (patterns of activity and/or diet) where the recommendations are applicable. The one or more recommendations and/or reports may include pharmacological agents and/or dosage (time and/or quantity) to improve control of blood glucose. Adjustments to insulin, for example, may include a mean daily dosage and/or day-to-day variations in dosage about the mean, such as a change in one or more quantities of insulin and/or one or more fewer or additional injections. Patterns of activity may include a sequence of activities over a day, several days, and/or a week. For example, the sequence of activities may include an exercise history.

The system and analysis techniques described may also be used for web-related applications, e.g., to determine the relevant variables and/or compound variables that internet advertisement may exhibit in order for users to click on them or pursue them as a function of time. The advertisement variables may include word content, graphical properties, colors, animation and/or appearance. In another embodiment, the system and analysis techniques describe may be used in network-related applications to determine the variables and/or compound variables that may lead to the network going down or experience a fatal crash as a function of time. The variables may include an amount and a content of network traffic (registered at nodes, routers, servers, connections, etc.), caching, package requests posted by users, package requests received by servers, routing decisions, a number or percentage of packages that arrive corrupted and/or network delays.

While embodiments of apparatuses and related methods for determining one or more association variables have been described, the apparatuses and related methods may be applied generally to determine statistical relationships between one or more temporal onsets corresponding to one or more events and patterns of occurrence of one or more variables and/or one or more compound variables in a wide variety of statistical learning problems, in medicine, psychology, statistics, engineering, applied mathematics and operations research.

The foregoing description, for purposes of explanation, used specific nomenclature to provide a thorough understanding of the invention. However, it will be apparent to one skilled in the art that the specific details are not required in order to practice the invention. The foregoing descriptions of specific embodiments of the present invention are presented for purposes of illustration and description. They are not intended to be exhaustive or to limit the invention to the precise forms disclosed. Obviously many modifications and variations are possible in view of the above teachings. The embodiments were chosen and described in order to best explain the principles of the invention and its practical applications, the thereby enable others skilled in the art to best utilize the invention and various embodiments with various modifications as are suited to the particular use contemplated. It is intended that the scope of the invention be defined by the following claims and their equivalents.

What is claimed:

1. An apparatus for determining one or more migraine variables associated with migraines, comprising:
   at least one processor;
   at least one memory; and
   at least one program module, the program module stored in the memory and configurable to be executed by the processor, the program module including:
      instructions for determining a statistical relationship between one or more temporal onsets corresponding to one or more events and a pattern of occurrence of a compound variable,
      wherein the compound variable corresponds at least to a pattern of occurrence of a first variable and a pattern of occurrence of a second variable, and
      wherein the determining includes contributions from presence and absence information in the pattern of occurrence of the compound variable; and instructions for identifying the first variable and the second variable as the migraine variables in accordance with the statistical relationship.

2. The apparatus of claim 1, wherein a pattern of occurrence of the first variable is during a first set of time intervals and the pattern of occurrence of a second variable is during a second set of time intervals, and wherein each time interval in a respective set of time intervals precedes a respective temporal onset in the one or more temporal onsets.

3. The apparatus of claim 2, wherein time intervals in at least one of the first set of time intervals and the second set of time intervals are offset in time from the one or more temporal onsets.

4. The apparatus of claim 2, wherein time intervals in the first set of time intervals are different than time intervals in the second set of time intervals.

5. The apparatus of claim 1, the program module further including instructions for receiving information including the one or more temporal onsets corresponding to one or more events and the pattern of occurrence of the compound variable.

6. The apparatus of claim 1, the program module further including instructions for providing recommendations to one or more individuals in accordance with the first variable and the second variable.

7. The apparatus of claim 1, wherein the determining uses a non-parametric statistical analysis technique selected from a group consisting of a chi-square analysis technique, a log-likelihood ratio analysis technique and a Fisher's exact probability analysis technique.

8. The apparatus of claim 1, wherein the determining uses a supervised learning technique selected from a group consisting of a support vector machines (SVM) analysis technique and a classification and regression tree (CART) analysis technique.

9. The apparatus of claim 1, wherein the pattern of occurrence of the first variable and the pattern of occurrence of the second variable comprise categorical data, and wherein a respective entry in the pattern of occurrence of the compound variable is determined by performing a logical operation on corresponding entries in the pattern of occurrence of the first variable and the pattern of occurrence of the second variable.

10. The apparatus of claim 9, wherein the logical operation is a Boolean operation selected from a group consisting of AND, OR, NOT and XOR.

11. The apparatus of claim 1, wherein the statistical relationship is at least in part determined using a filter.

12. The apparatus of claim 1, the program module further including instructions for determining statistical relationships for a plurality of compound variables,
wherein a respective compound variable in the plurality of compound variables corresponds to patterns of occurrence of at least two variables in a set of variables, one of at least the two variables occurring during one set of time intervals and another of at least the two variables occurring during another set of time intervals, and wherein each time interval in a respective set of time intervals precedes a respective temporal onset in the one or more temporal onsets.

13. The apparatus of claim 12, the program module further including instructions for ranking the plurality of compound variables in accordance with the statistical relationships.

14. The apparatus of claim 12, the program module further including instructions for ranking variables in the set of variables in accordance with a number of occurrences of the variables in the compound variables having statistical relationships that approximately exceed a statistical confidence threshold.

15. The apparatus of claim 14, wherein the statistical confidence threshold is selected such that at least a subset of the ranking is substantially stable.

16. The apparatus of claim 1, wherein the pattern of occurrence of the first variable and the pattern of occurrence of the second variable include presence and absence information, and wherein a respective entry in a pattern of occurrence of a respective variable is considered present if the respective entry approximately exceeds at least one threshold.

17. The apparatus of claim 1, wherein the migraine variables are migraine triggers and the one or more events correspond to one or more migraines experienced by at least one individual.

18. The apparatus of claim 17, wherein one or more of the migraine triggers at least in part induce a migraine in at least the one individual if at least the one individual is exposed to one or more of the migraine triggers.

19. The apparatus of claim 17, the program module further including instructions for associating at least the one individual with one or more groups of migraine triggers in accordance with one or more of the identified migraine variables.

20. The apparatus of claim 1, the program module further including instructions for determining a subset of temporal onsets in a set of temporal onsets,
wherein the subset of temporal onsets includes one or more onsets corresponding to one or more migraines experienced by at least one individual, the set of temporal onsets includes the subset of temporal onsets and one or more temporal onsets corresponding to one or more additional headaches experienced by at least the one individual, and wherein the determining of the statistical relationship uses the subset of temporal onsets and the pattern of occurrence of the compound variable.

21. The apparatus of claim 20, wherein the one or more additional headaches are selected from a group consisting of one or more rebound migraines, one or more recurrence migraines and one or more tension headaches.

22. The apparatus of claim 20, wherein the pattern of occurrence of the compound variable includes one or more entries corresponding to at least a time interval after at least a respective temporal onset in the subset of temporal onsets, a respective migraine corresponding to at least the respective temporal onset having a duration including at least the time interval, and wherein the one or more entries are excluded when the statistical relationship is determined.

23. A computer-program product for use in conjunction with a computer system, the computer-program product comprising a computer-readable storage medium and a computer-program mechanism embedded therein for determining one or more migraine variables associated with migraines, the computer-program mechanism including:
instructions for determining a statistical relationship between one or more temporal onsets corresponding to one or more events and a pattern of occurrence of a compound variable,
wherein the compound variable corresponds at least to a pattern of occurrence of a first variable and a pattern of occurrence of a second variable, and wherein the determining includes contributions from presence and absence information in the pattern of occurrence of the compound variable; and instructions for identifying the first variable and the second variable as migraine variables in accordance with the statistical relationship.

24. An apparatus for determining one or more migraine variables associated with migraines, comprising:
- at least one computational means;
- at least one storage means; and
- at least one program module mechanism, the program module mechanism stored in at least the storage means and configurable to be executed by at least the computational means, at least the program module mechanism including:
  - instructions for determining a statistical relationship between one or more temporal onsets corresponding to one or more events and a pattern of occurrence of a compound variable,
  - wherein the compound variable corresponds at least to a pattern of occurrence of a first variable and a pattern of occurrence of a second variable, and wherein the determining includes contributions from presence and absence information in the pattern of occurrence of the compound variable; and
  - instructions for identifying the first variable and the second variable as the migraine variables in accordance with the statistical relationship.

* * * * *